US 8,552,220 B2

(12) United States Patent
Sugimoto et al.

(10) Patent No.: US 8,552,220 B2
(45) Date of Patent: Oct. 8, 2013

(54) THERAPEUTIC AGENT FOR ALZHEIMER'S DISEASE

(75) Inventors: Hachiro Sugimoto, Kyoto (JP); Takashi Takahashi, Tokyo (JP); Ichiro Hijikuro, Tokyo (JP); Michiaki Okuda, Kyoto (JP)

(73) Assignees: Tokyo Institute of Technology, Tokyo (JP); Kyoto University, Kyoto (JP)

( * ) Notice: Subject to any disclaimer, the term of this patent is extended or adjusted under 35 U.S.C. 154(b) by 269 days.

(21) Appl. No.: 12/994,472

(22) PCT Filed: May 27, 2009

(86) PCT No.: PCT/JP2009/059675
§ 371 (c)(1),
(2), (4) Date: Dec. 23, 2010

(87) PCT Pub. No.: WO2009/145219
PCT Pub. Date: Dec. 3, 2009

(65) Prior Publication Data
US 2011/0082295 A1    Apr. 7, 2011

(30) Foreign Application Priority Data

May 30, 2008    (JP) .................................. 2008-141996

(51) Int. Cl.
*C07C 49/248* (2006.01)
(52) U.S. Cl.
USPC .......................................... 568/306; 568/300
(58) Field of Classification Search
USPC ................ 568/300, 306; 540/575; 424/93.21
See application file for complete search history.

(56) References Cited

U.S. PATENT DOCUMENTS

| 2005/0187255 | A1* | 8/2005 | Lee et al. ...................... 514/332 |
| 2006/0258752 | A1* | 11/2006 | Vander Jagt et al. ......... 514/688 |
| 2007/0060644 | A1* | 3/2007 | Vander Jagt et al. ......... 514/475 |
| 2010/0048901 | A1 | 2/2010 | Takahashi et al. |

FOREIGN PATENT DOCUMENTS

| EP | 2 123 637 A1 | 11/2009 |
| JP | 2008-137914 A | 6/2008 |
| JP | 2008-228686 A | 10/2008 |
| WO | WO03/088927 A2 | 10/2003 |
| WO | WO 2008/048410 A2 | 4/2008 |
| WO | WO 2008/066151 A1 | 6/2008 |

OTHER PUBLICATIONS

International Preliminary Report on Patentability issued in PCT/JP2009/059675 on Jan. 20, 2011.

Hironori Ohtsu et al., "Antitumor Agents 222. Synthesis and Antiandrogen Activity of New Diarylheptanoids", Bioorganic & Medicinal Chemistry, 2003, 11(23), pp. 5083-5090.
International Search Report, dated Jun. 12, 2009 and issued in PCT/JP2009/059675.
Junko Ishida et al., Antitumor Agents. Part 214: Synthesis and Evaluation of Curcumin Analogues as Cytotoxic Agents, Bioorganic & Medicinal Chemistry, 2002, 10(11), pp. 3481-3487.
V. D. John et al., Antitumour activity of synthetic curcuminoid analogues (1,7-diaryl-1,6-heptadiene-3,5-diones) and their copper complexes, Applied Organometallic Chemistry, 2006, 20(8), pp. 477-482.
Wei-Yan Shao et al., "Facile preparation of new unsymmetrical curcumin derivatives by solid-phase synthesis strategy", Tetrahedron Letters, 2006, 47(24), pp. 4085-4089.
C. H. Park et al, "Curcumin Derivatives Inhibit the Formation of Jun-Fos-DNA Complex Independently of their Conserved Cysteine Residues", Journal of Biochemistry and Molecular Biology, vol. 38, No. 4, Jul. 2005, pp. 474-480.
F. Yang et al., "Curcumin Inhibits Formation of Amyloid beta Oligomers and Fibrils, Binds Plaques, and Reduces Amyloid in Vivo", Journal of Biological Chemistry, vol. 280, No. 7, Feb. 18, 2005, pp. 5892-5901.
M. Ali et al, "Synthesis and anti-inflammatory activity of some curcumin analogues", Indian Journal of Chemistry, vol. 34B, Oct. 1995, pp. 884-888.
Supplementary European Search Report dated Nov. 8, 2012 for Application No. 09754727.7

* cited by examiner

*Primary Examiner* — Johann R Richter
*Assistant Examiner* — Pancham Bakshi
(74) *Attorney, Agent, or Firm* — Birch, Stewart, Kolasch & Birch, LLP

(57) ABSTRACT

To develop a highly safe measure to treat Alzheimer's disease using a secretase-inhibiting substance, there is provided a compound represented by the following general formula (I) or a salt thereof:

[Formula 1]

wherein A represents a phenyl group or the like, $R^1$ represents a chlorine atom, a bromine atom, or a nitro group or the like, $R^2$, $R^3$, $R^4$, and $R^5$ each represent a hydrogen atom or the like, and L represents $CH_2$—$CH_2$ or CH=CH.

6 Claims, 2 Drawing Sheets

| CU | IC50 [μM] |
|---|---|
| CU127 | 1.0 |
| CU129 | 0.81 |
| CU130 | 1.5 |
| CU131 | 0.91 |
| CU132 | 0.79 |
| CU133 | 0.63 |
| CU192 | 1.5 |
| CU194 | 1.2 |
| CU195 | 1.2 |
| CU196 | 2.0 |
| CU197 | 1.2 |
| CU202 | 1.8 |
| CU362 | 0.72 |
| CU381 | 0.79 |
| CU465 | 1.5 |
| CU467 | 0.85 |
| CU472 | 0.88 |
| CU475 | 0.74 |
| CU477 | 1.9 |
| CU478 | 1.2 |
| CU481 | 1.2 |
| CU492 | 1.6 |
| CU522 | 1.1 |
| CU523 | 2.1 |
| CU524 | 2.4 |
| CU526 | 1.0 |
| CU527 | 0.48 |
| CU528 | 0.49 |

| CU | IC50 [μM] |
|---|---|
| CU529 | 2.7 |
| CU530 | 0.60 |
| CU531 | 0.37 |
| CU532 | 0.33 |
| CU538 | 0.53 |
| CU539 | 1.4 |
| CU541 | 0.91 |
| CU542 | 0.54 |
| CU544 | 0.87 |
| CU549 | 0.78 |
| CU561 | 0.41 |
| CU562 | 0.35 |
| CU574 | 1.0 |
| CU581 | 0.99 |
| CU582 | 0.55 |
| CU584 | 1.7 |
| CU585 | 0.23 |
| CU596 | 0.43 |
| CU600 | 0.51 |
| CU601 | 3.0 |
| CU608 | 0.52 |
| CU609 | 0.79 |
| CU611 | 0.48 |
| CU612 | 0.63 |
| CU613 | 0.80 |
| CU614 | 2.4 |
| CU615 | 1.4 |
| CU616 | 1.5 |

| CU | IC50 [μM] |
|---|---|
| CU621 | 0.97 |
| CU641 | 0.97 |
| CU644 | 1.1 |
| CU648 | 1.1 |
| CU649 | 0.93 |
| CU655 | 1.4 |
| CU657 | 1.1 |
| CU658 | 0.92 |
| CU671 | 0.56 |
| CU672 | 0.68 |
| CU1084 | 2.4 |

FIG. 1

THERAPEUTIC AGENT FOR ALZHEIMER'S DISEASE

TECHNICAL FIELD

The present invention relates to a novel compound, and a β-secretase inhibitor and a preventive or therapeutic agent for a disease associated with β-secretase that utilize the same.

BACKGROUND ART

With the arrival of a rapidly aging society in recent years, senile dementia has become a serious medical and social problem and effective anti-dementia drugs are awaited anxiously. While Alzheimer's disease (AD) has been well studied, its pathogenesis remains unclear. Aricept, the only therapeutic agent for Alzheimer's disease that has been launched in Japan, is based on the inhibitory action on acetylcholinesterase. Although Aricept is very useful for symptomatic treatment, this drug is not a definitive treatment.

One causative substance that induces Alzheimer's disease is thought to be amyloid β protein, which is generated from amyloid precursor protein (APP) through the actions of enzymes called secretases. A compound that has an inhibitory action on these secretases is therefore a promising candidate of a therapeutic agent for Alzheimer's disease. Some compounds that have an inhibitory action on secretases are already known and patent applications for the compounds have been filed (Patent Literatures 1, 2, and 3).

CITATION LIST

Patent Literature

Patent Literature 1: Japanese Patent Laid-Open No. 2002-173448
Patent Literature 2: Japanese Patent Laid-Open No. 2004-149429
Patent Literature 3: WO 2004/076478

SUMMARY OF INVENTION

Technical Problem

Secretase-inhibiting substances can inhibit not only generation of amyloid β protein but also other reactions in the living body. As such substances may cause severe adverse reactions in patients, it is difficult to use the substances in treatment of Alzheimer's disease. An object of the present invention is to provide a highly safe measure to treat Alzheimer's disease using a secretase-inhibiting substance against such a technical background.

Solution to Problem

The present inventor has conducted an intense study to achieve the foregoing object. As a result, the inventor has found that a group of compounds having a 6-phenyl-hex-5-ene-2,4-dione structure as with curcumin contained in turmeric, one of curry spices, have a potent inhibitory action on β-secretase. The inventor has also found that, of the compounds having this structure, compounds that have an electron-withdrawing substituent at the second position of a phenyl group have a potent inhibitory action, and compounds that have a phenyl group substituted with a chlorine atom, a bromine atom, or a nitro group at the second position thereof or with a hydroxyl group at the fourth or fifth position thereof have a particularly potent inhibitory action.

The present invention has been accomplished based on the above-described findings.

Specifically, the present invention provides the following (1) to (10):

(1) A compound represented by the following general formula (I) or a salt thereof:

[Formula 1]

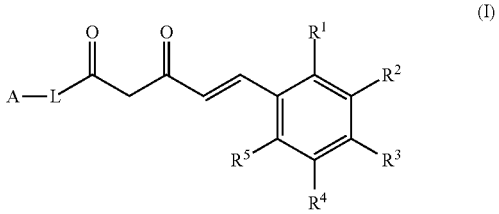

wherein A represents an aryl group that is optionally substituted or a heteroaryl group that is optionally substituted, $R^1$ represents an electron-withdrawing group, $R^2$, $R^3$, $R^4$, and $R^5$ are the same or different and each represent a hydrogen atom or a group with which a benzene ring can be substituted, and L represents $CH_2$—$CH_2$ or CH=CH.

(2) The compound according to (1) or a salt thereof, wherein in the general formula (I), $R^1$ is a fluorine atom, a chlorine atom, a bromine atom, a nitro group, a trifluoromethyl group, a cyano group, an azide group, an alkoxycarbonyl group that is optionally substituted, a carboxyl group, an alkylaminocarbonyl group that is optionally substituted, a dialkylaminocarbonyl group that is optionally substituted, an alkylaminosulfonyl group that is optionally substituted, a dialkylaminosulfonyl group that is optionally substituted, an alkylsulfinyl group that is optionally substituted, an alkylsulfonyl group that is optionally substituted, an alkylsulfonyloxy group that is optionally substituted, an alkylcarbonyloxy group that is optionally substituted, a benzoyl group that is optionally substituted, a phenyl group that is optionally substituted, a naphthyl group that is optionally substituted, a triazolyl group that is optionally substituted, a tetrazolyl group that is optionally substituted, a styryl group that is optionally substituted, or a functional group equivalent thereto and $R^2$, $R^3$, $R^4$, and $R^5$ are the same or different and are each a hydrogen atom, a hydroxyl group, a fluorine atom, a chlorine atom, a bromine atom, an iodine atom, a nitro group, a trifluoromethyl group, a methoxymethoxy group, an alkyl group that is optionally substituted, an alkoxy group that is optionally substituted, a phenyl group that is optionally substituted, a phenoxy group that is optionally substituted, a dialkylamino group that is optionally substituted, a pyridinylmethoxy group that is optionally substituted, a 2-dimethylaminoethoxy group that is optionally substituted, a benzyloxy group that is optionally substituted, a piperidin-1-yl group that is optionally substituted, a 1,4-diazepan-1-yl group that is optionally substituted, or a piperazin-1-yl group that is optionally substituted.

(3) The compound according to (1) or a salt thereof, wherein in the general formula (I), $R^1$ is a chlorine atom, a bromine atom, or a nitro group and $R^2$, $R^3$, $R^4$, and $R^5$ are the same or different and are each a hydrogen atom, a hydroxyl group, a fluorine atom, a chlorine atom, a bromine atom, an iodine atom, a nitro group, a trifluoromethyl group, a methoxymethoxy group, an alkyl group that is optionally substituted, an alkoxy group that is optionally substituted, a phenyl group that is optionally substituted, a phenoxy group that is optionally substituted, a dialkylamino group that is optionally substituted, a pyridinylmethoxy group that is optionally substituted, a 7-dimethylaminoethoxy group that is optionally substituted, a benzyloxy group that is optionally substituted, a piperidin-1-yl group that is optionally substituted, a 1,4-diazepan-1-yl group that is optionally substituted, or a piperazin-1-yl group that is optionally substituted.

(4) The compound according to (1) or a salt thereof, wherein in the general formula (I), $R^1$ is a chlorine atom, a bromine atom, or a nitro group and $R^2$, $R^3$, $R^4$, and $R^5$ are the same or different and are each a hydrogen atom or a hydroxyl group.

(5) The compound according to (1) or a salt thereof, wherein in the general formula (I), $R^1$ is a chlorine atom, a bromine atom, or a nitro group, one of $R^3$ and $R^4$ is a hydroxyl group and the other is a hydrogen atom, and $R^2$ and $R^5$ are each a hydrogen atom.

(6) The compound according to (1) or a salt thereof, wherein in the general formula (I), $R^1$ is a nitro group, $R^2$, $R^3$, and $R^5$ are each a hydrogen atom, and $R^4$ is a hydroxyl group.

(7) The compound according to any of (1) to (6) or a salt thereof, wherein in the general formula (I), L is CH=CH.

(8) The compound according to any of (1) to (7) or a salt thereof, wherein in the general formula (I), A is a phenyl group or an indolyl group that is optionally substituted with one or two or more substituents selected from the following substituent group a, the substituent group a consisting of an electron-withdrawing group, a hydroxyl group, an alkoxy group that is optionally substituted, and a dialkylamino group that is optionally substituted.

(9) A β-secretase inhibitor, comprising a compound according to any of (1) to (8) or a salt thereof as an active ingredient.

(10) A preventive or therapeutic agent for a disease associated with β-secretase, comprising a compound according to any of (1) to (8) or a salt thereof as an active ingredient.

Advantageous Effects of Invention

Because the compound represented by the general formula (I) (hereinafter referred to as "the compound of the present invention") has a structure similar to that of curcumin contained in food, the compound inhibits β-secretase without affecting the human body adversely and is therefore considered to be useful in the treatment of Alzheimer's disease or the like. Furthermore, the compound of the present invention can be used not only for direct treatment of Alzheimer's disease but also for development of novel therapeutic agents for Alzheimer's disease or the like and assessment of the influence of β-secretase inhibition on the living body.

BRIEF DESCRIPTION OF DRAWINGS

FIG. 1 shows the results of determination of 50% inhibitory concentrations against β-secretase.

DESCRIPTION OF EMBODIMENTS

Figure 2:
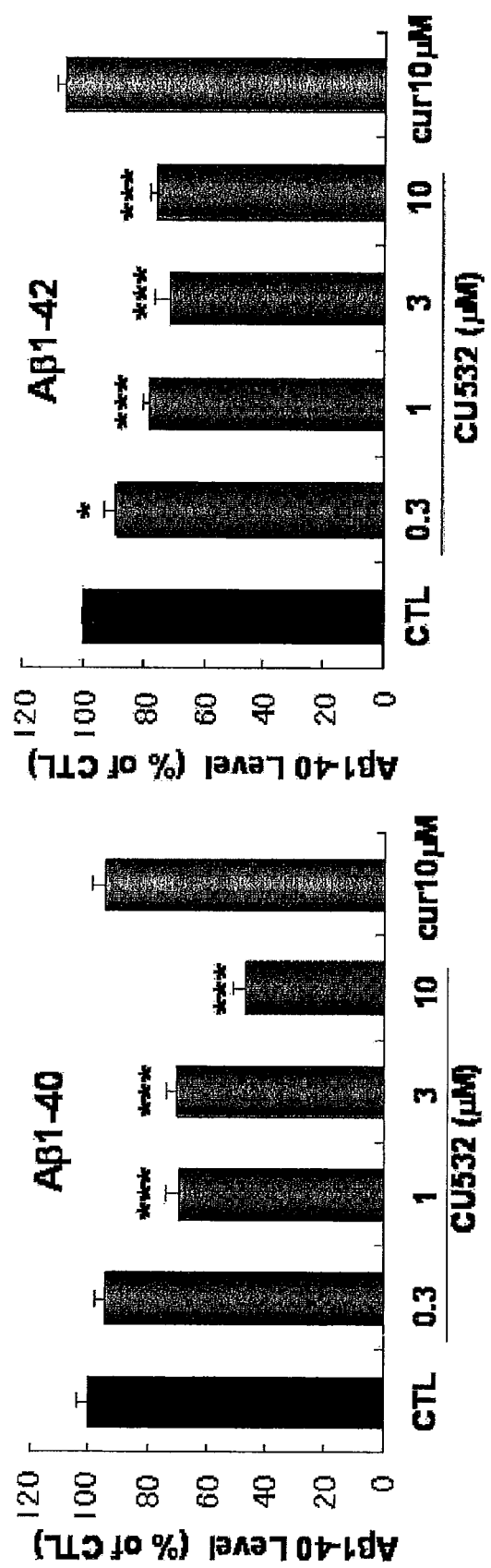
FIG. 2 shows the results of determination of the Aβ1-40 and Aβ1-42 production-suppressing actions of CU532 in rat nerve cells in the primary culture.

The present invention will be described below in detail.
In the present invention, examples of "alkyl" include alkyl having 1 to 20 carbon atoms, and alkyl having 1 to 8 carbon atoms is preferred.

In the present invention, examples of "alkoxy" include alkoxy having 1 to 20 carbon atoms, and alkoxy having 1 to 8 carbon atoms is preferred.

In the present invention, examples of "naphthyl group" include a 1-naphthyl group and a 2-naphthyl group.

In the present invention, examples of "indolyl group" include a 1H-indol-2-yl group, a 1H-indol-3-yl group, a 1H-indol-4-yl group, a 1H-indol-5-yl group, a 1H-indol-6-yl group, and a 1H-indol-7-yl group.

In the present invention, examples of "pyridinylmethoxy group" include a pyridin-2-ylmethoxy group and a pyridin-3-ylmethoxy group.

In the present invention, examples of "triazolyl group" include a 1H-1,2,4-triazol-1-yl group, a 1H-1,2,3-triazol-1-yl group, a 1H-1,2,3-triazol-4-yl group, and a 1H-1,2,3-triazol-5-yl group.

In the present invention, examples of "tetrazolyl group" include 1H-tetrazol-5-yl group.

In the present invention, examples of "functional group equivalent thereto" are as follows: examples of the functional group equivalent to a chloro atom include a thiocyanate group and 2,2-difluorovinyl group, examples of the functional group equivalent to a carboxyl group include an oxadiazolyl group, an isoxazolyl group, a hydroxamate group, a phosphate group, a sulfo group, and a sulfonamide group, examples of the functional group equivalent to an alkoxycarbonyl group that is optionally substituted include an oxazolyl group and a thiazolyl group, and examples of the functional group equivalent to a phenyl group that is optionally substituted include an ethynyl group and cyclohexenyl group.

In the present invention, substituents for "alkoxycarbonyl group that is optionally substituted," "alkylaminocarbonyl group that is optionally substituted," "dialkylaminocarbonyl group that is optionally substituted," "alkylaminosulfonyl group that is optionally substituted," "dialkylaminosulfonyl group that is optionally substituted," "alkylsulfinyl group that is optionally substituted," "alkylsulfonyl group that is optionally substituted," "alkylsulfonyloxy group that is optionally substituted," "alkylcarbonyloxy group that is optionally substituted," "benzoyl group that is optionally substituted," "phenyl group that is optionally substituted," "naphthyl group that is optionally substituted," "alkyl group that is optionally substituted," "alkoxy group that is optionally substituted," "phenoxy group that is optionally substituted," "dialkylamino group that is optionally substituted," "pyridinylmethoxy group that is optionally substituted," "2-dimethylaminoethoxy group that is optionally substituted," "benzyloxy group that is optionally substituted," "triazolyl group that is optionally substituted," "tetrazolyl group that is optionally substituted," "styryl group that is optionally substituted," "piperidin-1-yl group that is optionally substituted," "1,4-diazepan-1-yl group that is optionally substituted," and "piperazin-1-yl group that is optionally substituted" may be any substituents as long as the substituents are groups with which the groups described above can be substituted, and examples thereof include a fluorine atom, a chlorine atom, a bromine atom, an iodine atom, a nitro group, a trifluoromethyl group, a hydroxyl group, an alkyl group, a cycloalkyl group, an alkoxy group, a phenyl group, a phenoxy group, an alkylamino group, a dialkylamino group, an ethoxycarbonyl group, a benzyl group, an ethoxycarbonylmethyl group, an isobutoxy group, a 4-tert-butoxycarbonyl group, and a heterocyclic ring. Two or more of these may be taken together to form a substituent.

In the general formula (I), $R^1$ is preferably a fluorine atom, a chlorine atom, a bromine atom, a nitro group, a trifluoromethyl group, a cyano group, an alkoxycarbonyl group that is optionally substituted, a carboxyl group, an alkylaminocarbonyl group that is optionally substituted, a dialkylaminocarbonyl group that is optionally substituted, an alkylaminosulfonyl group that is optionally substituted, a dialkylaminosulfonyl group that is optionally substituted, an alkylsulfinyl group that is optionally substituted, an alkylsulfonyl group that is optionally substituted, an alkylsulfonyloxy group that is optionally substituted, an alkylcarbonyloxy group that is optionally substituted, a benzoyl group that is optionally substituted, a phenyl group that is optionally substituted, a naphthyl group that is optionally substituted, a triazolyl group that is optionally substituted, a tetrazolyl group that is optionally substituted, a styryl group that is optionally substituted, or a functional group equivalent thereto, more preferably a chlorine atom, a bromine atom, or a nitro group, and further preferably a nitro group.

In the general formula (I), $R^3$ and $R^4$ preferably are the same or different and are each a hydrogen atom, a hydroxyl group, a fluorine atom, a chlorine atom, a bromine atom, an iodine atom, a nitro group, a trifluoromethyl group, a methoxymethoxy group, an alkyl group that is optionally substituted, an alkoxy group that is optionally substituted, a phenyl group that is optionally substituted, a phenoxy group that is optionally substituted, a dialkylamino group that is optionally substituted, a pyridinylmethoxy group that is optionally substituted, a 2-dimethylaminoethoxy group that is optionally substituted, a benzyloxy group that is optionally substituted, a piperidin-1-yl group that is optionally substituted, a 1,4-diazepan-1-yl group that is optionally substituted, or a piperazin-1-yl group that is optionally substituted, and more preferably are the same or different and are each a hydrogen atom or a hydroxyl group. Further preferably, one $R^3$ and $R^4$ is a hydroxyl group and the other is a hydrogen atom. Most preferably, $R^3$ is a hydrogen atom and $R^4$ is a hydroxyl group.

In the general formula (I), $R^2$ and $R^5$ preferably are the same or different and are each a hydrogen atom, a hydroxyl group, a fluorine atom, a chlorine atom, a bromine atom, an iodine atom, a nitro group, a trifluoromethyl group, a methoxymethoxy group, an alkyl group that is optionally substituted, an alkoxy group that is optionally substituted, a phenyl group that is optionally substituted, a phenoxy group that is optionally substituted, a dialkylamino group that is optionally substituted, a pyridinylmethoxy group that is optionally substituted, a 2-dimethylaminoethoxy group that is optionally substituted, a benzyloxy group that is optionally substituted, a piperidin-1-yl group that is optionally substituted, a 1,4-diazepan-1-yl group that is optionally substituted, or a piperazin-1-yl group that is optionally substituted, and more preferably are the same or different and are each a hydrogen atom or a hydroxyl group, and further preferably a hydrogen atom.

In the general formula (I), L is preferably CH=CH.

In the general formula (I), A is preferably a phenyl group that is optionally substituted with one or two or more substituents selected from the group consisting of an electron-withdrawing group, a hydroxyl group, an alkoxy group that is optionally substituted, and a dialkylamino group that is optionally substituted or an indolyl group, more preferably a phenyl group that is substituted with one or two or more substituents selected from the group consisting of a hydroxyl group, a methoxy group, and a chlorine atom, further preferably a 4-hydroxyphenyl group, a 4-hydroxy-3-methoxyphenyl group, a 3-hydroxy-4-methoxyphenyl group, a 4-hydroxy-2-methoxyphenyl group, or a 4-hydroxy-2-chlorophenyl group, and most preferably a 4-hydroxyphenyl group, a 4-hydroxy-2-methoxyphenyl group, or a 4-hydroxy-2-chlorophenyl group.

Representative examples of the compound represented by the general formula (I) include compounds described in Examples 1 to 129 provided below.

Instead of the compound of the present invention, salts of the compound of the present invention may also be used. Such salts are preferably pharmacologically acceptable salts and examples thereof include alkali metal salts (sodium salts, potassium salts), alkaline earth metal salts (calcium salts, magnesium salts), sulfates, hydrochlorides, and nitrates.

Of the compounds represented by the general formula (I), compounds wherein L is CH=CH (compounds represented by general formula [Ia]) gap can be produced by known methods (for example, a method described in National Publication of International Patent Application No. 11-502232). Specifically, these compounds can be produced by steps 1 and 2 described below.

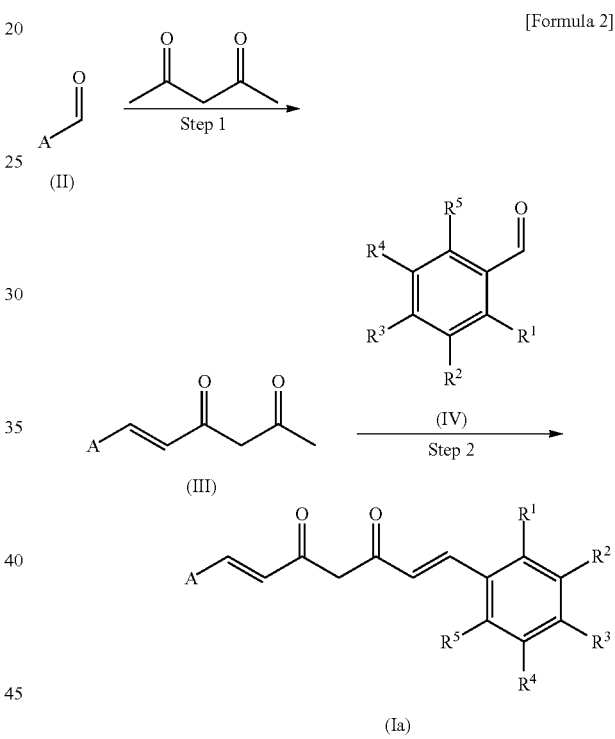

wherein A and $R^1$ to $R^5$ have the same meanings as defined above.

Step 1 is a step of reacting an aldehyde represented by general formula (II) with 2,4-pentanedione in the presence of a solvent and a catalyst to give a compound represented by general formula (III).

The solvent used is not particularly limited so long as the solvent does not inhibit the reaction and examples thereof include ethyl acetate, N,N-dimethylacetamide, N,N-dimethylformamide, N-methylpyrrolidinone, dimethyl sulfoxide, tetrahydrofuran, and acetonitrile. A solvent thereof may be used solely or two or more solvents thereof may be mixed at a suitable ratio and used as necessary.

The catalyst used is not particularly limited either and examples thereof include bases such as primary amines and secondary amines. More specific examples include n-butylamine, ethanolamine, piperidine, and morpholine.

Furthermore, a water scavenger may be added to scavenge water generated by the reaction. Examples of the water scavenger include alkyl borates, alkyl phosphates, and orthoesters. More specific examples include trimethyl orthoformate and tri-n-butyl borate.

The volume ratio of an aldehyde represented by the general formula (II) and 2,4-pentanedione is not particularly limited and is preferably 0.5 to 10 moles, more preferably 1 to 5 moles of the latter, to 1 mole of the former.

The reaction temperature is not particularly limited and is preferably 0° C. to 200° C., more preferably 50° C. to 100° C.

The reaction time is not particularly limited either and is preferably 0.5 to 48 hours, more preferably 1 to 24 hours.

The aldehyde represented by the general formula (II) that is used in step 1 is a commercially available product, a product synthesized from a commercially available product by a known method, or a product synthesized by a novel method described in the Examples. In addition, 2,4-pentanedione is a commercially available product.

Step 2 is a step of reacting a compound represented by the general formula (III) with a benzaldehyde derivative represented by general formula (IV) in the presence of a solvent and a catalyst to give a compound represented by the general formula (Ia).

The solvent used is not particularly limited as long as the solvent does not inhibit the reaction and examples thereof include ethyl acetate, N,N-dimethylacetamide, N,N-dimethylformamide, N-methylpyrrolidinone, dimethyl sulfoxide, tetrahydrofuran, and acetonitrile. A solvent thereof may be used solely or two or more solvents thereof may be mixed at a suitable ratio and used as necessary.

The catalyst used is not particularly limited either and examples thereof include bases such as primary amines and secondary amines. More specific examples include n-butylamine, ethanolamine, piperidine, and morpholine.

Furthermore, a water scavenger may be added to scavenge water generated by the reaction. Examples of the water scavenger include alkyl borates, alkyl phosphates, and orthoesters. More specific examples include trimethyl orthoformate and tri-n-butyl borate.

The volume ratio of a compound represented by the general formula (III) and a benzaldehyde derivative represented by the general formula (IV) is not particularly limited and is preferably 0.1 to 10 moles, more preferably 0.5 to 5 moles of the latter, to 1 mole of the former.

The reaction temperature is not particularly limited and is preferably 0° C. to 200° C., more preferably 50° C. to 100° C.

The reaction time is not particularly limited either and is preferably 0.5 to 48 hours, more preferably 1 to 24 hours.

The benzaldehyde derivative represented by the general formula (IV) that is used in step 2 is a commercially available product, a product synthesized from a commercially available product by a known method, or a product synthesized by a novel method described in the Examples.

When an aldehyde with a free hydroxyl group is low in reactivity in step 2, the reactivity may be improved by using an aldehyde with a protected hydroxyl group instead. The protecting group in this case is not particularly limited. If deprotection is performed at the same time as treatment with hydrochloric acid in the present step, a protecting group that is eliminated with an acid is preferred. Examples thereof include a methoxymethyl group and a t-butyldimethylsilyl group.

Of the compounds represented by the general formula (I), compounds in which L is $CH_2$—$CH_2$ (compounds represented by general formula (Ib)) can be produced by steps 3 and 4 described below.

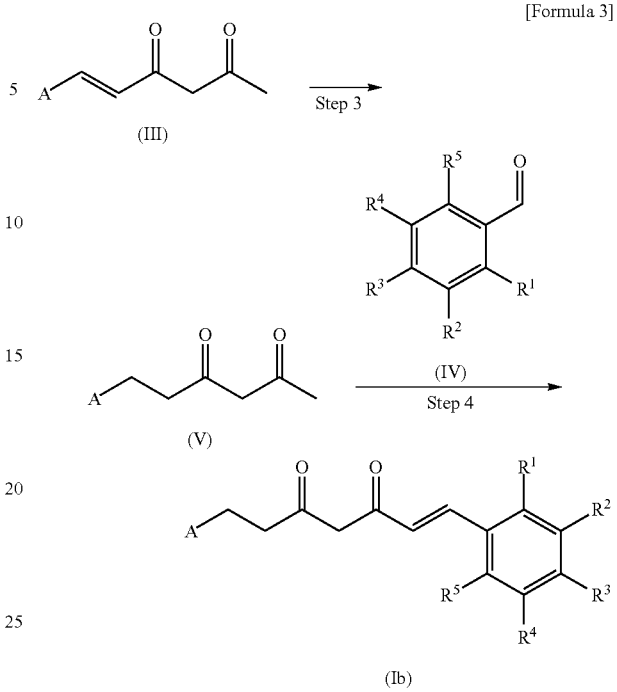

wherein A and $R^1$ to $R^5$ have the same meanings as defined above.

Step 3 is a step of reducing the compound represented by the general formula (III) in the presence of a solvent and a catalyst to give a compound represented by general formula (V).

The solvent used is not particularly limited as long as the solvent does not inhibit the reaction and examples thereof include ester solvents such as ethyl acetate, alcohol solvents such as methanol, ethanol, and isopropanol, and ether solvents such as tetrahydrofuran, diethyl ethers, and dimethoxyethane. A solvent thereof may be used solely or two or more solvents thereof may be mixed at a suitable ratio and used as necessary.

The catalyst used is not particularly limited either and examples thereof include palladium catalysts such as palladium carbon and nickel catalysts such as Raney nickel and nickel diatomaceous earth.

The reaction temperature is not particularly limited and is preferably −40° C. to 200° C., more preferably 0° C. to 100° C.

The reaction time is not particularly limited either and is preferably 0.1 to 48 hours, more preferably 0.5 to 24 hours.

Step 4 is a step of reacting the compound represented by the general formula (V) with a benzaldehyde derivative represented by the general formula (IV) in the presence of a solvent and a catalyst to give a compound represented by the general formula (Ib). Step 4 can be implemented in the same manner as step 2.

The compound of the present invention has a β-secretase inhibiting activity and is therefore effective in preventing and treating diseases associated with β-secretase, such as Alzheimer's disease (familial Alzheimer's disease and sporadic Alzheimer's disease), senile dementia, Down's syndrome, Parkinson's disease, Creutzfelt-Jacob disease, amyotrophic lateral sclerosis, diabetic neuropathy, Huntington's disease, and multiple sclerosis. Of these neurogenic diseases, the compound of the present invention is particularly effective in preventing and treating Alzheimer's disease.

When the compound of the present invention is used as a preventive or therapeutic agent for Alzheimer's disease or the like, the compound can be mixed with a pharmaceutically acceptable carrier or diluent according to a known method to prepare a formulation. The dosage form is not particularly limited and examples thereof include a tablet, a powder, a granule, a capsule, a solution, an injection, a suppository, and a sustained-release agent. The administration method is not particularly limited either and the compound can be administered orally or parenterally (topical, rectal, or intravenous administration). The dosage varies depending on the administration target, administration method, disease type, and the like. For example, if the compound of the present invention is orally administered to adults as a therapeutic agent for Alzheimer's disease, then the compound can be administered in a single dose or divided into several doses per day so that the dose is 0.1 to 500 mg.

The compound of the present invention can be used in a method for treating a disease associated with β-secretase. Specific examples of the method include (A) described below.

(A) A method for treating diseases associated with β-secretase, comprising a step of administering a compound represented by the general formula (I) or a salt thereof to a patient with a disease associated with β-secretase.

The compound of the present invention can also be used in a method for inhibiting β-secretase.

Specific examples of the method include (B) and (C) described below.

(B) A method for inhibiting β-secretase, comprising a step administering a compound represented by the general formula (I) or a salt thereof to a human to inhibit β-secretase in the human body.

(C) A method for inhibiting β-secretase, comprising a step of bringing a compound represented by the general formula (I) or a salt thereof into contact with β-secretase.

EXAMPLES

The present invention will be described below in further detail with reference to Examples and the like. It is to be noted that synthesized compounds in the Examples are designated as compounds having a structure represented by the general formula (Ia) or (Ib) shown below and these are detected as compounds having structures represented by the general formula (Ia') or (Ib') shown below, respectively, in 1H NMR (heavy acetone solvent, room temperature). Therefore, compounds detected as compounds having not a structure represented by the general formula (Ia) or (Ib) but a structure represented by the general formula (Ia') or (Ib') in 1H NMR are also included in the synthesized compounds in the Examples. Furthermore, the melting point may be a value different from those shown in the Synthesis Examples depending on the crystalline system or the degree of mixture of impurities.

Example 1

Synthesis of (1E,6E)-1-(2-chloro-4-hydroxyphenyl)-7-(4-hydroxyphenyl)hepta-1,6-diene-3,5-dione (CU127)

6-(4-Hydroxyphenyl)hex-5-ene-2,4-dione (17.5 mg, 85 μmol) and boron trioxide (11 mg, 0.16 mmol) was placed in a 20 mL reaction vessel, and dissolved in 0.4 mL of ethyl acetate. To the stirring mixture at 80° C. was added a solution of 2-chloro-4-hydroxybenzaldehyde (17 mg, 0.11 mmol) and tri-n-butyl borate (25 μL, 93 μmol, sequentially. After the reaction mixture was stirred for 2 h at the same temperature, n-butylamine (10 μL, 0.10 mmol) was added with additional stirring for 1 h. The reaction mixture was treated with a 1:1 solution (1 mL) of 1N HCl and brine at room temperature, and was stirred at 50° C. for 5 min to 1 h (if necessary, the reaction mixture was neutralized by saturated $NaHCO_3$ aqueous solution). The organic layer was purified directly by silica gel column chromatography (eluting with hexane/ethyl acetate or chloroform/methanol) to obtain the title compound (13.2 mg, 45%) as a solid.

$^1$H NMR (δ, acetone-$d_6$): 6.01 (s, 1H), 6.69 (d, J=16 Hz, 1H), 6.74 (d, J=16 Hz, 1H), 6.87~6.9 (m, 1H), 6.91 (d, J=8.7 Hz, 2H), 6.98 (d, J=2.4 Hz, 1H), 7.58 (d, J=8.7 Hz, 2H), 7.63 (d, J=16 Hz, 1H), 7.78 (d, J=8.7 Hz, 1H), 7.97 (d, J=16 Hz, 1H), 9.0 (br s, OH).

Melting Point 131-138° C., MS (ESI+) m/z 343 (M+1), 365 (M+Na).

Example 2

Synthesis of (1E,6E)-1-(2-chloro-4-hydroxyphenyl)-7-(4-hydroxy-3-methoxyphenyl)hepta-1,6-diene-3,5-dione (CU129)

6-(4-Hydroxy-3-methoxyphenyl)hex-5-ene-2,4-dione (20 mg, 85 μmol) and boron trioxide (11 mg, 0.16 mmol) was placed in a 20 mL reaction vessel, and dissolved in 0.4 mL of ethyl acetate. To the stirring mixture at 80° C. was added a solution of 2-chloro-4-hydroxybenzaldehyde (17 mg, 0.11 mmol) and tri-n-butyl borate (25 μL, 93 μmol), sequentially. After the reaction mixture was stirred for 2 h at the same temperature, n-butylamine (10 μL, 0.10 mmol) was added with additional stirring for 1 h. The reaction mixture was treated with a 1:1 solution (1 mL) of 1N HCl and brine at room temperature, and was stirred at 50° C. for 5 min to 1 h (if necessary, the reaction mixture was neutralized by saturated $NaHCO_3$ aqueous solution). The organic layer was purified directly by silica gel column chromatography (eluting with hexane/ethyl acetate or chloroform/methanol) to obtain the title compound (8.0 mg, 25%) as a solid.

$^1$H NMR (δ, acetone-$d_6$): 3.92 (s, 3H), 6.01 (s, 1H), 6.74 (d, J=16 Hz, 1H), 6.74 (d, J=16 Hz, 1H), 6.89 (d, J=8.2 Hz, 1H), 6.90 (dd, J=2.4, 8.8 Hz, 1H), 6.98 (d, J=2.4 Hz, 1H), 7.19 (dd, J=1.9, 8.2 Hz, 1H), 7.36 (d, J=1.9 Hz, 1H), 7.63 (d, J=16 Hz, 1H), 7.79 (d, J=8.8 Hz, 1H), 7.97 (d, J=16 Hz, 1H).

Melting Point 185-192° C., MS (ESI+) m/z 373 (M+1).

Example 3

Synthesis of (1E,6E)-1-(2-chloro-4-hydroxyphenyl)-7-(3-hydroxy-4-methoxyphenyl)hepta-1,6-diene-3,5-dione (CU130)

6-(3-Hydroxy-4-methoxyphenyl)hex-5-ene-2,4-dione (20 mg, 85 μmol) and boron trioxide (11 mg, 0.16 mmol) was placed in a 20 mL reaction vessel, and dissolved in 0.4 mL of ethyl acetate. To the stirring mixture at 80° C. was added a solution of 2-chloro-4-hydroxybenzaldehyde (17 mg, 0.11 mmol) and tri-n-butyl borate (25 μL, 93 μmol), sequentially. After the reaction mixture was stirred for 2 h at the same temperature, n-butylamine (10 μL, 0.10 mmol) was added with additional stirring for 1 h. The reaction mixture was treated with a 1:1 solution (1 mL) of 1N HCl and brine at room temperature, and was stirred at 50° C. for 5 min to 1 h (if necessary, the reaction mixture was neutralized by saturated NaHCO$_3$ aqueous solution). The organic layer was purified directly by silica gel column chromatography (eluting with hexane/ethyl acetate or chloroform/methanol) to obtain the title compound (7.4 mg, 23%) as a solid.

$^1$H NMR (δ, acetone-d$_6$): 3.90 (s, 3H), 6.03 (s, 1H), 6.70 (d, J=16 Hz, 1H), 6.76 (d, J=16 Hz, 1H), 6.89 (dd, J=2.4, 8.8 Hz, 1H), 6.98 (d, J=2.4 Hz, 1H), 7.01 (d, J=8.2 Hz, 1H), 7.15 (dd, J=1.9, 8.2 Hz, 1H), 7.21 (d, J=1.9 Hz, 1H), 7.59 (d, J=16 Hz, 1H), 7.80 (d, J=8.8 Hz, 1H), 7.98 (d, J=16 Hz, 1H).

Melting Point 120-130° C., MS (ESI+) m/z 373 (M+1).

Example 4

Synthesis of (1E,6E)-1-(5-hydroxy-2-nitrophenyl)-7-(4-hydroxyphenyl)hepta-1,6-diene-3,5-dione (CU131)

The title compound was synthesized using the same procedure employed for Example 1, but with 5-hydroxy-2-nitrobenzaldehyde (18 mg, 0.11 mmol) instead of 2-chloro-4-hydroxybenzaldehyde (17 mg, 0.11 mmol). The product was obtained as a solid (7.8 mg, 26%) having the following characteristics.

$^1$H NMR (δ, acetone-d$_6$): 6.12 (s, 1H), 6.73 (d, J=16 Hz, 1H), 6.73 (d, J=16 Hz, 1H), 6.91 (d, J=8.7 Hz, 2H), 7.06 (dd, J=2.4, 8.8 Hz, 1H), 7.22 (d, J=2.4 Hz, 1H), 7.60 (d, J=8.7 Hz, 2H), 7.68 (d, J=16 Hz, 1H), 8.08 (d, J=8.8 Hz, 1H), 8.11 (d, J=16 Hz, 1H).

Melting Point 187-194° C., MS (ESI+) m/z 354 (M+1), 376 (M+Na).

Example 5

Synthesis of (1E,6E)-1-(4-hydroxy-3-methoxyphenyl)-7-(5-hydroxy-2-nitrophenyl)hepta-1,6-diene-3,5-dione (CU132)

The title compound was synthesized using the same procedure employed for Example 2, but with 5-hydroxy-2-nitrobenzaldehyde (18 mg, 0.11 mmol) instead of 2-chloro-4-hydroxybenzaldehyde (17 mg, 0.11 mmol). The product was obtained as a solid (5.8 mg, 18%) having the following characteristics.

1H NMR (δ, acetone-d$_6$): 3.93 (s, 3H), 6.10 (s, 1H), 6.72 (d, J=16 Hz, 1H), 6.78 (d, J=16 Hz, 1H), 6.89 (d, J=8.2 Hz, 1H), 7.06 (dd, J=2.4, 8.8 Hz, 1H), 7.25~7.35 (m, 2H), 7.37 (d, J=1.9 Hz, 1H), 7.67 (d, J=16 Hz, 1H), 8.08 (d, J=8.8 Hz, 1H), 8.11 (d, J=16 Hz, 1H).

Melting Point 147-152° C., MS (ESI+) m/z 384 (M+1), 406 (M+Na).

Example 6

Synthesis of (1E,6E)-1-(3-hydroxy-4-methoxyphenyl)-7-(5-hydroxy-2-nitrophenyl)hepta-1,6-diene-3,5-dione (CU133)

The title compound was synthesized using the same procedure employed for Example 3, but with 5-hydroxy-2-nitrobenzaldehyde (18 mg, 0.11 mmol) instead of 2-chloro-4-hydroxybenzaldehyde (17 mg, 0.11 mmol). The product was obtained as a solid (11.4 mg, 35%) having the following characteristics.

$^1$H NMR (δ, acetone-d$_6$): 3.90 (s, 3H), 6.12 (s, 1H), 6.72 (d, J=16 Hz, 1H), 6.73 (d, J=16 Hz, 1H), 7.01 (d, J=8.7 Hz, 1H), 7.05 (dd, J=2.4, 8.7 Hz, 1H), 7.17 (dd, J=1.9, 8.7 Hz, 1H), 7.21 (d, J=2.4 Hz, 1H), 7.22 (d, J=1.9 Hz, 1H), 7.63 (d, J=16 Hz, 1H), 8.07 (d, J=8.7 Hz, 1H), 8.11 (d, J=16 Hz, 1H).

Melting Point 107-111° C., MS (ESI+) m/z 384 (M+1), 406 (M+Na).

Example 7

Synthesis of (1E,6E)-1-(2,4-dichlorophenyl)-7-(4-hydroxy-3-methyoxyphenyl)hepta-1,6-diene-3,5-dione (CU144)

The title compound was synthesized using the same procedure employed for Example 2, but with 2,4-dichlorobenzaldehyde (19 mg, 0.11 mmol) instead of 2-chloro-4-hydroxybenzaldehyde (17 mg, 0.11 mmol). The product was obtained as a solid (6.2 mg, 19%) having the following characteristics.

$^1$H NMR (δ, acetone-d$_6$): 3.92 (s, 3H), 6.09 (s, 1H), 6.77 (d, J=16 Hz, 1H), 6.89 (d, J=8.2 Hz, 1H), 6.93 (d, J=16 Hz, 1H), 7.20 (dd, J=~2, 8.2 Hz, 1H), 7.36 (d, J=~2 Hz, 1H), 7.45 (dd, J=2.4, 7.8 Hz, 1H), 7.61 (d, J=2.4 Hz, 1H), 7.67 (d, J=16 Hz, 1H), 7.91 (d, J=7.8 Hz, 1H), 7.92 (d, J=16 Hz, 1H), 8.2 (br s, OH).

Melting Point 124-130° C., MS (ESI+) m/z 391 (M+1), 413 (M+Na).

Example 8

Synthesis of (1E,6E)-1-(2,4-dichlorophenyl)-7-(3-hydroxy-4-methoxyphenyl)hepta-1,6-diene-3,5-dione (CU145)

The title compound was synthesized using the same procedure employed for Example 3, but with 2,4-dichlorobenzaldehyde (19 mg, 0.11 mmol) instead of 2-chloro-4-hydroxybenzaldehyde (17 mg, 0.11 mmol). The product was obtained as a solid (8.7 mg, 26%) having the following characteristics.

$^1$H NMR (δ, acetone-d$_6$): 3.90 (s, 3H), 6.10 (s, 1H), 6.72 (d, J=16 Hz, 1H), 6.93 (d, J=16 Hz, 1H), 6.98 (d, J=8.2 Hz, 1H), 7.10 (dd, J=~2, 8.2 Hz, 1H), 7.22 (d, J=~2 Hz, 1H), 7.45 (dd, J=2.4, 7.8 Hz, 1H), 7.60 (d, J=2.4 Hz, 1H), 7.63 (d, J=16 Hz, 1H), 7.8 (br s, OH), 7.92 (d, J=7.8 Hz, 1H), 7.93 (d, J=16 Hz, 1H).

MS (ESI+) m/z 391 (M+1), 413 (M+Na).

Example 9

Synthesis of (1E,6E)-1-(2,4-dichlorophenyl)-7-(4-hydroxyphenyl)hepta-1,6-diene-3,5-dione (CU146)

The title compound was synthesized using the same procedure employed for Example 1, but with 2,4-dichlorobenzaldehyde (19 mg, 0.11 mmol) instead of 2-chloro-4-hydroxybenzaldehyde (17 mg, 0.11 mmol). The product was obtained as a solid (6.6 mg, 22%) having the following characteristics.

$^1$H NMR (δ, acetone-d$_6$): 6.09 (s, 1H), 6.72 (d, J=16 Hz, 1H), 6.91 (d, J=8.7 Hz, 2H), 6.93 (d, J=16 Hz, 1H), 7.45 (dd, J=~2, 8.7 Hz, 1H), 7.57 (d, J=8.7 Hz, 2H), 7.60 (d, J=~2 Hz, 1H), 7.67 (d, J=16 Hz, 1H), 7.91 (d, J=8.7 Hz, 1H), 7.92 (d, J=16 Hz, 1H), 8.9 (br s, OH). MS (ESI+) m/z 361 (M+1).

Example 10

Synthesis of (1E,6E)-1-(2,5-dichlorophenyl)-7-(4-hydroxy-3-methyoxyphenyl)hepta-1,6-diene-3,5-dione (CU184)

The title compound was synthesized using the same procedure employed for Example 2, but with 2,5-dichlorobenzaldehyde (19 mg, 0.11 mmol) instead of 2-chloro-4-hydroxybenzaldehyde (17 mg, 0.11 mmol). The product was obtained as a solid (7.4 mg, 22%) having the following characteristics.

$^1$H NMR ($\delta$, acetone-$d_6$): 3.92 (s, 3H), 6.11 (s, 1H), 6.79 (d, J=16 Hz, 1H), 6.89 (d, J=8.2 Hz, 1H), 7.01 (d, J=16 Hz, 1H), 7.22 (dd, J=~2, 8.2 Hz, 1H), 7.38 (d, J=~2 Hz, 1H), 7.45 (dd, J=2.4, 8.7 Hz, 1H), 7.54 (d, J=8.7 Hz, 1H), 7.68 (d, J=16 Hz, 1H), 7.90 (d, J=16 Hz, 1H), 7.92 (d, J=2.4 Hz, 1H).

Melting Point 142-147° C., MS (ESI+) m/z 391 (M+1), 413 (M+Na).

Example 11

Synthesis of (1E,6E)-1-(2,5-dichlorophenyl)-7-(3-hydroxy-4-methyoxyphenyl)hepta-1,6-diene-3,5-dione (CU185)

The title compound was synthesized using the same procedure employed for Example 3, but with 2,5-dichlorobenzaldehyde (19 mg, 0.11 mmol) instead of 2-chloro-4-hydroxybenzaldehyde (17 mg, 0.11 mmol). The product was obtained as a solid (6.8 mg, 20%) having the following characteristics.

$^1$H NMR ($\delta$, acetone-$d_6$): 3.90 (s, 3H), 6.13 (s, 1H), 6.74 (d, J=16 Hz, 1H), 7.01 (d, J=8.2 Hz, 1H), 7.03 (d, J=16 Hz, 1H), 7.18 (dd, J=1.9, 8.2 Hz, 1H), 7.23 (d, J=1.9 Hz, 1H), 7.45 (dd, J=2.4, 8.7 Hz, 1H), 7.54 (d, J=8.7 Hz, 1H), 7.64 (d, J=16 Hz, 1H), 7.90 (d, J=16 Hz, 1H), 7.94 (d, J=2.4 Hz, 1H).

Melting Point 140-146° C., MS (ESI+) m/z 391 (M+1), 413 (M+Na).

Example 12

Synthesis of (1E,6E)-1-(4-dimethylamino-2-nitrophenyl)-7-(4-hydroxy-3-methyoxyphenyl)hepta-1,6-diene-3,5-dione (CU192)

The title compound was synthesized using the same procedure employed for Example 2, but with 4-dimethylamino-2-nitrobenzaldehyde (21 mg, 0.11 mmol) instead of 2-chloro-4-hydroxybenzaldehyde (17 mg, 0.11 mmol). The product was obtained as a solid (6.4 mg, 18%) having the following characteristics.

$^1$H NMR ($\delta$, acetone-$d_6$): 3.13 (s, 6H), 3.92 (s, 3H), 5.99 (s, 1H), 6.70 (d, J=16 Hz, 1H), 6.73 (d, J=16 Hz, 1H), 6.88 (d, J=8.2 Hz, 1H), 7.05 (dd, J=2.9, 9.2 Hz, 1H), 7.16 (d, J=2.9 Hz, 1H), 7.18 (dd, J=~2, 8.2 Hz, 1H), 7.34 (d, J=~2 Hz, 1H), 7.61 (d, J=16 Hz, 1H), 7.81 (d, J=16 Hz, 1H), 7.82 (d, J=9.2 Hz, 1H), 8.1 (br s, OH).

Melting Point 203-210° C., MS (ESI+) m/z 411 (M+1).

Example 13

Synthesis of (1E,6E)-1-(4-dimethylamino-2-nitrophenyl)-7-(4-hydroxyphenyl)hepta-1,6-diene-3,5-dione (CU194)

The title compound was synthesized using the same procedure employed for Example 1, but with 4-dimethylamino-2-nitrobenzaldehyde (21 mg, 0.11 mmol) instead of 2-chloro-4-hydroxybenzaldehyde (17 mg, 0.11 mmol). The product was obtained as a solid (8.4 mg, 26%) having the following characteristics.

$^1$H NMR ($\delta$, acetone-$d_6$): 3.12 (s, 6H), 5.99 (s, 1H), 6.68 (d, J=16 Hz, 1H), 6.71 (d, J=16 Hz, 1H), 6.90 (d, J=8.7 Hz, 2H), 7.04 (dd, J=2.4, 8.7 Hz, 1H), 7.15 (d, J=2.4 Hz, 1H), 7.57 (d, J=8.7 Hz, 2H), 7.62 (d, J=16 Hz, 1H), 7.81 (d, J=16 Hz, 1H), 7.82 (d, J=8.7 Hz, 1H), 8.9 (br s, OH).

Melting Point 217-222° C., MS (ESI+) m/z 381 (M+1).

Example 14

Synthesis of (1E,6E)-1-(2-chloro-4-dimethylaminophenyl)-7-(4-hydroxyphenyl)hepta-1,6-diene-3,5-dione (CU195)

The title compound was synthesized using the same procedure employed for Example 1, but with 2-chloro-4-dimethylaminobenzaldehyde (20 mg, 0.11 mmol) instead of 2-chloro-4-hydroxybenzaldehyde (17 mg, 0.11 mmol). The product was obtained as a solid (3.8 mg, 12%) having the following characteristics.

$^1$H NMR ($\delta$, acetone-$d_6$): 3.06 (s, 6H), 5.96 (s, 1H), 6.65 (d, J=16 Hz, 1H), 6.67 (d, J=16 Hz, 1H), 6.73~6.78 (m, 2H), 6.90 (d, J=8.7 Hz, 2H), 7.57 (d, J=8.7 Hz, 2H), 7.60 (d, J=16 Hz, 1H), 7.75 (d, J=9.7 Hz, 1H), 8.00 (d, J=16 Hz, 1H), 8.9 (br s, OH).

Melting Point decomposed at 112° C., MS (ESI+) m/z 370 (M+1), 392 (M+Na).

Example 15

Synthesis of (1E,6E)-1-(2-chloro-4-dimethylaminophenyl)-7-(4-hydroxy-3-methyoxyphenyl)hepta-1,6-diene-3,5-dione (CU196)

The title compound was synthesized using the same procedure employed for Example 2, but with 2-chloro-4-dimethylaminobenzaldehyde (20 mg, 0.11 mmol) instead of 2-chloro-4-hydroxybenzaldehyde (17 mg, 0.11 mmol). The product was obtained as a solid (4.4 mg, 13%) having the following characteristics.

$^1$H NMR ($\delta$, acetone-$d_6$): 3.06 (s, 6H), 3.92 (s, 3H), 5.95 (s, 1H), 6.64 (d, J=16 Hz, 1H), 6.71 (d, J=16 Hz, 1H), 6.73~6.78 (m, 2H), 6.88 (d, J=8.2 Hz, 1H), 7.18 (dd, J=1.9, 8.2 Hz, 1H), 7.34 (d, J=1.9 Hz, 1H), 7.59 (d, J=16 Hz, 1H), 7.74 (d, J=9.7 Hz, 1H), 7.99 (d, J=16 Hz, 1H), 8.1 (br s, OH).

Melting Point 113-120° C., MS (ESI+) m/z 400 (M+1).

Example 16

Synthesis of (1E,6E)-1-(4-dimethylamino-2-nitrophenyl)-7-(3-hydroxy-4-methyoxyphenyl)hepta-1,6-diene-3,5-dione (CU197)

The title compound was synthesized using the same procedure employed for Example 3, but with 4-dimethylamino-2-nitrobenzaldehyde (21 mg, 0.11 mmol) instead of 2-chloro-4-hydroxybenzaldehyde (17 mg, 0.11 mmol). The product was obtained as a solid (7.0 mg, 20%) having the following characteristics.

$^1$H NMR ($\delta$, acetone-$d_6$): 3.13 (s, 6H), 3.89 (s, 3H), 6.01 (s, 1H), 6.69 (d, J=16 Hz, 1H), 6.72 (d, J=16 Hz, 1H), 7.00 (d, J=~2, 8.7 Hz, 1H), 7.05 (dd, J=~2, 8.7 Hz, 1H), 7.14 (dd, J=~2, 8.7 Hz, 1H), 7.15 (d, J=~2 Hz, 1H), 7.21 (d, J=~2 Hz, 1H), 7.57 (d, J=16 Hz, 1H), 7.8 (br s, OH), 7.81 (d, J=16 Hz, 1H), 7.83 (d, J=8.7 Hz, 1H).

Melting Point 183-186° C., MS (ESI+) m/z 411 (M+1), 433 (M+Na).

Example 17

Synthesis of (1E,6E)-1-(2-chloro-4-dimethylaminophenyl)-7-(3-hydroxy-4-methyoxyphenyl)hepta-1,6-diene-3,5-dione (CU202)

The title compound was synthesized using the same procedure employed for Example 3, but with 2-chloro-4-dimethylaminobenzaldehyde (20 mg, 0.11 mmol) instead of 2-chloro-4-hydroxybenzaldehyde (17 mg, 0.11 mmol). The product was obtained as a solid (12.6 mg, 37%) having the following characteristics.

$^1$H NMR ($\delta$, acetone-$d_6$): 3.06 (s, 6H), 3.89 (s, 3H), 5.97 (s, 1H), 6.65 (d, J=16 Hz, 1H), 6.67 (d, J=16 Hz, 1H), 6.73~6.78 (m, 2H), 6.99 (d, J=8.2 Hz, 1H), 7.14 (dd, J=2.4, 8.2 Hz, 1H), 7.20 (d, J=2.4 Hz, 1H), 7.55 (d, J=16 Hz, 1H), 7.74 (d, J=9.7 Hz, 1H), 7.8 (br s, 1H), 8.00 (d, J=16 Hz, 1H).

Melting Point 160-164° C., MS (ESI+) m/z 400 (M+1), 422 (M+Na).

Example 18

Synthesis of (1E,6E)-1-(2,5-dichlorophenyl)-7-(4-hydroxyphenyl)hepta-1,6-diene-3,5-dione (CU229)

The title compound was synthesized using the same procedure employed for Example 1, but with 2,5-dichlorobenzaldehyde (19 mg, 0.11 mmol) instead of 2-chloro-4-hydroxybenzaldehyde (17 mg, 0.11 mmol). The product was obtained as a solid (11.8 mg, 38%) having the following characteristics.

$^1$H NMR ($\delta$, acetone-$d_6$): 6.11 (s, 1H), 6.73 (d, J=16 Hz, 1H), 6.91 (d, J=8.7 Hz, 2H), 7.01 (d, J=16 Hz, 1H), 7.44 (dd, J=~2, 8 Hz, 1H), 7.55 (d, J=8 Hz, 1H), 7.60 (d, J=8.7 Hz, 2H), 7.68 (d, J=16 Hz, 1H), 7.90 (d, J=16 Hz, 1H), 7.92 (d, J=~2 Hz, 1H).

MS (ESI+) m/z 361 (M+1).

Example 19

Synthesis of (1E,6E)-1,7-bis(2-chloro-4-hydroxyphenyl)hepta-1,6-diene-3,5-dione (CU362)

Acetylacetone (10.3 µL, 100 µmol) and boron trioxide (25 mg, 0.40 mmol) was placed in a 20 mL reaction vessel, and dissolved in 0.45 mL of ethyl acetate. To the stirring solution at 80° C. were added 2-chloro-4-hydroxybenzaldehyde (39 mg, 0.25 mmol) and tri-n-butyl borate (57 µL, 0.21 mmol), successively. After the reaction mixture was stirred for 2 h at the same temperature, n-butylamine (22 µL, 0.22 mmol) was added with additional stirring for 1 h. The reaction mixture was treated with a 1:1 solution (3 mL) of 1N HCl and brine at room temperature, and was stirred at 50° C. for 5 min to 1 h (if necessary, the reaction mixture was neutralized with saturated NaHCO$_3$ aqueous solution). The organic layer was purified directly by silica gel column chromatography (eluting with hexane/ethyl acetate or chloroform/methanol) to obtain the title compound as a solid (13.8 mg, 37%) having the following characteristics.

$^1$H NMR ($\delta$, acetone-$d_6$): 6.04 (s, 1H), 6.77 (d, J=16 Hz, 2H), 6.89 (dd, J=2, 8.7 Hz, 2H), 6.98 (d, J=2 Hz, 2H), 7.79 (d, J=8.7 Hz, 2H), 7.99 (d, J=16 Hz, 2H).

Melting Point 248-254° C., MS (ESI+) m/z 377.0 (M+1).

Example 20

Synthesis of (1E,6E)-1,7-bis(5-hydroxy-2-nitrophenyl)hepta-1,6-diene-3,5-dione (CU381)

The title compound was synthesized using the same procedure employed for Example 19, but with 5-hydroxy-2-nitrobenzaldehyde (42 mg, 0.25 mmol) instead of 2-chloro-4-hydroxybenzaldehyde (39 mg, 0.25 mmol). The product was obtained as a solid (7.8 mg, 20%) having the following characteristics.

$^1$H NMR ($\delta$, acetone-$d_6$): 6.24 (s, 1H), 6.78 (d, J=16 Hz, 2H), 7.07 (dd, J=2.4, 9.2 Hz, 2H), 7.23 (d, J=2 Hz, 2H), 8.09 (d, J=9.2 Hz, 2H), 8.17 (d, J=16 Hz, 2H).

Melting Point 253-262° C., MS (ESI+) m/z 399.1 (M+1), 421.1 (M+Na).

Example 21

Synthesis of (1E,6E)-1,7-bis(4-dimethylamino-2-nitrophenyl)hepta-1,6-diene-3,5-dione (CU411)

The title compound was synthesized using the same procedure employed for Example 19, but with 4-dimethylamino-2-nitrobenzaldehyde (49 mg, 0.25 mmol) instead of 2-chloro-4-hydroxybenzaldehyde (39 mg, 0.25 mmol). The product was obtained as a solid (13.6 mg, 30%) having the following characteristics.

$^1$H NMR ($\delta$, acetone-$d_6$): 3.13 (s, 12H), 6.02 (s, 1H), 6.74 (d, J=16 Hz, 2H), 7.05 (dd, J=3, 9 Hz, 2H), 7.17 (d, J=3 Hz, 2H), 7.82 (d, J=16 Hz, 2H), 7.84 (d, J=9 Hz, 2H).

Melting Point 245-250° C., MS (ESI+) m/z 453.4 (M+1), 475.3 (M+Na).

Example 22

Synthesis of (1E,6E)-1,7-bis(2-chloro-4-dimethylaminophenyl)hepta-1,6-diene-3,5-dione (CU412)

The title compound was synthesized using the same procedure employed for Example 19, but with 2-chloro-4-dimethylaminobenzaldehyde (46 mg, 0.25 mmol) instead of 2-chloro-4-hydroxybenzaldehyde (39 mg, 0.25 mmol). The product was obtained as a solid (18.8 mg, 44%) having the following characteristics.

$^1$H NMR ($\delta$, acetone-$d_6$): 3.06 (s, 12H), 5.94 (s, 1H), 6.66 (d, J=16 Hz, 2H), 6.7~6.8 (m, 4H), 7.75 (d, J=9.7 Hz, 2H), 7.99 (d, J=16 Hz, 2H).

Melting Point 238-241° C., MS (ESI+) m/z 431.3 (M+1).

Example 23

Synthesis of (1E,6E)-1-(5-chloro-2-nitrophenyl)-7-(4-hydroxyphenyl)hepta-1,6-diene-3,5-dione (CU465)

The title compound was synthesized using the same procedure employed for Example 1, but with 5-chloro-2-nitrobenzaldehyde (21 mg, 0.11 mmol) instead of 2-chloro-4-hydroxybenzaldehyde (17 mg, 0.11 mmol). The product was obtained as a solid (16.4 mg, 50%) having the following characteristics.

$^1$H NMR (δ, acetone-$d_6$): 6.14 (s, 1H), 6.74 (d, J=16 Hz, 1H), 6.91 (d, J=8.7 Hz, 2H), 6.98 (d, J=16 Hz, 1H), 7.61 (d, J=8.7 Hz, 2H), 7.69 (dd, J=2.4, 8.7 Hz, 1H), 7.69 (d, J=16 Hz, 1H), 7.94 (d, J=16 Hz, 1H), 7.99 (d, J=2.4 Hz, 1H), 8.12 (d, J=8.7 Hz, 1H).

Melting Point 241-250° C., MS (ESI+) m/z 372.4 (M+1).

Example 24

Synthesis of (1E,6E)-1-(5-bromo-2-fluorophenyl)-7-(4-hydroxyphenyl)hepta-1,6-diene-3,5-dione (CU466)

The title compound was synthesized using the same procedure employed for Example 1, but with 5-bromo-2-fluorobenzaldehyde (24 μL, 0.11 mmol) instead of 2-chloro-4-hydroxybenzaldehyde (17 mg, 0.11 mmol). The product was obtained as a solid (11.4 mg, 33%) having the following characteristics.

$^1$H NMR (δ, acetone-$d_6$): 6.11 (s, 1H), 6.73 (d, J=16 Hz, 1H), 6.91 (d, J=8.7 Hz, 2H), 7.02 (d, J=16 Hz, 1H), 7.22 (dd, J=8.7, 10.6 Hz, 1H), 7.58~7.63 (m, 1H), 7.60 (d, J=8.7 Hz, 2H), 7.66 (d, J=16 Hz, 1H), 7.68 (d, J=16 Hz, 1H), 7.99 (dd, J=2.4, 6.8 Hz, 1H).

Melting Point 177-203° C., MS (ESI+) m/z 389.3 (M+1).

Example 25

Synthesis of (1E,6E)-1-(4-hydroxyphenyl)-7-(2-trifluoromethylphenyl)hepta-1,6-diene-3,5-dione (CU467)

The title compound was synthesized using the same procedure employed for Example 1, but with 2-trifluoromethylbenzaldehyde (20 μL, 0.11 mmol) instead of 2-chloro-4-hydroxybenzaldehyde (17 mg, 0.11 mmol). The product was obtained as a solid (14.8 mg, 47%) having the following characteristics.

$^1$H NMR (δ, acetone-$d_6$): 6.10 (s, 1H), 6.74 (d, J=16 Hz, 1H), 6.91 (d, J=8.7 Hz, 2H), 6.93 (d, J=16 Hz, 1H), 7.60 (d, J=8.7 Hz, 2H), 7.62 (d, J=16 Hz, 1H), 7.68 (d, J=16 Hz, 1H), 7.73 (t, J=8 Hz, 1H), 7.81 (d, J=7.7 Hz, 1H), 7.96 (m, 1H), 8.02 (d, J=8.2 Hz, 1H).

Melting Point 181-185° C., MS (ESI+) m/z 361.4 (M+1).

Example 26

Synthesis of (1E,6E)-1-(2-chloro-5-nitrophenyl)-7-(4-hydroxyphenyl)hepta-1,6-diene-3,5-dione (CU470)

The title compound was synthesized using the same procedure employed for Example 1, but with 2-chloro-5-nitrobenzaldehyde (21 mg, 0.11 mmol) instead of 2-chloro-4-hydroxybenzaldehyde (17 mg, 0.11 mmol). The product was obtained as a solid (14.6 mg, 45%) having the following characteristics.

$^1$H NMR (δ, acetone-$d_6$): 6.20 (s, 1H), 6.75 (d, J=16 Hz, 1H), 6.92 (d, J=8.7 Hz, 2H), 7.19 (d, J=16 Hz, 1H), 7.61 (d, J=8.7 Hz, 2H), 7.71 (d, J=16 Hz, 1H), 7.82 (d, J=8.7 Hz, 1H), 7.95 (d, J=16 Hz, 1H), 8.24 (dd, J=2.9, 8.7 Hz, 1H), 8.68 (d, J=2.9 Hz, 1H).

MS (ESI+) m/z 371.9 (M+1).

Example 27

Synthesis of (1E,6E)-1-(4-bromo-2-fluorophenyl)-7-(4-hydroxyphenyl)hepta-1,6-diene-3,5-dione (CU471)

The title compound was synthesized using the same procedure employed for Example 1, but with 4-bromo-2-fluorobenzaldehyde (23 mg, 0.11 mmol) instead of 2-chloro-4-hydroxybenzaldehyde (17 mg, 0.11 mmol). The product was obtained as a solid (9.0 mg, 26%) having the following characteristics.

$^1$H NMR (δ, acetone-$d_6$): 6.10 (s, 1H), 6.72 (d, J=16 Hz, 1H), 6.91 (d, J=8.7 Hz, 2H), 7.96 (d, J=16 Hz, 1H), 7.46~7.54 (m, 2H), 7.59 (d, J=8.7 Hz, 2H), 7.67 (d, J=16 Hz, 1H), 7.67 (d, J=16 Hz, 1H), 7.77 (dd, J=8, 9 Hz, 1H).

Melting Point 223-232° C., MS (ESI+) m/z 389.2 (M+1).

Example 28

Synthesis of (1E,6E)-1-(biphenyl-2-yl)-7-(4-hydroxyphenyl)hepta-1,6-diene-3,5-dione (CU472)

The title compound was synthesized using the same procedure employed for Example 1, but with 2-phenylbenzaldehyde (20 μL, 0.11 mmol) instead of 2-chloro-4-hydroxybenzaldehyde (17 mg, 0.11 mmol). The product was obtained as a solid (6.6 mg, 20%) having the following characteristics.

$^1$H NMR (δ, acetone-$d_6$): 5.99 (s, 1H), 6.68 (d, J=16 Hz, 1H), 6.82 (d, J=16 Hz, 1H), 6.90 (d, J=8.7 Hz, 2H), 7.34~7.53 (m, 8H), 7.58 (d, J=8.7 Hz, 2H), 7.62 (d, J=16 Hz, 1H), 7.66 (d, J=16 Hz, 1H), 7.77 (dd, J=1.5, 7~8 Hz, 1H).

Melting Point 180-188° C., MS (ESI+) m/z 369.3 (M+1), 391.3 (M+Na).

Example 29

Synthesis of (1E,6E)-1-(2-fluoro-5-trifluoromethylphenyl)-7-(4-hydroxyphenyl)hepta-1,6-diene-3,5-dione (CU473)

The title compound was synthesized using the same procedure employed for Example 1, but with 2-fluoro-5-trifluoromethylbenzaldehyde (22 μL, 0.11 mmol) instead of 2-chloro-4-hydroxybenzaldehyde (17 mg, 0.11 mmol). The product was obtained as a solid (2.6 mg, 8%) having the following characteristics.

$^1$H NMR (δ, acetone-$d_6$): 6.14 (s, 1H), 6.73 (d, J=16 Hz, 1H), 6.92 (d, J=8.7 Hz, 2H), 7.12 (d, J=16 Hz, 1H), 7.48 (dd, J=9, 10 Hz, 1H), 7.60 (d, J=8.7 Hz, 2H), 7.69 (d, J=16 Hz, 1H), 7.74 (d, J=16 Hz, 1H), 7.81 (m, 1H), 8.19 (dd, J=7~8 Hz, 1H).

Melting Point 168-174° C., MS (ESI+) m/z 379.3 (M+1).

Example 30

Synthesis of (1E,6E)-1-(5-benzyloxy-2-nitrophenyl)-7-(4-hydroxyphenyl)hepta-1,6-diene-3,5-dione (CU475)

(1) Synthesis of 5-benzyloxy-2-nitrobenzaldehyde

To a suspension of 5-hydroxy-2-nitrobenzaldehyde (300 mg, 1.80 mmol), potassium carbonate (498 mg, 3.60 mmol), and tetrabutylammonium iodide (66 mg, 0.18 mmol) in 1.8 mL of dry N,N-dimethylformamide was added benzyl bromide (0.32 mL, 2.7 mmol) at 0° C. After being stirred at room temperature until the starting material disappeared (5 h), the reaction mixture was filtered to remove inorganic salts. The filtrate was diluted with diethyl ether, and the solution was washed with water, saturated NaHCO$_3$ aqueous solution, brine, and dried over MgSO$_4$. After filtration, the filtrate was concentrated in vacuo, and the residue was purified by silica gel column chromatography (hexane/ethyl acetate=90/10 to 75/25) to obtain the title compound as a slightly yellow solid (405 mg, 87%).

(2) Synthesis of (1E,6E)-1-(5-benzyloxy-2-nitrophenyl)-7-(4-hydroxyphenyl)hepta-1,6-diene-3,5-dione (CU475)

The title compound was synthesized using the same procedure employed for Example 1, but with 5-benzyloxy-2-nitrobenzaldehyde (29 mg, 11 mmol) instead of 2-chloro-4-hydroxybenzaldehyde (17 mg, 0.11 mmol). The product was obtained as a solid (17.8 mg, 46%) having the following characteristics.
$^1$H NMR (δ, acetone-d$_6$): 5.35 (s, 2H), 6.10 (s, 1H), 6.73 (d, J=16 Hz, 1H), 6.84 (d, J=16 Hz, 1H), 6.91 (d, J=8.7 Hz, 2H), 7.25 (dd, J=2.9, 9.2 Hz, 1H), 7.35~7.48 (m, 4H), 7.55 (d, J=8.2 Hz, 2H), 7.60 (d, J=8.7 Hz, 2H), 7.68 (d, J=16 Hz, 1H), 8.10 (d, J=16 Hz, 1H), 8.14 (d, J=9.2 Hz, 1H).
Melting Point 168-172° C., MS (ESI+) m/z 466.1 (M+Na).

Example 31

Synthesis of (1E,6E)-1-(4-hydroxyphenyl)-7-(2-nitrophenyl)hepta-1,6-diene-3,5-dione (CU477)

The title compound was synthesized using the same procedure employed for Example 1, but with 2-nitrobenzaldehyde (17 mg, 0.11 mmol) instead of 2-chloro-4-hydroxybenzaldehyde (17 mg, 0.11 mmol). The product was obtained as a solid (5.4 mg, 18%) having the following characteristics.
MS (ESI+) m/z 338.3 (M+1).

Example 32

Synthesis of (1E,6E)-1-(4-hydroxyphenyl)-7-[2-(methoxycarbonyl)phenyl]hepta-1,6-diene-3,5-dione (CU478)

The title compound was synthesized using the same procedure employed for Example 1, but with methyl 2-formylbenzoate (19 mg, 0.11 mmol) instead of 2-chloro-4-hydroxybenzaldehyde (17 mg, 0.11 mmol). The product was obtained as a solid (12.4 mg, 40%) having the following characteristics.
$^1$H NMR (δ, acetone-d$_6$): 3.92 (s, 3H), 6.08 (s, 1H), 6.72 (d, J=16 Hz, 1H), 6.75 (d, J=16 Hz, 1H), 6.91 (d, J=8.7 Hz, 2H), 7.52 (dd, J=7, 7.7 Hz, 1H), 7.60 (d, J=8.7 Hz, 2H), 7.64 (dd, J=7, 7.7 Hz, 1H), 7.66 (d, J=16 Hz, 1H), 7.86 (d, J=7.7 Hz, 1H), 7.95 (d, J=7.7 Hz, 1H), 8.42 (d, J=16 Hz, 1H).
Melting Point 145-150° C., MS (ESI+) m/z 351.5 (M+1), 373.4 (M+Na).

Example 33

Synthesis of (1E,6E)-1-(4-hydroxyphenyl)-7-(5-methoxy-2-nitrophenyl)hepta-1,6-diene-3,5-dione (CU481)

(1) Synthesis of 5-methoxy-2-nitrobenzaldehyde

To a solution of 5-hydroxy-2-nitrobenzaldehyde (300 mg, 1.80 mmol) in 3.6 mL of dry N,N-dimethylformamide was added sodium hydride (94 mg, 55%, 2.1 mmol) under nitrogen at 0° C. After the reaction mixture was stirred at room temperature for 30 min, methyl iodide (0.17 mL, 2.7 mmol) was added with additional stirring for 30 min. After the reaction mixture was quenched with saturated NH$_4$Cl aqueous solution at 0° C., the solution was extracted with ether. The extract was washed with saturated NaHCO$_3$ aqueous solution, brine, and dried over MgSO$_4$. After filtration, the filtrate was concentrated in vacuo, and the residue was purified by silica gel column chromatography (hexane/ethyl acetate=80/20 to 70/30) to obtain the title compound as a slightly yellow powder (298 mg, 91%).

(2) Synthesis of (1E,6E)-1-(4-hydroxyphenyl)-7-(5-methoxy-2-nitrophenyl)hepta-1,6-diene-3,5-dione (CU481)

The title compound was synthesized using the same procedure employed for Example 1, but with 5-methoxy-2-nitrobenzaldehyde (21 mg, 0.11 mmol) instead of 2-chloro-4-hydroxybenzaldehyde (17 mg, 0.11 mmol). The product was obtained as a solid (10.4 mg, 32%) having the following characteristics.
$^1$H NMR (δ, acetone-d$_6$): 4.01 (s, 3H), 6.10 (s, 1H), 6.73 (d, J=16 Hz, 1H), 6.84 (d, J=16 Hz, 1H), 6.91 (d, J=8.7 Hz, 2H), 7.17 (dd, J=2.9, 9.2 Hz, 1H), 7.36 (d, J=3 Hz, 1H), 7.60 (d, J=8.7 Hz, 2H), 7.68 (d, J=16 Hz, 1H), 8.10 (d, J=16 Hz, 1H), 8.14 (d, J=9.2 Hz, 1H).
Melting Point 151-155° C., MS (ESI+) m/z 368.5 (M+1), 390.5 (M+Na).

Example 34

Synthesis of (1E,6E)-1-(2-bromophenyl)-7-(4-hydroxyphenyl)hepta-1,6-diene-3,5-dione (CU486)

The title compound was synthesized using the same procedure employed for Example 1, but with 2-bromobenzaldehyde (21 mg, 0.11 mmol) instead of 2-chloro-4-hydroxybenzaldehyde (17 mg, 0.11 mmol). The product was obtained as a solid (22.2 mg, 68%) having the following characteristics.
$^1$H NMR (δ, acetone-d$_6$): 6.09 (s, 1H), 6.72 (d, J=16 Hz, 1H), 6.87 (d, J=16 Hz, 1H), 6.91 (d, J=8.7 Hz, 2H), 7.33 (ddd, J=~2, 7.3, 7~8 Hz, 1H), 7.45 (dd, J=7.3, 7.7 Hz, 1H), 7.60 (d, J=8.7 Hz, 2H), 7.67 (d, J=16 Hz, 1H), 7.70 (dd, J=~2, 7.3 Hz, 1H), 7.88 (dd, J=~2, 7.7 Hz, 1H), 7.98 (d, J=16 Hz, 1H).
Melting Point 155-159° C., MS (ESI+) m/z 371.4 (M+1).

Example 35

Synthesis of (1E,6E)-1-(4-hydroxyphenyl)-7-[5-(4-methoxybenzyloxy)-2-nitrophenyl]hepta-1,6-diene-3,5-dione (CU490)

(1) Synthesis of 5-(4-methoxybenzyloxy)-2-nitrobenzaldehyde

The title compound was synthesized using the same procedure employed for Example 30 (1), but with 4-methoxybenzyl chloride instead of benzyl bromide (silica gel column chromatography: hexane/ethyl acetate=90/10 to 70/30). The product was obtained as a slightly yellow powder (462 mg, 89%).

(2) Synthesis of (1E,6E)-1-(4-hydroxyphenyl)-7-[5-(4-methoxybenzyloxy)-2-nitrophenyl]hepta-1,6-diene-3,5-dione (CU490)

The title compound was synthesized using the same procedure employed for Example 1, but with 5-(4-methoxybenzyloxy)-2-nitrobenzaldehyde (33 mg, 0.11 mmol) instead of 2-chloro-4-hydroxybenzaldehyde (17 mg, 0.11 mmol). The product was obtained as a solid (13.6 mg, 33%) having the following characteristics.

$^1$H NMR ($\delta$, acetone-d$_6$): 3.82 (s, 3H), 5.26 (s, 2H), 6.10 (s, 1H), 6.73 (d, J=16 Hz, 1H), 6.84 (d, J=16 Hz, 1H), 6.91 (d, J=8.7 Hz, 2H), 6.99 (d, J=8.7 Hz, 2H), 7.23 (dd, J=2.9, 8.7 Hz, 1H), 7.44 (d, J=2.9 Hz, 1H), 7.46 (d, J=8.7 Hz, 2H), 7.60 (d, J=8.7 Hz, 2H), 7.68 (d, J=16 Hz, 1H), 8.10 (d, J=16 Hz, 1H), 8.13 (d, J=8.7 Hz, 1H).

MS (ESI+) m/z 496.5 (M+Na).

Example 36

Synthesis of (1E,6E)-1-(4-hydroxyphenyl)-7-[2-nitro-5-(pyridin-3-ylmethoxy)phenyl]hepta-1,6-diene-3,5-dione (CU491)

(1) Synthesis of 2-nitro-5-(pyridin-3-ylmethoxy)benzaldehyde

The title compound was synthesized using the same procedure employed for Example 30 (1), but with 3-(chloromethyl)pyridine hydrochloride instead of benzyl bromide (silica gel column chromatography: hexane/ethyl acetate=60/40 to 30/70). The product was obtained as a slightly yellow powder (49 mg, 11%).

(2) Synthesis of (1E,6E)-1-(4-hydroxyphenyl)-7-[2-nitro-5-(pyridin-3-ylmethoxy)phenyl]hepta-1,6-diene-3,5-dione (CU491)

The title compound was synthesized using the same procedure employed for Example 1, but with 2-nitro-5-(pyridin-3-ylmethoxy)benzaldehyde (30 mg, 0.11 mmol) instead of 2-chloro-4-hydroxybenzaldehyde (17 mg, 0.11 mmol). The product was obtained as a solid (4.8 mg, 12%) having the following characteristics.

$^1$H NMR ($\delta$, acetone-d$_6$): 5.42 (s, 2H), 6.10 (s, 1H), 6.73 (d, J=16 Hz, 1H), 6.86 (d, J=16 Hz, 1H), 6.91 (d, J=8.7 Hz, 2H), 7.29 (dd, J=2.9, 9.2 Hz, 1H), 7.45 (dd, J=5.4, 7.7 Hz, 1H), 7.51 (d, J=3 Hz, 1H), 7.60 (d, J=8.7 Hz, 2H), 7.68 (d, J=16 Hz, 1H), 7.95 (br d, J=8.2 Hz, 1H), 8.10 (d, J=16 Hz, 1H), 8.16 (d, J=9.2 Hz, 1H), 8.60 (dd, J=~2, 5 Hz, 1H), 8.76 (d, J=~2 Hz, 1H).

MS (ESI+) m/z 445.6 (M+1).

Example 37

Synthesis of (1E,6E)-1-[5-(2-chloro-6-fluorobenzyloxy)-2-nitrophenyl]-7-(4-hydroxyphenyl)hepta-1,6-diene-3,5-dione (CU492)

(1) Synthesis of 5-(2-chloro-6-fluorobenzyloxy)-2-nitrobenzaldehyde

The title compound was synthesized using the same procedure employed for Example 30 (1), but with 2-chloro-6-fluorobenzyl chloride instead of benzyl bromide (silica gel column chromatography: hexane/ethyl acetate=90/10 to 70/30). The product was obtained as a slightly yellow powder (487 mg, 87%).

(2) Synthesis of (1E,6E)-1-[5-(2-chloro-6-fluorobenzyloxy)-2-nitrophenyl]-7-(4-hydroxyphenyl)hepta-1,6-diene-3,5-dione (CU492)

The title compound was synthesized using the same procedure employed for Example 1, but with 5-(2-chloro-6-fluorobenzyloxy)-2-nitrobenzaldehyde (35 mg, 0.11 mmol) instead of 2-chloro-4-hydroxybenzaldehyde (17 mg, 0.11 mmol). The product was obtained as a solid (11.2 mg, 26%) having the following characteristics.

$^1$H NMR ($\delta$, acetone-d$_6$): 5.47 (d, J=1.5 Hz, 1H), 6.11 (s, 1H), 6.73 (d, J=16 Hz, 1H), 6.91 (d, J=16 Hz, 1H), 6.91 (d, J=8.7 Hz, 2H), 7.29 (dd, J=9, 10 Hz, 1H), 7.30 (dd, J=2.9, 9.2 Hz, 1H), 7.43 (d, J=8.2 Hz, 1H), (m, 1H), 7.53 (d, J=2.9 Hz, 1H), 7.60 (d, J=8.7 Hz, 2H), 7.68 (d, J=16 Hz, 1H), 8.11 (d, J=16 Hz, 1H), 8.17 (d, J=9.2 Hz, 1H).

Melting Point 180-183° C., MS (ESI+) m/z 496.5 (M+1), 518.5 (M+Na).

Example 38

Synthesis of (1E,6E)-1-[5-(2,4-dichlorobenzyloxy)-2-nitrophenyl]-7-(4-hydroxyphenyl)hepta-1,6-diene-3,5-dione (CU493)

(1) Synthesis of 5-(2,4-dichlorobenzyloxy)-2-nitrobenzaldehyde

The title compound was synthesized using the same procedure employed for Example 30 (1), but with 2,4-dichlorobenzyl chloride instead of benzyl bromide (purified by recrystallization (hexane/ethyl acetate) instead of silica gel column chromatography). The product was obtained as a slightly yellow powder (289 mg, 49%).

(2) Synthesis of (1E,6E)-1-[5-(2,4-dichlorobenzyloxy)-2-nitrophenyl]-7-(4-hydroxyphenyl)hepta-1,6-diene-3,5-dione (CU493)

The title compound was synthesized using the same procedure employed for Example 1, but with 5-(2,4-dichlorobenzyloxy)-2-nitrobenzaldehyde (37 mg, 0.11 mmol) instead of 2-chloro-4-hydroxybenzaldehyde (17 mg, 0.11 mmol). The product was obtained as a solid (18.4 mg, 41%) having the following characteristics.

$^1$H NMR ($\delta$, acetone-d$_6$): 5.42 (s, 1H), 6.10 (s, 1H), 6.72 (d, J=16 Hz, 1H), 6.87 (d, J=16 Hz, 1H), 6.91 (d, J=8.7 Hz, 2H), 7.29 (dd, J=2.4, 9.2 Hz, 1H), 7.48 (dd, J=1.9, 8.2 Hz, 1H), 7.52 (d, J=2.4 Hz, 1H), 7.59 (d, J=8.7 Hz, 2H), 7.61 (d, J=1.9 Hz, 1H), 7.68 (d, J=16 Hz, 1H), 7.72 (d, J=8.2 Hz, 1H), 8.10 (d, J=16 Hz, 1H), 8.16 (d, J=9.2 Hz, 1H).

Melting Point 157-161° C., MS (ESI+) m/z 512.3 (M+1), 534.4 (M+Na).

Example 39

Synthesis of (1E,6E)-1-[5-(4-tert-butylbenzyloxy)-2-nitrophenyl]-7-(4-hydroxyphenyl)hepta-1,6-diene-3,5-dione (CU494)

(1) Synthesis of 5-(4-tert-butylbenzyloxy)-2-nitrobenzaldehyde

The title compound was synthesized using the same procedure employed for Example 30 (1), but with 4-tert-butylbenzyl chloride instead of benzyl bromide (silica gel column chromatography: hexane/ethyl acetate=90/10). The product was obtained as a slightly yellow oil (476 mg, 84%).

(2) Synthesis of (1E,6E)-1-[5-(4-tert-butylbenzyloxy)-2-nitrophenyl]-7-(4-hydroxyphenyl)hepta-1,6-diene-3,5-dione (CU494)

The title compound was synthesized using the same procedure employed for Example 1, but with 5-(4-tert-butylbenzyloxy)-2-nitrobenzaldehyde (36 mg, 0.11 mmol) instead of 2-chloro-4-hydroxybenzaldehyde (17 mg, 0.11 mmol). The product was obtained as a solid (26.0 mg, 59%) having the following characteristics.

$^1$H NMR (δ, acetone-$d_6$): 1.33 (s, 9H), 5.31 (s, 1H), 6.10 (s, 1H), 6.73 (d, J=16 Hz, 1H), 6.84 (d, J=16 Hz, 1H), 6.91 (d, J=8.7 Hz, 2H), 7.24 (dd, J=2.4, 9.2 Hz, 1H), 7.44~7.5 (m, 5H), 7.60 (d, J=8.7 Hz, 2H), 7.68 (d, J=16 Hz, 1H), 8.11 (d, J=16 Hz, 1H), 8.14 (d, J=9.2 Hz, 1H).

MS (ESI+) m/z 500.6 (M+1), 522.6 (M+Na).

Example 40

Synthesis of (E)-1-(2-chloro-4-hydroxyphenyl)-7-(4-hydroxyphenyl)hept-1-ene-3,5-dione (CU522)

(1) Synthesis of 6-(4-hydroxyphenyl)hexane-2,4-dione

To a solution of 6-(4-hydroxyphenyl)hex-5-ene-2,4-dione (1.00 g, 4.90 mmol) in 50 mL of ethyl acetate was added palladium 5% on carbon (200 mg) under nitrogen. After the vessel was purged with hydrogen, the reaction mixture was stirred under 1 atm of hydrogen at room temperature for 12 h. After the vessel was purged with nitrogen, the reaction mixture was filtered to remove palladium 5% on carbon. The filtrate was concentrated in vacuo, and the residue was purified by silica gel column chromatography (hexane/ethyl acetate=70/30 to 60/40) to obtain the title compound as a colorless oil (802 mg, 80%) having the following characteristics.

$^1$H NMR (δ, acetone-$d_6$): 2.00 (s, 3H×0.7), 2.14 (s, 3H×0.3), 2.56 (t, J=7.7 Hz, 2H×0.7), 2.74~2.84 (m, 2H+2H×0.3), 3.65 (2H×0.3), 5.64 (s, 1H×0.7), 6.73 (d, J=8.7 Hz, 2H×0.3), 6.74 (d, J=8.7 Hz, 2H×0.7), 7.03 (d, J=8.7 Hz, 2H×0.3), 7.05 (d, =8.7 Hz, 2H×0.7), 8.1 (br s, 1H, OH).

MS (ESI+) m/z 207.3 (M+1).

(2) Synthesis of (E)-1-(2-chloro-4-hydroxyphenyl)-7-(4-hydroxyphenyl)hept-1-ene-3,5-dione (CU522)

6-(4-Hydroxyphenyl)hexane-2,4-dione (18 mg, 87 μmol) and boron trioxide (22 mg, 0.32 mmol) was placed in a 20 mL reaction vessel, and dissolved in 0.4 mL of ethyl acetate. To the stirring solution at 80° C. were added 2-chloro-4-hydroxybenzaldehyde (12 mg, 78 μmol) and tri-n-butyl borate (50 μL, 0.19 mmol). After the reaction mixture was stirred for 2 h at the same temperature, n-butylamine (19 μL, 0.19 mmol) was added with additional stirring for 1 h. The reaction mixture was treated with a 1:1 solution (1 mL) of 1N HCl and brine, and was stirred at 50° C. for 5 min to 1 h (if necessary, the reaction mixture was neutralized by saturated $NaHCO_3$ aqueous solution). The organic layer was purified directly by silica gel column chromatography (eluting with hexane/ethyl acetate or chloroform/methanol) to obtain the title compound as a solid (9.2 mg, 34%) having the following characteristics.

$^1$H NMR (δ, acetone-$d_6$): 2.70 (t, J=8 Hz, 2H), 2.86 (t, J=8 Hz, 2H), 5.82 (s, 1H), 6.61 (d, J=16 Hz, 1H), 6.75 (d, J=8.7 Hz, 2H), 6.87 (d, J=2.4, 8.7 Hz, 1H), 6.96 (d, J=2.4 Hz, 1H), 7.07 (d, J=8.7 Hz, 2H), 7.74 (d, J=8.7 Hz, 1H), 7.89 (d, J=16 Hz, 1H).

MS (ESI+) m/z 345.4 (M+1), 367.4 (M+Na).

Example 41

Synthesis of (E)-1-(4-dimethylamino-2-nitrophenyl)-7-(4-hydroxyphenyl)hept-1-ene-3,5-dione (CU523)

The title compound was synthesized using the same procedure employed for Example 40 (2), but with 4-dimethylamino-2-nitrobenzaldehyde (15 mg, 78 μmol) instead of 2-chloro-4-hydroxybenzaldehyde (12 mg, 78 μmol). The product was obtained as a solid (12.2 mg, 41%) having the following characteristics.

$^1$H NMR (δ, acetone-$d_6$): 2.68 (t, J=8 Hz, 2H), 2.86 (t, J=8 Hz, 2H), 3.12 (s, 6H), 5.81 (s, 1H), 6.58 (d, J=16 Hz, 1H), 6.74 (d, J=8.7 Hz, 2H), 7.04 (d, J=2.4, 9.2 Hz, 1H), 7.07 (d, J=8.7 Hz, 2H), 7.15 (d, J=2.4 Hz, 1H), 7.75 (d, J=16 Hz, 1H), 7.79 (d, J=9.2 Hz, 1H), 8.1 (br s, 1H, OH).

Melting Point 136-142° C., MS (ESI+) m/z 383.5 (M+1), 405.4 (M+Na).

Example 42

Synthesis of (E)-1-(2-chloro-4-dimethylaminophenyl)-7-(4-hydroxyphenyl)hept-1-ent-3,5-dione (CU524)

The title compound was synthesized using the same procedure employed for Example 40 (2), but with 2-chloro-4-dimethylaminobenzaldehyde (14 mg, 78 μmol) instead of 2-chloro-4-hydroxybenzaldehyde (12 mg, 78 μmol). The product was obtained as a solid (15.6 mg, 54%) having the following characteristics.

$^1$H NMR (δ, acetone-$d_6$): 2.66 (t, J=8 Hz, 2H), 2.86 (t, J=8 Hz, 2H), 3.05 (s, 6H), 5.77 (s, 1H), 6.52 (d, J=16 Hz, 1H), 6.7~6.76 (m, 4H), 7.07 (d, J=8.7 Hz, 2H), 7.70 (d, J=9.7 Hz, 1H), 7.93 (d, J=16 Hz, 1H), 8.1 (br s, 1H, OH).

Melting Point 120-129° C., MS (ESI+) m/z 372.5 (M+1).

Example 43

Synthesis of (E)-1-(biphenyl-2-yl)-7-(4-hydroxyphenyl)hept-1-ene-3,5-dione (CU525)

The title compound was synthesized using the same procedure employed for Example 40 (2), but with 2-phenylbenzaldehyde (15 μL, 78 μmol) instead of 2-chloro-4-hydroxybenzaldehyde (12 mg, 78 μmol). The product was obtained as a solid (13.8 mg, 48%) having the following characteristics.

$^1$H NMR (δ, acetone-$d_6$): 2.68 (t, J=8 Hz, 2H), 2.84 (t, J=8 Hz, 2H), 5.81 (s, 1H), 6.68 (d, J=16 Hz, 1H), 6.74 (d, J=8.7 Hz, 2H), 7.06 (d, J=8.7 Hz, 2H), 7.32~7.52 (m, 8H), 7.59 (d, J=16 Hz, 1H), 7.86 (dd, J=1.5, 7.3 Hz, 1H), 8.1 (br s, 1H, OH).

MS (ESI+) m/z 371.5 (M+1), 393.5 (M+Na).

Example 44

Synthesis of (1E,6E)-1-(4-hydroxybiphenyl-2-yl)-7-(4-hydroxyphenyl)hepta-1,6-diene-3,5-dione (CU526)

(1) Synthesis of 4-hydroxybiphenyl-2-carboxyaldehyde

To a suspension of 2-bromo-5-hydroxybenzaldehyde (300 mg, 1.49 mmol), sodium carbonate (190 mg, 1.79 mmol), and phenylboronic acid (272 mg, 2.23 mmol) in 3.0 mL of N,N-dimethylformamide/water (2:1) was added palladium acetate (17 mg, 76 μmol) under nitrogen. After being stirred at room temperature overnight, the reaction mixture was filtered. The filtrate was diluted with diethyl ether, and the solution was washed with brine, and dried over $MgSO_4$. After filtration, the filtrate was concentrated in vacuo, and the residue was purified by silica gel column chromatography (hexane/ethyl acetate=80/20 to 70/30) to obtain the title compound as a slightly yellow powder (242 mg, 82%).

(2) Synthesis of (1E,6E)-1-(4-hydroxybiphenyl-2-yl)-7-(4-hydroxyphenyl)hepta-1,6-diene-3,5-dione (CU526)

The title compound was synthesized using the same procedure employed for Example 1, but with 4-hydroxybiphenyl-2-carboxyaldehyde (23 mg, 0.11 mmol) instead of 2-chloro-4-hydroxybenzaldehyde (17 mg, 0.11 mmol). The product was obtained as a solid (15.8 mg, 47%) having the following characteristics.

$^1$H NMR (δ, acetone-d$_6$): 5.98 (s, 1H), 6.67 (d, J=16 Hz, 1H), 6.73 (d, J=16 Hz, 1H), 6.90 (d, J=8.7 Hz, 2H), 6.99 (dd, J=2.4, 8.2 Hz, 1H), 7.24 (d, J=8.2 Hz, 1H), 7.28~7.34 (m, 3H), 7.39 (dd, J=7, 8 Hz, 1H), 7.46 (dd, J=7, 8 Hz, 2H), 7.57 (d, J=8.7 Hz, 2H), 7.61 (d, J=16 Hz, 1H), 7.62 (d, J=16 Hz, 1H).

Melting Point 179-186° C., MS (ESI+) m/z 385.4 (M+1), 407.4 (M+Na).

Example 45

Synthesis of (1E,6E)-1-(4-benzyloxybiphenyl-2-yl)-7-(4-hydroxyphenyl)hepta-1,6-diene-3,5-dione (CU527)

(1) Synthesis of 4-benzyloxybiphenyl-2-carboxyaldehyde

To a suspension of 4-hydroxybiphenyl-2-carboxyaldehyde (80 mg, 0.40 mmol), potassium carbonate (111 mg, 0.80 mmol), and tetrabutylammonium iodide (15 mg, 0.04 mmol) in 0.8 mL of dry N,N-dimethylformamide was added benzyl bromide (72 μL, 0.60 mmol) at 0° C. After being stirred at room temperature overnight, the reaction mixture was diluted with diethyl ether. The solution was washed with water, saturated NaHCO$_3$ aqueous solution, brine, and dried over MgSO$_4$. After filtration, the filtrate was concentrated in vacuo, and the residue was purified by silica gel column chromatography (hexane/ethyl acetate=95/5 to 80/20) to obtain the title compound as a white crystal (112 mg, 77%).

(2) Synthesis of (1E,6E)-1-(4-benzyloxybiphenyl-2-yl)-7-(4-hydroxyphenyl)hepta-1,6-diene-3,5-dione (CU527)

The title compound was synthesized using the same procedure employed for Example 1, but with 4-benzyloxybiphenyl-2-carboxyaldehyde (33 mg, 0.11 mmol) instead of 2-chloro-4-hydroxybenzaldehyde (17 mg, 0.11 mmol). The product was obtained as a solid (22.6 mg, 54%) having the following characteristics.

$^1$H NMR (δ, acetone-d$_6$): 5.26 (s, 2H), 5.97 (s, 1H), 6.67 (d, J=16 Hz, 1H), 6.85 (d, J=16 Hz, 1H), 6.90 (d, J=8.7 Hz, 2H), 7.16 (dd, J=2.4, 8.7 Hz, 1H), 7.3~7.5 (m, 8H), 7.44 (d, J=8.7 Hz, 1H), 7.51~7.59 (m, 3H), 7.55 (d, J=8.7 Hz, 2H), 7.62 (d, J=16 Hz, 1H), 7.64 (d, J=16 Hz, 1H).

Melting Point 172-178° C., MS (ESI+) m/z 475.5 (M+1), 497.4 (M+Na).

Example 46

Synthesis of (1E,6E)-1-(4-hydroxyphenyl)-7-[2-(naphthalen-1-yl)phenyl]hepta-1,6-diene-3,5-dione (CU528)

(1) Synthesis of 2-(naphthalen-1-yl)benzaldehyde

To a suspension of 2-bromobenzaldehyde (200 μL, 1.71 mmol), sodium carbonate (218 mg, 2.06 mmol), and 1-naphthaleneboronic acid (353 mg, 2.05 mmol) in 3.4 mL of N,N-dimethylformamide/water (2:1) was added palladium acetate (20 mg, 89 μmol) under nitrogen. After being stirred at room temperature overnight, the reaction mixture was filtered. The filtrate was diluted with diethyl ether, and the solution was washed with saturated NaHCO$_3$ aqueous solution, brine, and dried over MgSO$_4$. After filtration, the filtrate was concentrated in vacuo, and the residue was purified by silica gel column chromatography (hexane/ethyl acetate=90/10 to 80/20) to obtain the title compound as a white solid (346 mg, 87%).

(2) Synthesis of (1E,6E)-1-(4-hydroxyphenyl)-7-[2-(naphthalen-1-yl)phenyl]hepta-1,6-diene-3,5-dione (CU528)

The title compound was synthesized using the same procedure employed for Example 1, but with 2-(naphthalen-1-yl)benzaldehyde (27 mg, 0.11 mmol) instead of 2-chloro-4-hydroxybenzaldehyde (17 mg, 0.11 mmol). The product was obtained as a solid (17.0 mg, 46%) having the following characteristics.

$^1$H NMR (δ, acetone-d$_6$): 5.86 (s, 1H), 6.60 (d, J=16 Hz, 1H), 6.79 (d, J=16 Hz, 1H), 6.88 (d, J=8.7 Hz, 2H), 7.26 (d, J=16 Hz, 1H), 7.36~7.46 (m, 4H), 7.5~7.6 (m, 6H), 7.62 (dd, J=7, 9 Hz, 1H), 8.0~8.05 (m, 3H).

Melting Point 95-101° C., MS (ESI+) m/z 419.4 (M+1), 441.4 (M+Na).

Example 47

Synthesis of (1E,6E)-1-(4-hydroxyphenyl)-7-[2-(naphthalen-2-yl)phenyl]hepta-1,6-diene-3,5-dione (CU529)

(1) Synthesis of 2-(naphthalen-2-yl)benzaldehyde

The title compound was synthesized using the same procedure employed for Example 46 (1), but with 2-naphthaleneboronic acid instead of 1-naphthaleneboronic acid. The product was obtained as a colorless oil (192 mg, 48%).

(2) Synthesis of (1E,6E)-1-(4-hydroxyphenyl)-7-[2-(naphthalen-2-yl)phenyl]hepta-1,6-diene-3,5-dione (CU529)

The title compound was synthesized using the same procedure employed for Example 1, but with 2-(naphthalen-2-yl)benzaldehyde (27 mg, 0.11 mmol) instead of 2-chloro-4-hydroxybenzaldehyde (17 mg, 0.11 mmol). The product was obtained as a solid (15.8 mg, 43%) having the following characteristics.

$^1$H NMR (δ, acetone-d$_6$): 5.99 (s, 1H), 6.65 (d, J=16 Hz, 1H), 6.85 (d, J=16 Hz, 1H), 6.89 (d, J=8.7 Hz, 2H), 7.46~7.62 (m, 9H), 7.71 (d, J=16 Hz, 1H), 7.89 (s, 1H), 7.95 (d, J=7.2 Hz, 1H), 7.96~8.02 (m, 2H), 8.03 (d, J=8.2 Hz, 1H).

Melting Point 105-114° C., MS (ESI+) m/z 441.4 (M+Na).

Example 48

Synthesis of (E)-1-(5-hydroxy-2-nitrophenyl)-7-(4-hydroxyphenyl)hept-1-ene-3,5-dione (CU530)

The title compound was synthesized using the same procedure employed for Example 40 (2), but with 5-hydroxy-2-nitrobenzaldehyde (13 mg, 78 μmol) instead of 2-chloro-4- hydroxybenzaldehyde (12 mg, 78 μmol). The product was obtained as a solid (6.0 mg, 22%) having the following characteristics.

$^1$H NMR (δ, acetone-d$_6$): 2.74 (t, J=8 Hz, 2H), 2.87 (t, J=8 Hz, 2H), 5.91 (s, 1H), 6.60 (d, J=16 Hz, 1H), 6.75 (d, J=8.7 Hz, 2H), 7.03 (dd, J=2, 8.7 Hz, 1H), 7.08 (d, J=8.7 Hz, 2H), 7.17 (d, J=2 Hz, 1H), 8.04 (d, J=16 Hz, 1H), 8.06 (d, J=8.7 Hz, 1H).

Melting Point 62-70° C., MS (ESI+) m/z 356.4 (M+1), 378.4 (M+Na).

Example 49

Synthesis of (1E,6E)-1-(5-benzyloxy-2-bromophenyl)-7-(4-hydroxyphenyl)hepta-1,6-diene-3,5-dione (CU531)

(1) Synthesis of 5-benzyloxy-2-bromobenzaldehyde

To a suspension of 2-bromo-5-hydroxybenzaldehyde (100 mg, 0.50 mmol), potassium carbonate (138 mg, 1.00 mmol), and tetrabutylammonium iodide (18 mg, 0.05 mmol) in 1.0 mL of dry N,N-dimethylformamide was added benzyl bromide (89 μL, 0.74 mmol) at 0° C. After being stirred at room temperature overnight, the reaction mixture was diluted with diethyl ether. The solution was washed with water, saturated NaHCO$_3$ aqueous solution, brine, and dried over MgSO$_4$. After filtration, the filtrate was concentrated in vacuo, and the residue was purified by silica gel column chromatography (hexane/ethyl acetate=95/5 to 80/20) to obtain the title compound as a colorless oil (140 mg, 97%).

(2) Synthesis of (1E,6E)-1-(5-benzyloxy-2-bromophenyl)-7-(4-hydroxyphenyl)hepta-1,6-diene-3,5-dione (CU531)

The title compound was synthesized using the same procedure employed for Example 1, but with 5-benzyloxy-2-bromobenzaldehyde (33 mg, 0.11 mmol) instead of 2-chloro-4-hydroxybenzaldehyde (17 mg, 0.11 mmol). The product was obtained as a solid (4.2 mg, 10%) having the following characteristics.

MS (ESI+) m/z 377.4 (M+1).

Example 50

Synthesis of (1E,6E)-1-(2-bromo-5-hydroxyphenyl)-7-(4-hydroxyphenyl)hepta-1,6-diene-3,5-dione (CU532)

The title compound was synthesized using the same procedure employed for Example 1, but with 2-bromo-5-hydroxybenzaldehyde (23 mg, 0.11 mmol, prepared according to the procedure described in Synthetic Communications, (2007), 37, 579) instead of 2-chloro-4-hydroxybenzaldehyde (17 mg, 0.11 mmol). The product was obtained as a solid (25.6 mg, 75%) having the following characteristics.

$^1$H NMR (δ, acetone-d$_6$): 6.08 (s, 1H), 6.72 (d, J=16 Hz, 1H), 6.77 (d, J=16 Hz, 1H), 6.86 (d, J=8.7 Hz, 1H), 6.91 (d, J=8.7 Hz, 2H), 7.31 (br s, 1H), 7.49 (d, J=8.7 Hz, 1H), 7.60 (d, J=8.7 Hz, 2H), 7.67 (d, J=16 Hz, 1H), 7.90 (d, J=16 Hz, 1H).

Melting Point 182-186° C., MS (ESI+) m/z 387.4 (M+1).

Example 51

Synthesis of (1E,6E)-1-[5-hydroxy-2-(naphthalen-1-yl)phenyl]-7-(4-hydroxyphenyl)hepta-1,6-diene-3,5-dione (CU538)

(1) Synthesis of 5-hydroxy-2-(naphthalen-1-yl)benzaldehyde

To a suspension of 2-bromo-5-hydroxybenzaldehyde (300 mg, 1.49 mmol), sodium carbonate (190 mg, 1.79 mmol), and 1-naphthaleneboronic acid (384 mg, 2.23 mmol) in 3.0 mL of N,N-dimethylformamide/water (2:1) was added palladium acetate (18 mg, 80 μmol) under nitrogen. After being stirred at room temperature overnight, the reaction mixture was filtered. The filtrate was diluted with ethyl acetate, and the solution was washed with saturated NaHCO$_3$ aqueous solution, brine, and dried over MgSO$_4$. After filtration, the filtrate was concentrated in vacuo, and the residue was purified by silica gel column chromatography (hexane/ethyl acetate=85/15 to 75/25) to obtain the title compound as a white solid (274 mg, 74%).

(2) Synthesis of (1E,6E)-1-[5-hydroxy-2-(naphthalen-1-yl)phenyl]-7-(4-hydroxyphenyl)hepta-1,6-diene-3,5-dione (CU538)

The title compound was synthesized using the same procedure employed for Example 1, but with 5-hydroxy-2-(naphthalen-1-yl)benzaldehyde (28 mg, 0.11 mmol) instead of 2-chloro-4-hydroxybenzaldehyde (17 mg, 0.11 mmol). The product was obtained as a solid (26.2 mg, 69%) having the following characteristics.

$^1$H NMR (δ, acetone-d$_6$): 5.85 (s, 1H), 6.59 (d, J=16 Hz, 1H), 6.69 (d, J=16 Hz, 1H), 6.88 (d, J=8.7 Hz, 2H), 7.06 (d, J=2.4, 8.2 Hz, 1H), 7.20 (d, J=8.2 Hz, 1H), 7.21 (d, J=16 Hz, 1H), 7.35 (d, J=6.8 Hz, 1H), 7.4~7.61 (m, 8H), 7.98 (d, J=8.2 Hz, 1H), 7.99 (d, J=8.2 Hz, 1H), 8.8 (br s, 1H, OH).

Melting Point 215-221° C., MS (ESI+) m/z 435.4 (M+1), 457.4 (M+Na).

Example 52

Synthesis of (1E,6E)-1-(2-bromo-4-hydroxy-5-methoxyphenyl)-7-(4-hydroxyphenyl)hepta-1,6-diene-3,5-dione (CU539)

The title compound was synthesized using the same procedure employed for Example 1, but with 2-bromo-4-hydroxy-5-methoxybenzaldehyde (26 mg, 0.11 mmol, prepared according to the procedure described in J. Org. Chem., (2002), 67, 6493) instead of 2-chloro-4-hydroxybenzaldehyde (17 mg, 0.11 mmol). The product was obtained as a solid (24.2 mg, 66%) having the following characteristics.

$^1$H NMR (δ, acetone-d$_6$): 3.94 (s, 3H), 5.99 (s, 1H), 6.68 (d, J=16 Hz, 1H), 6.79 (d, J=16 Hz, 1H), 6.91 (d, J=8.7 Hz, 2H), 7.13 (s, 1H), 7.48 (s, 1H), 7.57 (d, J=8.7 Hz, 2H), 7.63 (d, J=16 Hz, 1H), 7.93 (d, J=16 Hz, 1H).

Melting Point 237-242° C., MS (ESI+) m/z 417.3 (M+1), 439.3 (M+Na).

Example 53

Synthesis of (E)-1-(4-hydroxybiphenyl-2-yl)-7-(4-hydroxyphenyl)hept-1-ene-3,5-dione (CU541)

The title compound was synthesized using the same procedure employed for Example 40 (2), but with 4-hydroxybiphenyl-2-carboxyaldehyde (16 mg, 78 μmol) instead of 2-chloro-4-hydroxybenzaldehyde (12 mg, 78 μmol). The product was obtained as a solid (15.0 mg, 50%) having the following characteristics.

$^1$H NMR (δ, acetone-$d_6$): 2.68 (t, J=8 Hz, 2H), 2.84 (t, J=8 Hz, 2H), 5.81 (s, 1H), 6.59 (d, J=16 Hz, 1H), 6.74 (d, J=8.2 Hz, 2H), 6.98 (dd, J=2.9, 8.2 Hz, 1H), 7.06 (d, J=8.2 Hz, 2H), 7.23 (d, J=8.2 Hz, 1H), 7.28 (d, J=2.9 Hz, 1H), 7.29 (d, J=7 Hz, 2H), 7.38 (t, J=7 Hz, 1H), 7.45 (dd, J=7, 7 Hz, 2H), 7.55 (d, J=16 Hz, 1H).

Melting Point 148-158° C., MS (ESI+) m/z 387.4 (M+1), 409.4 (M+Na).

Example 54

Synthesis of (E)-1-[5-hydroxy-2-(naphthalen-1-yl) phenyl]-7-(4-hydroxyphenyl)hept-1-ene-3,5-dione (CU542)

The title compound was synthesized using the same procedure employed for Example 40 (2), but with 5-hydroxy-2-(naphthalen-1-yl)benzaldehyde (20 mg, 78 μmol) instead of 2-chloro-4-hydroxybenzaldehyde (12 mg, 78 μmol). The product was obtained as a solid (17.2 mg, 51%) having the following characteristics.

$^1$H NMR (δ, acetone-$d_6$): 2.60 (t, J=8 Hz, 2H), 2.77 (t, J=8 Hz, 2H), 5.68 (s, 1H), 6.56 (d, J=16 Hz, 1H), 6.72 (d, J=8.2 Hz, 2H), 7.01 (d, J=8.2 Hz, 2H), 7.04 (dd, J=2.4, 8.2 Hz, 1H), 7.14 (d, J=16 Hz, 1H), 7.19 (d, J=8.2 Hz, 1H), 7.34 (d, J=6.8 Hz, 1H), 7.40 (d, J=2.4 Hz, 1H), 7.4~7.54 (m, 3H), 7.58 (dd, J=7.2, 8.2 Hz, 1H), 7.97 (d, J=8.2 Hz, 1H), 7.98 (d, J=8.2 Hz, 1H).

Melting Point 138-142° C., MS (ESI+) m/z 437.4 (M+1), 459.5 (M+Na).

Example 55

Synthesis of (1E,6E)-1-(2-bromo-5-hydroxy-4-methoxyphenyl)-7-(4-hydroxyphenyl)hepta-1,6-diene-3,5-dione (CU543)

The title compound was synthesized using the same procedure employed for Example 1, but with 2-bromo-5-hydroxy-4-methoxybenzaldehyde (26 mg, 0.11 mmol, prepared according to the procedure described in Zhejiang Daxue Xuebao, Gongxueban, (2006), 40, 520) instead of 2-chloro-4-hydroxybenzaldehyde (17 mg, 0.11 mmol). The product was obtained as a solid (13.2 mg, 36%) having the following characteristics.

$^1$H NMR (δ, acetone-$d_6$): 3.93 (s, 3H), 6.04 (s, 1H), 6.71 (d, J=16 Hz, 1H), 6.72 (d, J=16 Hz, 1H), 6.91 (d, J=8.7 Hz, 2H), 7.21 (s, 1H), 7.35 (s, 1H), 7.59 (d, J=8.7 Hz, 2H), 7.64 (d, J=16 Hz, 1H), 7.90 (d, J=16 Hz, 1H).

Melting Point 224-229° C., MS (ESI+) m/z 417.3 (M+1).

Example 56

Synthesis of (1E,6E)-1-(2,4-dibromo-5-hydroxyphenyl)-7-(4-hydroxyphenyl)hepta-1,6-diene-3,5-dione (CU544)

The title compound was synthesized using the same procedure employed for Example 1, but with 2,4-dibromo-5-hydroxybenzaldehyde (32 mg, 0.11 mmol, prepared according to the procedure described in Tetrahedron: Asymmetry, (2002), 13, 2261) instead of 2-chloro-4-hydroxybenzaldehyde (17 mg, 0.11 mmol). The product was obtained as a solid (17.2 mg, 42%) having the following characteristics.

$^1$H NMR (δ, acetone-$d_6$): 6.07 (s, 1H), 6.72 (d, J=16 Hz, 1H), 6.75 (d, J=16 Hz, 1H), 6.91 (d, J=8.7 Hz, 2H), 7.44 (s, 1H), 7.59 (d, J=8.7 Hz, 2H), 7.67 (d, J=16 Hz, 1H), 7.82 (s, 1H), 7.82 (d, J=16 Hz, 1H).

Melting Point 255-259° C., MS (ESI+) m/z 465.2 (M+1).

Example 57

Synthesis of (E)-1-(5-benzyloxy-2-nitrophenyl)-7-(4-hydroxyphenyl)hept-1-ene-3,5-dione (CU548)

The title compound was synthesized using the same procedure employed for Example 40 (2), but with 5-benzyloxy-2-nitrobenzaldehyde (20 mg, 78 μmol) instead of 2-chloro-4-hydroxybenzaldehyde (12 mg, 78 μmol). The product was obtained as a solid (6.8 mg, 20%) having the following characteristics.

$^1$H NMR (δ, acetone-$d_6$): 2.74 (t, J=8 Hz, 2H), 2.87 (t, J=8 Hz, 2H), 5.34 (s, 2H), 5.90 (s, 1H), 6.73 (d, J=16 Hz, 1H), 6.75 (d, J=8.7 Hz, 2H), 7.07 (d, J=8.7 Hz, 2H), 7.24 (dd, J=2.9, 9.2 Hz, 1H), 7.36~7.46 (m, 3H), 7.44 (d, J=2.9 Hz, 1H), 7.52 (d, J=7.2 Hz, 2H), 8.04 (d, J=16 Hz, 1H), 8.13 (d, J=9.2 Hz, 1H).

MS (ESI+) m/z 446.5 (M+1), 468.5 (M+Na).

Example 58

Synthesis of (E)-1-(2-bromo-5-hydroxyphenyl)-7-(4-hydroxyphenyl)hept-1-ene-3,5-dione (CU549)

The title compound was synthesized using the same procedure employed for Example 40 (2), but with 2-bromo-5-hydroxybenzaldehyde (16 mg, 78 μmol) instead of 2-chloro-4-hydroxybenzaldehyde (12 mg, 78 μmol). The product was obtained as a solid (8.0 mg, 26%) having the following characteristics.

$^1$H NMR (δ, acetone-$d_6$): 2.73 (t, J=8 Hz, 2H), 2.87 (t, J=8 Hz, 2H), 5.89 (s, 1H), 6.65 (d, J=16 Hz, 1H), 6.75 (d, J=8.7 Hz, 2H), 6.84 (dd, J=2.9, 8.7 Hz, 1H), 7.08 (d, J=8.7 Hz, 2H), 7.26 (d, J=2.9 Hz, 1H), 7.48 (d, J=8.7 Hz, 1H), 7.83 (d, J=16 Hz, 1H).

Melting Point 161-165° C., MS (ESI+) m/z 389.2 (M+1), 411.2 (M+Na).

Example 59

Synthesis of (1E,6E)-1-[2-chloro-4-(2-dimethylaminoethoxy)phenyl]-7-(4-hydroxyphenyl)hepta-1,6-diene-3,5-dione (CU551)

(1) Synthesis of 2-chloro-4-(2-dimethylaminoethoxy)benzaldehyde

A suspension of 2-chloro-4-hydroxybenzaldehyde (234 mg, 1.49 mmol), (2-chloroethyl)dimethylamine hydrochloride (536 mg, 3.72 mmol), potassium carbonate (514 mg, 3.72 mmol), and tetrabutylammonium iodide (55 mg, 0.15 mmol) in 4.0 mL of acetonitrile was stirred at 115° C. overnight in a sealed tube. After the reaction mixture was diluted with water, the solution was extracted with ethyl acetate. The extract was washed with brine, and dried over $MgSO_4$. After filtration, the filtrate was concentrated in vacuo, and the residue was purified by silica gel column chromatography (chloroform/methanol=99/1 to 94/6) to obtain the title compound as a brown oil (137 mg, 40%).

(2) Synthesis of (1E,6E)-1-[2-chloro-4-(2-dimethylaminoethoxy)phenyl]-7-(4-hydroxyphenyl)hepta-1,6-diene-3,5-dione (CU551)

The title compound was synthesized using the same procedure employed for Example 1, but with 2-chloro-4-(2-dimethylaminoethoxy)benzaldehyde (25 mg, 0.11 mmol) instead of 2-chloro-4-hydroxybenzaldehyde (17 mg, 0.11 mmol). The product was obtained as a solid (4.2 mg, 12%) having the following characteristics.

1H NMR (δ, acetone-$d_6$): 2.26 (s, 6H), 2.69 (t, J=5.8 Hz, 2H), 4.18 (t, J=5.8 Hz, 2H), 6.04 (s, 1H), 6.70 (d, J=16 Hz, 1H), 6.79 (d, J=16 Hz, 1H), 6.88 (d, J=8.7 Hz, 2H), 6.99 (dd, J=2.4, 8.7 Hz, 1H), 7.10 (d, J=2.4 Hz, 1H), 7.59 (d, J=8.7 Hz, 2H), 7.64 (d, J=16 Hz, 1H), 7.85 (d, J=8.7 Hz, 1H), 7.97 (d, J=16 Hz, 1H), 8.0 (s, 1H).

Melting Point 170-173° C., MS (ESI+) m/z 414 (M+1).

Example 60

Synthesis of (1E,6E)-1-[2-bromo-5-(2-dimethylaminoethoxy)phenyl]-7-(4-hydroxyphenyl)hepta-1,6-diene-3,5-dione (CU552)

(1) Synthesis of 2-bromo-5-(2-dimethylaminoethoxy)benzaldehyde

The title compound was synthesized using the same procedure employed for Example 59 (1), but with 2-bromo-5-hydroxybenzaldehyde (300 mg, 1.49 mmol) instead of 2-chloro-4-hydroxybenzaldehyde (234 mg, 1.49 mmol). The product was obtained as a brown oil (45 mg, 11%).

(2) Synthesis of (1E,6E)-1-[2-bromo-5-(2-dimethylaminoethoxy)phenyl]-7-(4-hydroxyphenyl)hepta-1,6-diene-3,5-dione (CU552)

The title compound was synthesized using the same procedure employed for Example 1, but with 2-bromo-5-(2-dimethylaminoethoxy)benzaldehyde (30 mg, 0.11 mmol) instead of 2-chloro-4-hydroxybenzaldehyde (17 mg, 0.11 mmol). The product was obtained as a solid (3.0 mg, 7%) having the following characteristics.

1H NMR (δ, acetone-$d_6$): 2.27 (s, 6H), 2.70 (t, J=5.8 Hz, 2H), 4.16 (t, J=5.8 Hz, 2H), 6.08 (s, 1H), 6.72 (d, J=16 Hz, 1H), 6.91 (d, J=8.7 Hz, 2H), 6.92 (d, J=16 Hz, 1H), 6.96 (dd, J=2.9, 9 Hz, 1H), 7.44 (d, J=2.9 Hz, 1H), 7.57 (d, J=9 Hz, 1H), 7.60 (d, J=8.7 Hz, 2H), 7.67 (d, J=16 Hz, 1H), 7.91 (d, J=16 Hz, 1H).

Melting Point 163-167° C., MS (ESI+) m/z 458 (M+1).

Example 61

Synthesis of (E)-1-[2-chloro-4-(2-dimethylaminoethoxy)phenyl]-7-(4-hydroxyphenyl)hept-1-ene-3,5-dione (CU553)

The title compound was synthesized using the same procedure employed for Example 40 (2), but with 2-chloro-4-(2-dimethylaminoethoxy)benzaldehyde (18 mg, 78 μmol) instead of 2-chloro-4-hydroxybenzaldehyde (12 mg, 78 μmol). The product was obtained as a solid (4.6 mg, 13%) having the following characteristics.

1H NMR (δ, acetone-$d_6$): 2.26 (s, 6H), 2.69 (t, J=5.8 Hz, 2H), 2.71 (t, J=7.7 Hz, 2H), 2.86 (t, J=7.7 Hz, 2H), 4.17 (t, J=5.8 Hz, 2H), 5.84 (s, 1H), 6.66 (d, J=16 Hz, 1H), 6.74 (d, J=8.7 Hz, 2H), 6.98 (dd, J=2.4, 8.7 Hz, 1H), 7.07 (d, J=8.7 Hz, 2H), 7.08 (d, J=2.4 Hz, 1H), 7.81 (d, J=8.7 Hz, 1H), 7.90 (d, J=16 Hz, 1H).

MS (ESI+) m/z 416 (M+1).

Example 62

Synthesis of (1E,6E)-1-(4-fluoro-2-trifluoromethylphenyl)-7-(4-hydroxyphenyl)hepta-1,6-diene-3,5-dione (CU554)

The title compound was synthesized using the same procedure employed for Example 1, but with 4-fluoro-2-trifluoromethylbenzaldehyde (21 mg, 0.11 mmol) instead of 2-chloro-4-hydroxybenzaldehyde (17 mg, 0.11 mmol). The product was obtained as a solid (6.8 mg, 20%) having the following characteristics.

1H NMR (δ, acetone-$d_6$): 6.09 (s, 1H), 6.73 (d, J=16 Hz, 1H), 6.91 (d, J=8.7 Hz, 2H), 6.91 (d, J=16 Hz, 1H), 7.5~7.6 (m, 2H), 7.60 (d, J=8.7 Hz, 2H), 7.68 (d, J=16 Hz, 1H), 7.89 (dd, J=1.9, 16 Hz, 1H), 8.10 (dd, J=5.3, 8.7 Hz, 1H), 8.9 (br s, OH).

Melting Point 164-170° C., MS (ESI+) m/z 479 (M+1).

Example 63

Synthesis of (1E,6E)-1-(4-dimethylamino-2-trifluoromethylphenyl)-7-(4-hydroxyphenyl)hepta-1,6-diene-3,5-dione (CU555)

(1) Synthesis of 4-dimethylamino-2-trifluoromethylbenzaldehyde

A suspension of 4-fluoro-2-trifluoromethylbenzaldehyde (500 mg, 2.60 mmol), dimethylamine (5.5 mol/L in ethanol, 0.95 mL, 5.2 mmol), potassium carbonate (360 mg, 2.6 mmol) in 5.2 mL of N,N-dimethylformamide was stirred at 110° C. overnight in a sealed tube. After the reaction mixture was diluted with water, the solution was extracted with ether. The extract was washed with brine, and dried over MgSO$_4$. After filtration, the filtrate was concentrated in vacuo, and the residue was purified by silica gel column chromatography (hexane/ethyl acetate=85/15 to 75/25) to obtain the title compound as a pale yellow powder (393 mg, 70%).

(2) Synthesis of (1E,6E)-1-(4-dimethylamino-2-trifluoromethylphenyl)-7-(4-hydroxyphenyl)hepta-1,6-diene-3,5-dione (CU555)

The title compound was synthesized using the same procedure employed for Example 1, but with 4-dimethylamino-2-trifluoromethylbenzaldehyde (24 mg, 0.11 mmol) instead of 2-chloro-4-hydroxybenzaldehyde (17 mg, 0.11 mmol). The product was obtained as a solid (16.0 mg, 45%) having the following characteristics.

1H NMR (δ, acetone-$d_6$): 3.12 (s, 6H), 5.98 (s, 1H), 6.68 (d, J=16 Hz, 1H), 6.72 (d, J=16 Hz, 1H), 6.90 (d, J=8.7 Hz, 2H), 6.99 (d, J=8 Hz, 1H), 7.00 (s, 1H), 7.58 (d, J=8.7 Hz, 2H), 7.62 (d, J=16 Hz, 1H), 7.91 (d, J=8 Hz, 1H), 7.93 (dd, J=~2, 16 Hz, 1H).

Melting Point 195-199° C., MS (ESI+) m/z 404 (M+1).

Example 64

Synthesis of (E)-1-(4-dimethylamino-2-trifluoromethylphenyl)-7-(4-hydroxyphenyl)hept-1-ene-3,5-dione (CU556)

The title compound was synthesized using the same procedure employed for Example 40 (2), but with 4-dimethylamino-2-trifluoromethylbenzaldehyde (17 mg, 78 μmol) instead of 2-chloro-4-hydroxybenzaldehyde (12 mg, 78 μmol). The product was obtained as a solid (20.3 mg, 64%) having the following characteristics.

1H NMR (δ, acetone-d$_6$): 2.68 (t, J=7.2 Hz, 2H), 2.7~2.9 (m, 2H), 3.10 (s, 6H), 5.79 (s, 1H), 6.59 (d, J=16 Hz, 1H), 6.74 (d, J=8.7 Hz, 2H), 6.98 (d, J=8 Hz, 1H), 6.99 (s, 1H), 7.07 (d, J=8.7 Hz, 2H), 7.85 (dd, J=~2, 16 Hz, 1H), 7.86 (d, J=8 Hz, 1H), 8.1 (br s, OH).

Melting Point 110-114° C., MS (ESI+) m/z 406 (M+1).

Example 65

Synthesis of (1E,6E)-1-(4-benzyloxybiphenyl-2-yl)-7-(4-hydroxy-2-methoxyphenyl)hepta-1,6-diene-3,5-dione (CU559)

(1) Synthesis of 6-(4-hydroxy-2-methoxyphenyl)hex-5-ene-2,4-dione

Ethyl acetate (7 mL), 2,4-pentanedione (9.6 mL, 94 mmol) and boron trioxide (5.9 g, 85 mmol) was placed in a 200 mL reaction vessel with a reflux condenser. To the stirring mixture at 85° C. was added dropwise a solution of 4-hydroxy-2-methoxybenzaldehyde (2.16 g, 14.2 mmol) and trimethyl orthoformate (1.6 mL, 14 mmol) in 14 mL of ethyl acetate. After the reaction mixture was stirred for 30 min at 95° C., n-butylamine (7.0 mL, 71 mmol) was added dropwise with additional stirring for 2 h. The reaction mixture was cooled to 50° C. before addition of 3N HCl (33 mL). After being stirred at 50° C. for 30 min, the mixture was filtered to remove solids. The filtrate was diluted with ethyl acetate, washed with brine twice, and dried over MgSO$_4$. After filtration, the filtrate was concentrated in vacuo, and the residue was purified by silica gel column chromatography (hexane/ethyl acetate=95/5 to 75/25) followed by recrystallization (hexane/ethyl acetate) to obtain the title compound as a pale yellow crystal (1.07 g, 33%).

1H NMR (δ, acetone-d$_6$): 2.09 (s, 3H), 3.87 (s, 3H), 5.73 (s, 1H), 6.49 (d, J=8.7 Hz, 1H), 6.53 (s, 1H), 6.58 (d, J=16 Hz, 1H), 7.51 (d, J=8.7 Hz, 1H), 7.84 (d, J=16 Hz, 1H), 8.9 (br s, OH).

Melting Point 139-142° C., MS (ESI+) m/z 235.1 (M+1).

(2) Synthesis of (1E,6E)-1-(4-benzyloxybiphenyl-2-yl)-7-(4-hydroxy-2-methoxyphenyl)hepta-1,6-diene-3,5-dione (CU559)

6-(4-Hydroxy-2-methoxyphenyl)hex-5-ene-2,4-dione (20 mg, 85 μmol) and boron trioxide (11 mg, 0.16 mmol) was placed in a 20 mL reaction vessel, and dissolved in 0.4 mL of ethyl acetate. To the stirring mixture at 80° C. was added a solution of 4-benzyloxybiphenyl-2-carboxyaldehyde (33 mg, 0.11 mmol) and tri-n-butyl borate (25 μL, 93 μmol), sequentially. After the reaction mixture was stirred for 2 h at the same temperature, n-butylamine (10 μL, 0.10 mmol) was added with additional stirring for 1 h. The reaction mixture was treated with a 1:1 solution (1 mL) of 1N HCl and brine at room temperature, and was stirred at 50° C. for 5 min to 1 h (if necessary, the reaction mixture was neutralized by saturated NaHCO$_3$ aqueous solution). The organic layer was purified directly by silica gel column chromatography (eluting with hexane/ethyl acetate or chloroform/methanol) to obtain the title compound (16.8 mg, 39%) as a solid.

1H NMR (δ, acetone-d$_6$): 3.89 (s, 3H), 5.26 (s, 2H), 5.94 (s, 1H), 6.51 (dd, J=2.4, 8.2 Hz, 1H), 6.54 (d, J=2.4 Hz, 1H), 6.71 (d, J=16 Hz, 1H), 6.85 (d, J=16 Hz, 1H), 7.16 (dd, J=2.4, 8.2 Hz, 1H), 7.4~7.7 (m, 13H), 7.62 (d, J=16 Hz, 1H), 7.93 (d, J=16 Hz, 1H).

Melting Point 175-180° C., MS (ESI+) m/z 505 (M+1).

Example 66

Synthesis of (1E,6E)-1-(2-bromo-5-hydroxyphenyl)-7-(4-hydroxy-2-methoxyphenyl)hepta-1,6-diene-3,5-dione (CU561)

The title compound was synthesized using the same procedure employed for Example 65 (2), but with 2-bromo-5-hydroxybenzaldehyde (23 mg, 0.11 mmol) instead of 4-benzyloxybiphenyl-2-carboxyaldehyde (33 mg, 0.11 mmol). The product was obtained as a solid (11.6 mg, 33%) having the following characteristics.

1H NMR (δ, acetone-d$_6$): 3.90 (s, 3H), 6.04 (s, 1H), 6.52 (dd, J=2.4, 8.7 Hz, 1H), 6.55 (d, J=2.4 Hz, 1H), 6.77 (d, J=16 Hz, 1H), 6.78 (d, J=16 Hz, 1H), 6.86 (dd, J=2.9, 8.7 Hz, 1H), 7.30 (d, J=2.9 Hz, 1H), 7.49 (d, J=8.7 Hz, 1H), 7.57 (d, J=8.7 Hz, 1H), 7.89 (d, J=16 Hz, 1H), 7.97 (d, J=16 Hz, 1H).

Melting Point 92-98° C., MS (ESI+) m/z 417 (M+1).

Example 67

Synthesis of (1E,6E)-1-(2-bromo-5-hydroxyphenyl)-7-(1H-indol-6-yl)hepta-1,6-diene-3,5-dione (CU562)

(1) Synthesis of 6-(1H-indol-6-yl)hex-5-ene-2,4-dione

Ethyl acetate (7 mL), 2,4-pentanedione (9.35 mL, 90.9 mmol) and boron trioxide (5.76 g, 82.7 mmol) was placed in a 200 mL reaction vessel with a reflux condenser. To the stirring mixture at 85° C. was added dropwise a solution of 1H-indole-6-carboxaldehyde (2.00 g, 13.8 mmol) and trimethyl orthoformate (1.6 mL, 14 mmol) in 14 mL of ethyl acetate. After the reaction mixture was stirred for 30 min at 95° C., n-butylamine (6.8 mL, 69 mmol) was added dropwise with additional stirring for 2 h. The reaction mixture was cooled to 50° C. before addition of 3N HCl (32 mL). After being stirred at 50° C. for 30 min, the mixture was filtered to remove solids. The filtrate was diluted with ethyl acetate, washed with brine twice, and dried over MgSO$_4$. After filtration, the filtrate was concentrated in vacuo, and the residue was purified by silica gel column chromatography (hexane/ethyl acetate=95/5 to 75/25) followed by recrystallization (hexane/ethyl acetate) to obtain the title compound as a pale yellow crystal (0.92 g, 29%).

1H NMR (δ, acetone-d$_6$): 2.12 (s, 3H), 5.82 (s, 1H), 6.52 (d, J=~2 Hz, 1H), 6.67 (d, J=16 Hz, 1H), 7.40 (d, J=8.2 Hz, 1H), 7.45 (d, J=~2 Hz, 1H), 7.60 (d, J=8.2 Hz, 1H), 7.70 (s, 1H), 7.72 (d, J=16 Hz, 1H), 10.5 (br s, NH).

Melting Point 138-142° C., MS (ESI+) m/z 228.3 (M+1).

(2) Synthesis of (1E,6E)-1-(2-bromo-5-hydroxyphenyl)-7-(1H-indol-6-yl)hepta-1,6-diene-3,5-dione (CU562)

6-(1H-Indol-6-yl)hex-5-ene-2,4-dione (19.4 mg, 85 μmol) and boron trioxide (11 mg, 0.16 mmol) was placed in a 20 mL reaction vessel, and dissolved in 0.4 mL of ethyl acetate. To the stirring mixture at 80° C. was added a solution of 2-bromo-5-hydroxybenzaldehyde (23 mg, 0.11 mmol) and tri-n-butyl borate (25 μL, 93 μmol), sequentially. After the reaction mixture was stirred for 2 h at the same temperature, n-butylamine (10 μL, 0.10 mmol) was added with additional stirring for 1 h. The reaction mixture was treated with a 1:1 solution (1 mL) of 1N HCl and brine at room temperature, and was stirred at 50° C. for 5 min to 1 h (if necessary, the reaction mixture was neutralized by saturated NaHCO$_3$ aqueous solution). The organic layer was purified directly by silica gel column chromatography (eluting with hexane/ethyl acetate or chloroform/methanol) to obtain the title compound (7.0 mg, 19%) as a solid.

1H NMR (δ, acetone-d$_6$): 6.13 (s, 1H), 6.53 (d, J=~2 Hz, 1H), 6.79 (d, J=16 Hz, 1H), 6.86 (d, J=16 Hz, 1H), 6.86 (dd, J=2.9, 8.7 Hz, 1H), 7.31 (d, J=2.9 Hz, 1H), 7.46 (d, J=8.2 Hz, 1H), 7.48 (d, J=~2 Hz, 1H), 7.50 (d, J=8.7 Hz, 1H), 7.63 (d, J=8.2 Hz, 1H), 7.76 (s, 1H), 7.85 (d, J=16 Hz, 1H), 7.91 (d, J=16 Hz, 1H), 8.8 (br s, OH), 10.5 (s, NH).

Melting Point 196-200° C., MS (ESI+) m/z 410 (M+1), 432 (M+Na).

Example 68

Synthesis of (1E,6E)-1-(4-benzyloxybiphenyl-2-yl)-7-(1H-indol-6-yl)hepta-1,6-diene-3,5-dione (CU566)

The title compound was synthesized using the same procedure employed for Example 67 (2), but with 4-benzyloxybiphenyl-2-carboxyaldehyde (33 mg, 0.11 mmol) instead of 2-bromo-5-hydroxybenzaldehyde (23 mg, 0.11 mmol). The product was obtained as a solid (8.8 mg, 20%) having the following characteristics.

1H NMR (δ, acetone-d$_6$): 5.28 (s, 2H), 6.02 (s, 1H), 6.52 (d, J=~2 Hz, 1H), 6.81 (d, J=16 Hz, 1H), 6.86 (d, J=16 Hz, 1H), 7.17 (dd, J=2.4, 8.7 Hz, 1H), 7.3~7.6 (m, 13H), 7.62 (d, J=8 Hz, 1H), 7.63 (s, 1H), 7.64 (d, J=16 Hz, 1H), 7.74 (s, 1H), 7.79 (d, J=16 Hz, 1H).

Melting Point 178-183° C., MS (ESI+) m/z 498 (M+1), 520 (M+Na).

Example 69

Synthesis of (1E,6E)-1-(1H-indol-6-yl)-7-(2-trifluoromethylphenyl)hepta-1,6-diene-3,5-dione (CU571)

The title compound was synthesized using the same procedure employed for Example 67 (2), but with 2-trifluoromethylbenzaldehyde (20 μL, 0.11 mmol) instead of 2-bromo-5-hydroxybenzaldehyde (23 mg, 0.11 mmol). The product was obtained as a solid (2.5 mg, 7%) having the following characteristics.

1H NMR (δ, acetone-d$_6$): 6.15 (s, 1H), 6.53 (br s, 1H), 6.87 (d, J=16 Hz, 1H), 6.95 (d, J=16 Hz, 1H), 7.47 (d, J=8.2 Hz, 1H), 7.48 (br s, 1H), 7.62 (m, 1H), 7.63 (d, J=8.2 Hz, 1H), 7.77 (s, 1H), 7.74 (dd, J=7.7, 7.7 Hz, 1H), 7.82 (d, J=7.7 Hz, 1H), 7.86 (d, J=16 Hz, 1H), 7.97 (dd, J=~2, 16 Hz, 1H), 8.04 (d, J=7.7 Hz, 1H), 10.5 (br s, NH).

Melting Point 178-182° C., MS (ESI+) m/z 373 (M+1), 395 (M+Na).

Example 70

Synthesis of (1E,6E)-1-(4-hydroxy-2-methoxyphenyl)-7-(2-trifluoromethylphenyl)hepta-1,6-diene-3,5-dione (CU574)

The title compound was synthesized using the same procedure employed for Example 65 (2), but with 2-trifluoromethylbenzaldehyde (20 μL, 0.11 mmol) instead of 4-benzyloxybiphenyl-2-carboxyaldehyde (33 mg, 0.11 mmol). The product was obtained as a solid (5.4 mg, 16%) having the following characteristics.

1H NMR (δ, acetone-d$_6$): 3.90 (s, 3H), 6.06 (s, 1H), 6.52 (dd, J=2.4, 8.7 Hz, 1H), 6.55 (d, J=2.4 Hz, 1H), 6.78 (d, J=16 Hz, 1H), 6.93 (d, J=16 Hz, 1H), 7.58 (d, J=8.7 Hz, 1H), 7.61 (dd, J=7.7, 7.7 Hz, 1H), 7.73 (dd, J=7.7, 7.7 Hz, 1H), 7.81 (d, J=7.7 Hz, 1H), 7.95 (dd, J=~2, 16 Hz, 1H), 7.99 (d, J=16 Hz, 1H), 8.03 (d, J=7.7 Hz, 1H).

Melting Point 176-180° C., MS (ESI+) m/z 391 (M+1), 413 (M+Na).

Example 71

Synthesis of (1E,6E)-1-(2-chloro-4-dimethylaminophenyl)-7-(4-hydroxy-2-methoxyphenyl)hepta-1,6-diene-3,5-dione (CU581)

The title compound was synthesized using the same procedure employed for Example 65 (2), but with 2-chloro-4-dimethylaminobenzaldehyde (20 mg, 0.11 mmol) instead of 4-benzyloxybiphenyl-2-carboxyaldehyde (33 mg, 0.11 mmol). The product was obtained as a solid (13.0 mg, 38%) having the following characteristics.

1H NMR (δ, acetone-d$_6$): 3.05 (s, 6H), 3.89 (s, 3H), 5.92 (s, 1H), 6.51 (dd, J=2.4, 8.7 Hz, 1H), 6.54 (d, J=2.4 Hz, 1H), 6.65 (d, J=16 Hz, 1H), 6.71 (d, J=16 Hz, 1H), 6.72~6.78 (m, 2H), 7.55 (d, J=8.7 Hz, 1H), 7.74 (d, J=9.7 Hz, 1H), 7.91 (d, J=16 Hz, 1H), 7.99 (d, J=16 Hz, 1H).

Melting Point 187-192° C., MS (ESI+) m/z 400 (M+1).

Example 72

Synthesis of (1E,6E)-1-(4-hydroxybiphenyl-2-yl)-7-(4-hydroxy-2-methoxyphenyl)hepta-1,6-diene-3,5-dione (CU582)

The title compound was synthesized using the same procedure employed for Example 65 (2), but with 4-hydroxybiphenyl-2-carboxyaldehyde (23 mg, 0.11 mmol) instead of 4-benzyloxybiphenyl-2-carboxyaldehyde (33 mg, 0.11 mmol). The product was obtained as a solid (21.4 mg, 60%) having the following characteristics.

1H NMR (δ, acetone-d$_6$): 3.89 (s, 3H), 5.92 (s, 1H), 6.51 (d, J=2.4, 8.7 Hz, 1H), 6.54 (d, J=2.4 Hz, 1H), 6.71 (d, J=16 Hz, 1H), 6.73 (d, J=16 Hz, 1H), 6.98 (dd, J=2.4, 8.2 Hz, 1H), 7.24 (d, J=8.2 Hz, 1H), 7.28~7.35 (m, 3H), 7.35~7.5 (m, 3H), 7.55 (d, J=8.7 Hz, 1H), 7.61 (d, J=16 Hz, 1H), 7.93 (d, J=16 Hz, 1H).

Melting Point 108-114° C., MS (ESI+) m/z 415 (M+1), 437 (M+Na).

Example 73

Synthesis of (1E,6E)-1-(2-chloro-4-dimethylaminophenyl)-7-(1H-indol-6-yl)hepta-1,6-diene-3,5-dione (CU584)

The title compound was synthesized using the same procedure employed for Example 67 (2), but with 2-chloro-4-dimethylaminobenzaldehyde (20 mg, 0.11 mmol) instead of 2-bromo-5-hydroxybenzaldehyde (23 mg, 0.11 mmol). The product was obtained as a solid (6.2 mg, 18%) having the following characteristics.

1H NMR (δ, acetone-d$_6$): 3.06 (s, 6H), 6.00 (s, 1H), 6.52 (br s, 1H), 6.67 (d, J=16 Hz, 1H), 6.72~6.78 (m, 2H), 6.81 (d, J=16 Hz, 1H), 7.44 (d, J=8.2 Hz, 1H), 7.46 (d, J=~2 Hz, 1H), 7.62 (d, J=8.2 Hz, 1H), 7.73 (s, 1H), 7.75 (m, 1H), 7.78 (d, J=16 Hz, 1H), 8.01 (d, J=16 Hz, 1H), 10.5 (br s, NH).

Melting Point 180-185° C., MS (ESI+) m/z 393 (M+1).

Example 74

Synthesis of (1E,6E)-1-(4-hydroxy-2-methoxyphenyl)-7-(5-hydroxy-2-nitrophenyl)hepta-1,6-diene-3,5-dione (CU585)

The title compound was synthesized using the same procedure employed for Example 65 (2), but with 5-hydroxy-2-nitrobenzaldehyde (18 mg, 0.11 mmol) instead of 4-benzyloxybiphenyl-2-carboxyaldehyde (33 mg, 0.11 mmol). The product was obtained as a solid (9.6 mg, 29%) having the following characteristics.

1H NMR ($\delta$, acetone-$d_6$): 3.90 (s, 3H), 6.06 (s, 1H), 6.52 (d, J=2.4, 8.7 Hz, 1H), 6.55 (d, J=2.4 Hz, 1H), 6.73 (d, J=16 Hz, 1H), 6.77 (d, J=16 Hz, 1H), 7.05 (dd, J=2.4, 9.2 Hz, 1H), 7.22 (d, J=2.4 Hz, 1H), 7.57 (d, J=8.7 Hz, 1H), 7.98 (d, J=16 Hz, 1H), 8.07 (d, J=9.2 Hz, 1H), 7.93 (d, J=16 Hz, 1H).

Melting Point 119-123° C., MS (ESI+) m/z 384 (M+1), 406 (M+Na).

Example 75

Synthesis of (1E,6E)-1-(5-benzyloxy-2-nitrophenyl)-7-(1H-indol-6-yl)hepta-1,6-diene-3,5-dione (CU588)

The title compound was synthesized using the same procedure employed for Example 67 (2), but with 5-benzyloxy-2-nitrobenzaldehyde (29 mg, 0.11 mmol) instead of 2-bromo-5-hydroxybenzaldehyde (23 mg, 0.11 mmol). The product was obtained as a solid (3.1 mg, 8%) having the following characteristics.

1H NMR ($\delta$, acetone-$d_6$): 5.36 (s, 2H), 6.14 (s, 1H), 6.53 (d, J=2.4 Hz, 1H), 6.86 (d, J=16 Hz, 1H), 6.87 (d, J=16 Hz, 1H), 7.26 (dd, J=2.4, 8.7 Hz, 1H), 7.35~7.5 (m, 6H), 7.54 (d, J=7.7 Hz, 2H), 7.63 (d, J=8.7 Hz, 1H), 7.77 (s, 1H), 7.86 (d, J=16 Hz, 1H), 8.11 (d, J=16 Hz, 1H), 8.15 (d, J=8.7 Hz, 1H), 10.5 (br s, NH).

Melting Point 181-186° C., MS (ESI+) m/z 467 (M+1), 489 (M+Na).

Example 76

Synthesis of (1E,6E)-1-(4-dimethylamino-2-nitrophenyl)-7-(1H-indol-6-yl)hepta-1,6-diene-3,5-dione (CU592)

The title compound was synthesized using the same procedure employed for Example 67 (2), but with 4-dimethylamino-2-nitrobenzaldehyde (21 mg, 0.11 mmol) instead of 2-bromo-5-hydroxybenzaldehyde (23 mg, 0.11 mmol). The product was obtained as a solid (5.4 mg, 15%) having the following characteristics.

1H NMR ($\delta$, acetone-$d_6$): 3.13 (s, 6H), 6.04 (s, 1H), 6.52 (d, J=2.4 Hz, 1H), 6.73 (d, J=16 Hz, 1H), 6.82 (d, J=16 Hz, 1H), 7.05 (dd, J=2.4, 9.2 Hz, 1H), 7.16 (d, J=2.4 Hz, 1H), 7.44 (dd, J=~2, 9.2 Hz, 1H), 7.47 (m, 1H), 7.62 (d, J=9.2 Hz, 1H), 7.74 (s, 1H), 7.80 (d, J=16 Hz, 1H), 7.82 (d, J=16 Hz, 1H), 7.84 (d, J=9.2 Hz, 1H), 10.5 (br s, NH).

Melting Point 196-201° C., MS (ESI+) m/z 404 (M+1), 426 (M+Na).

Example 77

Synthesis of (1E,6E)-1-(5-benzyloxy-2-nitrophenyl)-7-(4-hydroxy-2-methoxyphenyl)hepta-1,6-diene-3,5-dione (CU594)

The title compound was synthesized using the same procedure employed for Example 65 (2), but with 5-benzyloxy-2-nitrobenzaldehyde (29 mg, 0.11 mmol) instead of 4-benzyloxybiphenyl-2-carboxyaldehyde (33 mg, 0.11 mmol). The product was obtained as a solid (18.4 mg, 46%) having the following characteristics.

1H NMR ($\delta$, acetone-$d_6$): 3.90 (s, 1H), 5.35 (s, 2H), 6.05 (s, 1H), 6.51 (dd, J=2.4, 8.7 Hz, 1H), 6.55 (d, J=2.4 Hz, 1H), 6.77 (d, J=16 Hz, 1H), 6.84 (d, J=16 Hz, 1H), 7.24 (dd, J=2.4, 9.2 Hz, 1H), 7.35~7.5 (m, 4H), 7.54 (d, J=6.8 Hz, 2H), 7.57 (d, J=8.7 Hz, 1H), 7.98 (d, J=16 Hz, 1H), 8.09 (d, J=16 Hz, 1H), 8.13 (d, J=9.2 Hz, 1H).

Melting Point 183-186° C., MS (ESI+) m/z 474 (M+1), 496 (M+Na).

Example 78

Synthesis of (1E,6E)-1-(5-hydroxy-2-nitrophenyl)-7-(1H-indol-6-yl)hepta-1,6-diene-3,5-dione (CU596)

The title compound was synthesized using the same procedure employed for Example 67 (2), but with 5-hydroxy-2-nitrobenzaldehyde (18 mg, 0.11 mmol) instead of 2-bromo-5-hydroxybenzaldehyde (23 mg, 0.11 mmol). The product was obtained as a solid (4.6 mg, 14%) having the following characteristics.

1H NMR ($\delta$, acetone-$d_6$): 6.15 (s, 1H), 6.53 (d, J=2.9 Hz, 1H), 6.74 (d, J=16 Hz, 1H), 6.86 (d, J=16 Hz, 1H), 7.06 (dd, J=2.4, 8.7 Hz, 1H), 7.23 (d, J=2.4 Hz, 1H), 7.46 (dd, J=~2, 8.7 Hz, 1H), 7.47 (m, 1H), 7.63 (d, J=8.7 Hz, 1H), 7.76 (s, 1H), 7.85 (d, J=16 Hz, 1H), 8.08 (d, J=8.7 Hz, 1H), 8.11 (d, J=16 Hz, 1H), 10.5 (br s, NH).

Melting Point 204-207° C., MS (ESI+) m/z 377 (M+1), 399 (M+Na).

Example 79

Synthesis of (1E,6E)-1-(2-chloro-4-hydroxyphenyl)-7-(4-hydroxy-2-methoxyphenyl)hepta-1,6-diene-3,5-dione (CU600)

The title compound was synthesized using the same procedure employed for Example 65 (2), but with 2-chloro-4-hydroxybenzaldehyde (17 mg, 0.11 mmol) instead of 4-benzyloxybiphenyl-2-carboxyaldehyde (33 mg, 0.11 mmol). The product was obtained as a solid (10.4 mg, 33%) having the following characteristics.

1H NMR ($\delta$, acetone-$d_6$): 3.90 (s, 3H), 5.97 (s, 1H), 6.51 (dd, J=2.4, 8.7 Hz, 1H), 6.55 (d, J=2.4 Hz, 1H), 6.74 (d, J=16 Hz, 1H), 6.75 (d, J=16 Hz, 1H), 6.89 (dd, J=2.4, 8.7 Hz, 1H), 6.98 (d, J=2.4 Hz, 1H), 7.56 (d, J=8.7 Hz, 1H), 7.79 (d, J=8.7 Hz, 1H), 7.94 (d, J=16 Hz, 1H), 7.96 (d, J=16 Hz, 1H).

Melting Point 206-211° C., MS (ESI+) m/z 373 (M+1), 395 (M+Na).

Example 80

Synthesis of (1E,6E)-1-(2-chloro-4-hydroxyphenyl)-7-(1H-indol-6-yl)hepta-1,6-diene-3,5-dione (CU601)

The title compound was synthesized using the same procedure employed for Example 67 (2), but with 2-chloro-4- hydroxybenzaldehyde (17 mg, 0.11 mmol) instead of 2-bromo-5-hydroxybenzaldehyde (23 mg, 0.11 mmol). The product was obtained as a solid (7.8 mg, 24%) having the following characteristics.

1H NMR (δ, acetone-$d_6$): 6.06 (s, 1H), 6.53 (d, J=1.9 Hz, 1H), 6.76 (d, J=16 Hz, 1H), 6.83 (d, J=16 Hz, 1H), 6.90 (dd, J=2.4, 8.7 Hz, 1H), 6.99 (d, J=2.4 Hz, 1H), 7.44 (dd, J=~2, 8.7 Hz, 1H), 7.47 (m, 1H), 7.62 (d, J=8.7 Hz, 1H), 7.75 (br s, 1H), 7.80 (d, J=8.7 Hz, 1H), 7.82 (d, J=16 Hz, 1H), 7.98 (d, J=16 Hz, 1H), 10.5 (br s, NH).

Melting Point 182-186° C., MS (ESI+) m/z 366 (M+1), 388 (M+Na).

Example 81

Synthesis of (1E,6E)-1-(4-dimethylamino-2-nitrophenyl)-7-(4-hydroxy-2-methoxyphenyl)hepta-1,6-diene-3,5-dione (CU603)

The title compound was synthesized using the same procedure employed for Example 65 (2), but with 4-dimethylamino-2-nitrobenzaldehyde (21 mg, 0.11 mmol) instead of 4-benzyloxybiphenyl-2-carboxyaldehyde (33 mg, 0.11 mmol). The product was obtained as a solid (4.2 mg, 12%) having the following characteristics.

1H NMR (δ, acetone-$d_6$): 3.13 (s, 6H), 3.89 (s, 3H), 5.96 (s, 1H), 6.51 (d, J=2.4, 8.7 Hz, 1H), 6.55 (d, J=2.4 Hz, 1H), 6.72 (d, J=16 Hz, 1H), 6.73 (d, =16 Hz, 1H), 7.05 (d, J=2.9, 8.7 Hz, 1H), 7.16 (d, J=2.9 Hz, 1H), 7.55 (d, J=8.7 Hz, 1H), 7.79 (d, J=16 Hz, 1H), 7.83 (d, J=8.7 Hz, 1H), 7.93 (d, J=16 Hz, 1H).

Melting Point 223-226° C., MS (ESI+) m/z 411 (M+1), 433 (M+Na).

Example 82

Synthesis of (1E,6E)-1-(4-hydroxybiphenyl-2-yl)-7-(1H-indol-6-yl)hepta-1,6-diene-3,5-dione (CU604)

The title compound was synthesized using the same procedure employed for Example 67 (2), but with 4-hydroxybiphenyl-2-carboxyaldehyde (23 mg, 0.11 mmol) instead of 2-bromo-5-hydroxybenzaldehyde (23 mg, 0.11 mmol). The product was obtained as a solid (12.0 mg, 33%) having the following characteristics.

1H NMR (δ, acetone-$d_6$): 6.02 (s, 1H), 6.53 (d, J=~2 Hz, 1H), 6.74 (d, J=16 Hz, 1H), 6.81 (d, J=16 Hz, 1H), 7.00 (dd, J=2.4, 8.2 Hz, 1H), 7.25 (d, J=8.2 Hz, 1H), 7.3~7.35 (m, 3H), 7.35~7.5 (m, 5H), 7.62 (d, J=8.2 Hz, 1H), 7.63 (d, J=16 Hz, 1H), 7.74 (br s, 1H), 7.79 (d, J=16 Hz, 1H), 10.5 (br s, NH).

Melting Point 185-191° C., MS (ESI+) m/z 408 (M+1), 430 (M+Na).

Example 83

Synthesis of (1E,6E)-1-(2-bromo-5-hydroxyphenyl)-7-(5-hydroxy-2-methoxyphenyl)hepta-1,6-diene-3,5-dione (CU608)

(1) Synthesis of 6-(2-bromo-5-hydroxyphenyl)hex-5-ene-2,4-dione

Ethyl acetate (3.1 mL), 2,4-pentanedione (4.25 mL, 41.4 mmol) and boron trioxide (2.6 g, 38 mmol) was placed in a 200 mL reaction vessel with a reflux condenser. To the stirring mixture at 85° C. was added dropwise a solution of 2-bromo-5-hydroxybenzaldehyde (1.26 g, 6.27 mmol) and trimethyl orthoformate (0.70 mL, 6.4 mmol) in 6 mL of ethyl acetate. After the reaction mixture was stirred for 30 min at 95° C., n-butylamine (3.1 mL, 31 mmol) was added dropwise with additional stirring for 2 h. The reaction mixture was cooled to 50° C. before addition of 3N HCl (15 mL). After being stirred at 50° C. for 30 min, the mixture was filtered to remove solids. The filtrate was diluted with ethyl acetate, washed with brine twice, and dried over $MgSO_4$. After filtration, the filtrate was concentrated in vacuo, and the residue was purified by silica gel column chromatography (hexane/ethyl acetate=85/15 to 75/25) twice followed by recrystallization (hexane/ethyl acetate) to obtain the title compound as a yellow crystal (0.12 g, 7%).

1H NMR (δ, acetone-$d_6$): 2.16 (s, 3H), 5.88 (s, 1H), 6.65 (d, J=16 Hz, 1H), 6.85 (dd, J=2.9, 8.7 Hz, 1H), 7.27 (d, J=2.9 Hz, 1H), 7.48 (d, J=8.7 Hz, 1H), 7.84 (d, J=16 Hz, 1H), 8.8 (br s, OH).

13C NMR (δ, acetone-$d_6$): 26.4, 101.8, 114.1, 114.2, 119.0, 125.7, 134.1, 135.6, 137.0, 157.3, 175.5, 199.4.

Melting Point 185-188° C., MS (ESI+) m/z 283.1 (M+1).

(2) Synthesis of (1E,6E)-1-(2-bromo-5-hydroxyphenyl)-7-(5-hydroxy-2-methoxyphenyl)hepta-1,6-diene-3,5-dione (CU608)

6-(2-Bromo-5-hydroxyphenyl)hex-5-ene-2,4-dione (15 mg, 53 μmol) and boron trioxide (11 mg, 0.16 mmol) was placed in a 20 mL reaction vessel, and dissolved in 0.4 mL of ethyl acetate. To the stirring mixture at 80° C. was added a solution of 5-hydroxy-2-methoxybenzaldehyde (10 mg, 0.07 mmol) and tri-n-butyl borate (25 mL, 93 μmol), sequentially. After the reaction mixture was stirred for 2 h at the same temperature, n-butylamine (10 μL, 0.10 mmol) was added with additional stirring for 1 h. The reaction mixture was treated with a 1:1 solution (1 mL) of 1N HCl and brine at room temperature, and was stirred at 50° C. for 5 min to 1 h (if necessary, the reaction mixture was neutralized by saturated $NaHCO_3$ aqueous solution). The organic layer was purified directly by silica gel column chromatography (eluting with hexane/ethyl acetate or chloroform/methanol) to obtain the title compound (2.2 mg, 10%) as a solid.

1H NMR (δ, acetone-$d_6$): 3.86 (s, 3H), 6.12 (s, 1H), 6.81 (d, J=16 Hz, 1H), 6.84 (d, J=16 Hz, 1H), 6.85~7.0 (m, 3H), 7.16 (d, J=~2 Hz, 1H), 7.31 (d, J=2.4 Hz, 1H), 7.50 (d, J=8.7 Hz, 1H), 7.92 (d, J=16 Hz, 1H), 7.99 (d, J=16 Hz, 1H), 8.1 (br s, OH), 8.8 (br s, OH).

Melting Point 90-96° C., MS (ESI+) m/z 417 (M+1), 439 (M+Na).

Example 84

Synthesis of (1E,6E)-1-(2-bromo-5-hydroxyphenyl)-7-(2-chloro-4-dimethylaminophenyl)hepta-1,6-diene-3,5-dione (CU609)

The title compound was synthesized using the same procedure employed for Example 83 (2), but with 2-chloro-4-dimethylaminobenzaldehyde (13 mg, 0.07 mmol) instead of 5-hydroxy-2-methoxybenzaldehyde (10 mg, 0.07 mmol). The product was obtained as a solid (1.7 mg, 7%) having the following characteristics.

1H NMR (δ, acetone-$d_6$): 3.07 (s, 6H), 6.06 (s, 1H), 6.71 (d, J=16 Hz, 1H), 6.75~6.8 (m, 2H), 6.78 (d, J=16 Hz, 1H), 6.86 (dd, J=2.9, 8.7 Hz, 1H), 7.30 (d, J=2.9 Hz, 1H), 7.49 (d, J=8.7 Hz, 1H), 7.77 (d, J=9.7 Hz, 1H), 7.90 (d, J=16 Hz, 1H), 8.06 (d, J=16 Hz, 1H), 8.8 (br s, OH).

Melting Point 209-214° C., MS (ESI+) m/z 448 (M+1).

Example 85

Synthesis of (1E,6E)-1-(2-chloro-4-hydroxyphenyl)-7-(5-hydroxy-2-nitrophenyl)hepta-1,6-diene-3,5-dione (CU611)

(1) Synthesis of 6-(2-chloro-4-hydroxyphenyl)hex-5-ene-2,4-dione

Ethyl acetate (0.8 mL), 2,4-pentanedione (1.03 mL, 10.0 mmol) and boron trioxide (0.63 g, 9.1 mmol) was placed in a 200 mL reaction vessel with a reflux condenser. To the stirring mixture at 85° C. was added dropwise a solution of 2-chloro-4-hydroxybenzaldehyde (238 mg, 1.52 mmol) and trimethyl orthoformate (0.17 mL, 1.5 mmol) in 3.0 mL of ethyl acetate. After the reaction mixture was stirred for 30 min at 95° C., n-butylamine (0.80 mL, 7.6 mmol) was added dropwise with additional stirring for 2 h. The reaction mixture was cooled to 50° C. before addition of 3N HCl (3.5 mL). After being stirred at 50° C. for 30 min, the mixture was filtered to remove solids. The filtrate was diluted with ethyl acetate, washed with brine twice, and dried over $MgSO_4$. After filtration, the filtrate was concentrated in vacuo, and the residue was purified by silica gel column chromatography (hexane/ethyl acetate=85/15 to 75/25) followed by recrystallization (hexane/ethyl acetate) to obtain the title compound as a yellow crystal (56 mg, 12%).

1H NMR ($\delta$, acetone-$d_6$): 2.13 (s, 3H), 5.82 (s, 1H), 6.62 (d, J=16 Hz, 1H), 6.88 (dd, J=2.4, 8.7 Hz, 1H), 6.97 (d, J=2.4 Hz, 1H), 7.75 (d, J=8.7 Hz, 1H), 7.90 (d, J=16 Hz, 1H).

Melting Point 125-129° C., MS (ESI+) m/z 239.3 (M+1).

(2) Synthesis of (1E,6E)-1-(2-chloro-4-hydroxyphenyl)-7-(5-hydroxy-2-nitrophenyl)hepta-1,6-diene-3,5-dione (CU611)

6-(2-Chloro-4-hydroxyphenyl)hex-5-ene-2,4-dione (20.3 mg, 85 µmol) and boron trioxide (11 mg, 0.16 mmol) was placed in a 20 mL reaction vessel, and dissolved in 0.4 mL of ethyl acetate. To the stirring mixture at 80° C. was added a solution of 5-hydroxy-2-nitrobenzaldehyde (18 mg, 0.11 mmol) and tri-n-butyl borate (25 µL, 93 µmol), sequentially. After the reaction mixture was stirred for 2 h at the same temperature, n-butylamine (10 µL, 0.10 mmol) was added with additional stirring for 1 h. The reaction mixture was treated with a 1:1 solution (1 mL) of 1N HCl and brine at room temperature, and was stirred at 50° C. for 5 min to 1 h (if necessary, the reaction mixture was neutralized by saturated $NaHCO_3$ aqueous solution). The organic layer was purified directly by silica gel column chromatography (eluting with hexane/ethyl acetate or chloroform/methanol) to obtain the title compound (3.5 mg, 7%) as a solid.

1H NMR ($\delta$, acetone-$d_6$): 6.15 (s, 1H), 6.76 (d, J=16 Hz, 1H), 6.82 (d, J=16 Hz, 1H), 6.90 (dd, J=~2, 8.7 Hz, 1H), 7.00 (d, J=~2 Hz, 1H), 7.07 (dd, J=~2, 9.2 Hz, 1H), 7.24 (d, J=~2 Hz, 1H), 7.83 (d, J=8.7 Hz, 1H), 8.04 (d, J=16 Hz, 1H), 8.08 (d, J=9.2 Hz, 1H), 8.13 (d, J=16 Hz, 1H).

Melting Point 132-136° C., MS (ESI+) m/z 388 (M+1), 410 (M+Na).

Example 86

Synthesis of (1E,6E)-1-(2-bromo-5-hydroxyphenyl)-7-(4-hydroxy-3-methyoxyphenyl)hepta-1,6-diene-3,5-dione (CU612)

The title compound was synthesized using the same procedure employed for Example 2, but with 2-bromo-5-hydroxybenzaldehyde (23 mg, 0.11 mmol) instead of 2-chloro-4-hydroxybenzaldehyde (17 mg, 0.11 mmol). The product was obtained as a solid (2.4 mg, 7%) having the following characteristics.

1H NMR ($\delta$, acetone-$d_6$): 3.93 (s, 3H), 6.08 (s, 1H), 6.77 (d, J=16 Hz, 1H), 6.77 (d, J=16 Hz, 1H), 6.86 (dd, J=2.9, 8.7 Hz, 1H), 6.89 (d, J=8.2 Hz, 1H), 7.21 (dd, J=1.9, 8.2 Hz, 1H), 7.29 (d, J=2.9 Hz, 1H), 7.37 (d, J=1.9 Hz, 1H), 7.49 (d, J=8.7 Hz, 1H), 7.66 (d, J=16 Hz, 1H), 7.90 (d, J=16 Hz, 1H), 8.8 (br s, OH).

Melting Point 210-215° C., MS (ESI+) m/z 417 (M+1).

Example 87

Synthesis of (1E,6E)-1-(2-bromo-5-hydroxyphenyl)-7-(3-hydroxy-4-methyoxyphenyl)hepta-1,6-diene-3,5-dione (CU613)

The title compound was synthesized using the same procedure employed for Example 3, but with 2-bromo-5-hydroxybenzaldehyde (23 mg, 0.11 mmol) instead of 2-chloro-4-hydroxybenzaldehyde (17 mg, 0.11 mmol). The product was obtained as a solid (6.6 mg, 19%) having the following characteristics.

1H NMR ($\delta$, acetone-$d_6$): 3.91 (s, 3H), 6.10 (s, 1H), 6.73 (d, J=16 Hz, 1H), 6.78 (d, J=16 Hz, 1H), 6.86 (dd, J=2.9, 8.7 Hz, 1H), 7.01 (d, J=8.2 Hz, 1H), 7.17 (dd, J=1.9, 8.2 Hz, 1H), 7.22 (d, J=1.9 Hz, 1H), 7.31 (d, J=2.9 Hz, 1H), 7.49 (d, J=8.7 Hz, 1H), 7.63 (d, J=16 Hz, 1H), 7.8 (br s, OH), 7.91 (d, J=16 Hz, 1H), 8.8 (br s, OH).

Melting Point 90-94° C., MS (ESI+) m/z 417 (M+1).

Example 88

Synthesis of (1E,6E)-1,7-bis(2-bromo-5-hydroxyphenyl)hepta-1,6-diene-3,5-dione (CU614)

The title compound was synthesized using the same procedure employed for Example 19, but with 2-bromo-5-hydroxybenzaldehyde (50 mg, 0.25 mmol) instead of 2-chloro-4-hydroxybenzaldehyde (39 mg, 0.25 mmol). The product was obtained as a solid (8.0 mg, 17%) having the following characteristics.

1H NMR ($\delta$, acetone-$d_6$): 6.18 (s, 1H), 6.83 (d, J=16 Hz, 2H), 6.88 (dd, J=2.9, 8.7 Hz, 2H), 7.32 (d, J=2.9 Hz, 2H), 7.50 (d, J=8.7 Hz, 2H), 7.96 (d, J=16 Hz, 2H), 8.8 (br s, OH).

Melting Point 239-243° C., MS (ESI+) m/z 465 (M+1).

Example 89

Synthesis of (1E,6E)-1-(2-bromo-5-hydroxyphenyl)-7-(2-trifluoromethylphenyl)hepta-1,6-diene-3,5-dione (CU615)

The title compound was synthesized using the same procedure employed for Example 83 (2), but with 2-trifluoromethyl benzaldehyde (9 µL, 0.07 mmol) instead of 5-hydroxy-2-methoxybenzaldehyde (10 mg, 0.07 mmol). The product was obtained as a solid (1.1 mg, 5%) having the following characteristics.

1H NMR ($\delta$, acetone-$d_6$): 6.20 (s, 1H), 6.85 (d, J=16 Hz, 1H), 6.88 (dd, J=2.9, 8.7 Hz, 1H), 7.00 (d, J=16 Hz, 1H), 7.33 (d, J=2.9 Hz, 1H), 7.51 (d, J=8.7 Hz, 1H), 7.64 (dd, J=7.7, 7.7 Hz, 1H), 7.75 (dd, J=7.7, 7.7 Hz, 1H), 7.83 (d, J=7.7 Hz, 1H), 7.97 (d, J=16 Hz, 1H), 8.02 (d, J=16 Hz, 1H), 8.05 (d, J=7.7 Hz, 1H), 8.8 (br s, OH).

Melting Point 66-70° C., MS (ESI+) m/z 439 (M+1).

Example 90

Synthesis of (1E,6E)-1-(2-bromo-5-hydroxyphenyl)-7-(4-hydroxybiphenyl-2-yl)hepta-1,6-diene-3,5-dione (CU616)

The title compound was synthesized using the same procedure employed for Example 83 (2), but with 4-hydroxybiphenyl-2-carboxyaldehyde (14 mg, 0.07 mmol) instead of 5-hydroxy-2-methoxybenzaldehyde (10 mg, 0.07 mmol) The product was obtained as a solid (3.1 mg, 13%) having the following characteristics.

1H NMR ($\delta$, acetone-$d_6$): 6.08 (s, 1H), 6.78 (d, J=16 Hz, 1H), 6.79 (d, J=16 Hz, 1H), 6.87 (dd, J=2.9, 8.7 Hz, 1H), 7.01 (dd, J=~2, 8.2 Hz, 1H), 7.26 (d, J=8.2 Hz, 1H), 7.2~7.5 (m, 7H), 7.49 (d, J=8.7 Hz, 1H), 7.68 (d, J=16 Hz, 1H), 7.91 (d, J=16 Hz, 1H), 8.6 (br s, OH), 8.8 (br s, OH).

Melting Point 101-104° C., MS (ESI+) m/z 463 (M+1), 485 (M+Na).

Example 91

Synthesis of (1E,6E)-1-(2-benzoyloxy-4-diethylaminophenyl)-7-(4-hydroxyphenyl)hepta-1,6-diene-3,5-dione (CU425)

(1) Synthesis of 2-benzoyloxy-4-diethylaminobenzaldehyde

To a solution of 4-diethylamino-2-hydroxybenzaldehyde (300 mg, 1.55 mmol), pyridine (0.19 mL, 2.3 mmol) in 1.6 mL of dry dichloromethane was added benzoyl chloride (216 µL, 1.84 mmol) at 0° C. After being stirred at room temperature overnight, the reaction mixture was diluted with ethyl acetate. The mixture was washed with 1N HCl, saturated NaHCO$_3$ aqueous solution, brine, and dried over MgSO$_4$. After filtration, the filtrate was concentrated in vacuo, and the residue was purified by silica gel column chromatography (hexane/ethyl acetate=90/10 to 80/20) to obtain the title compound as a white solid (432 mg, 94%).

(2) Synthesis of (1E,6E)-1-(2-benzoyloxy-4-diethylaminophenyl)-7-(4-hydroxyphenyl)hepta-1,6-diene-3,5-dione (CU425)

The title compound was synthesized using the same procedure employed for Example 1, but with 2-benzoyloxy-4-diethylaminobenzaldehyde (34 mg, 0.11 mmol) instead of 2-chloro-4-hydroxybenzaldehyde (17 mg, 0.11 mmol). The product was obtained as a solid (13.8 mg, 32%) having the following characteristics.

$^1$H NMR ($\delta$, acetone-$d_6$): 1.20 (t, J=7 Hz, 6H), 3.49 (q, J=7 Hz, 4H), 5.81 (s, 1H), 6.58 (d, J=16 Hz, 1H), 6.61 (d, J=16 Hz, 1H), 6.65 (d, J=2.4 Hz, 1H), 6.73 (dd, J=2.4, 9.2 Hz, 1H), 6.89 (d, J=8.7 Hz, 2H), 7.52 (d, J=16 Hz, 1H), 7.53 (d, J=8.7 Hz, 2H), 7.66 (dd, J=7, 8 Hz, 2H), 7.68 (d, J=16 Hz, 1H), 7.72 (d, J=9.2 Hz, 1H), 7.78 (m, 1H), 8.25 (dd, J=1.5, 8.2 Hz, 2H).

Melting Point 212-215° C., MS (ESI+) m/z 484.4 (M+1), 506.3 (M+Na).

Example 92

Synthesis of (1E,6E)-1,7-bis(2-benzoyloxy-4-diethylaminophenyl)hepta-1,6-diene-3,5-dione (CU427)

The title compound was synthesized using the same procedure employed for Example 19, but with 2-benzoyloxy-4-diethylaminobenzaldehyde (74 mg, 0.25 mmol) instead of 2-chloro-4-hydroxybenzaldehyde (39 mg, 0.25 mmol). The product was obtained as a solid (12.2 mg, 19%) having the following characteristics.

$^1$H NMR ($\delta$, acetone-$d_6$): 1.19 (t, J=7 Hz, 12H), 3.48 (q, J=7 Hz, 8H), 5.66 (s, 1H), 6.53 (d, J=16 Hz, 2H), 6.63 (d, J=2.4 Hz, 2H), 6.71 (dd, J=2.4, 9.2 Hz, 2H), 7.61 (d, J=16 Hz, 2H), 7.63 (dd, J=7, 8 Hz, 4H), 7.68 (d, J=9.2 Hz, 2H), 7.76 (t, J=7 Hz, 2H), 8.22 (dd, J=1.5, 8 Hz, 4H).

Melting Point 192-196° C., MS (ESI+) m/z 659.5 (M+1).

Example 93

Synthesis of (1E,6E)-1-[2-(hydroxycarbonyl)phenyl]-7-(4-hydroxyphenyl)hepta-1,6-diene-3,5-dione (CU476)

The title compound was synthesized using the same procedure employed for Example 1, but with 2-formylbenzoic acid (17 mg, 0.11 mmol) instead of 2-chloro-4-hydroxybenzaldehyde (17 mg, 0.11 mmol). The product was obtained as a solid (9.0 mg, 30%) having the following characteristics.

MS (ESI+) m/z 359.4 (M+Na).

Example 94

Synthesis of (1E,6E)-1-[2-(dimethylaminocarbonyl)phenyl]-7-(4-hydroxyphenyl)hepta-1,6-diene-3,5-dione (CU479)

(1) Synthesis of 2-formyl-N,N-dimethylbenzamide

To a solution of 2-formylbenzoic acid (500 mg, 3.33 mmol), N,N-diisopropylethylamine (0.58 mL, 3.3 mmol), and dimethylamine/ethanol solution (1.2 mL, 5.6 M, 6.7 mmol) in 3.3 mL of dichloromethane was added 1-ethyl-3-(3-dimethylaminopropyl)-3-ethylcarbodiimide monohydrochloride (1.28 g, 6.67 mmol) at 0° C. After being stirred at room temperature overnight, the reaction mixture was diluted with diethyl ether. The solution was washed with 1N HCl, saturated NaHCO$_3$ aqueous solution, brine, and dried over MgSO$_4$. After filtration, the filtrate was concentrated in vacuo to obtain the title compound as a slightly yellow oil (113 mg, 19%).

(2) Synthesis of (1E,6E)-1-[2-(dimethylaminocarbonyl)phenyl]-7-(4-hydroxyphenyl)hepta-1,6-diene-3,5-dione (CU479)

The title compound was synthesized using the same procedure employed for Example 1, but with 2-formyl-N,N-dimethylbenzamide (20 mg, 0.11 mmol) instead of 2-chloro-4-hydroxybenzaldehyde (17 mg, 0.11 mmol). The product was obtained as a solid (15.0 mg, 47%) having the following characteristics.

$^1$H NMR ($\delta$, acetone-$d_6$): 2.81 (s, 3H), 3.11 (s, 3H), 6.03 (s, 1H), 6.71 (d, J=16 Hz, 1H), 6.85 (d, J=16 Hz, 1H), 6.91 (d, J=8.7 Hz, 2H), 7.31 (m, 1H), 7.47 (m, 2H), 7.59 (d, J=8.7 Hz, 2H), 7.61 (d, J=16 Hz, 1H), 7.65 (d, J=16 Hz, 1H), 7.87 (m, 1H).

Melting Point 210-218° C., MS (ESI+) m/z 364.4 (M+1).

Example 95

Synthesis of (1E,6E)-1-[2-(dimethylaminosulfonyl)phenyl]-7-(4-hydroxyphenyl)hepta-1,6-diene-3,5-dione (CU480)

(1) Synthesis of 2-formyl-N,N-dimethylbenzenesulfonamide

To a solution of 2-sulfobenzaldehyde sodium salt (2.0 g, 9.6 mmol) in 0.8 mL of dry N,N-dimethylformamide was added thionyl chloride (7.0 mL, 96 mmol) under nitrogen at 0° C. After being stirred at 100° C. for 3 min, the reaction mixture was diluted with diethyl ether and water at 0° C., successively. The separated organic layer was washed with water, brine, and dried over $MgSO_4$. After filtration, the filtrate was concentrated in vacuo to obtain crude 2-formylbenzenesulfonyl chloride (0.75 g).

To a solution of the above product, pyridine (0.57 mL, 7.0 mmol), and N,N-dimethylaminopyridine (21 mg, 0.17 mmol) in 3.5 mL of dry dichloromethane was added dimethylamine/ethanol solution (0.62 mL, 5.6 M, 3.5 mmol) at 0° C. After being stirred at room temperature overnight, the reaction mixture was diluted with ethyl acetate. The solution was washed with 1N HCl, saturated $NaHCO_3$ aqueous solution, brine, and dried over $MgSO_4$. After filtration, the filtrate was concentrated in vacuo, and the residue was purified with silica gel column chromatography (hexane/ethyl acetate=80/20 to 50/50) to obtain the title compound as a colorless oil (280 mg, 2 steps 14%).

(2) Synthesis of (1E,6E)-1-[2-(dimethylaminosulfonyl)phenyl]-7-(4-hydroxyphenyl)hepta-1,6-diene-3,5-dione (CU480)

The title compound was synthesized using the same procedure employed for Example 1, but with 2-formyl-N,N-dimethylbenzenesulfonamide (24 mg, 0.11 mmol) instead of 2-chloro-4-hydroxybenzaldehyde (17 mg, 0.11 mmol). The product was obtained as a solid (12.4 mg, 35%) having the following characteristics.

$^1$H NMR (δ, acetone-$d_6$): 2.77 (s, 6H), 6.09 (s, 1H), 6.73 (d, J=16 Hz, 1H), 6.81 (d, J=16 Hz, 1H), 6.91 (d, J=8.7 Hz, 2H), 7.60 (d, J=8.7 Hz, 2H), 7.62 (m, 1H), 7.67 (d, J=16 Hz, 1H), 7.73 (m, 1H), 7.98 (d, J=8 Hz, 1H), 7.98 (d, J=8 Hz, 1H), 8.57 (d, J=16 Hz, 1H).

Melting Point 86-90° C., MS (ESI+) m/z 400.4 (M+1), 422.4 (M+Na).

Example 96

Synthesis of (1E,6E)-1-(4-hydroxyphenyl)-7-[2-(methylsulfonyloxy)phenyl]hepta-1,6-diene-3,5-dione (CU483)

(1) Synthesis of 2-formylphenyl methanesulfonate

To a solution of 2-hydroxybenzaldehyde (0.30 mL, 2.8 mmol) and pyridine (0.91 mL, 11.2 mmol) in 5.6 mL of dichloromethane was added methanesulfonyl chloride (0.65 mL, 8.4 mmol) at 0° C. After being stirred at room temperature overnight, the reaction mixture was diluted with ethyl acetate. The solution was washed with 1N HCl, saturated $NaHCO_3$ aqueous solution, brine, and dried over $MgSO_4$. After filtration, the filtrate was concentrated in vacuo, and the residue was purified by silica gel column chromatography (hexane/ethyl acetate=75/25 to 50/50) to obtain the title compound as a white solid (553 mg, 98%).

(2) Synthesis of (1E,6E)-1-(4-hydroxyphenyl)-7-[2-(methylsulfonyloxy)phenyl]hepta-1,6-diene-3,5-dione (CU483)

The title compound was synthesized using the same procedure employed for Example 1, but with 2-formylphenyl methanesulfonate (23 mg, 0.11 mmol) instead of 2-chloro-4-hydroxybenzaldehyde (17 mg, 0.11 mmol). The product was obtained as a solid (7.2 mg, 21%) having the following characteristics.

$^1$H NMR (δ, acetone-$d_6$): 3.41 (s, 3H), 6.09 (s, 1H), 6.72 (d, J=16 Hz, 1H), 6.91 (d, J=8.7 Hz, 2H), 6.94 (d, J=16 Hz, 1H), 7.42~7.56 (m, 3H), 7.59 (d, J=8.7 Hz, 2H), 7.67 (d, J=16 Hz, 1H), 7.90 (d, J=16 Hz, 1H), 7.94 (dd, J=~2, 9 Hz, 1H).

Melting Point 163-167° C., MS (ESI+) m/z 387.4 (M+1), 409.3 (M+Na).

Example 97

Synthesis of (1E,6E)-1-(4-hydroxyphenyl)-7-[2-(methylsulfinyl)phenyl]hepta-1,6-diene-3,5-dione (CU485)

(1) Synthesis of 2-(methylsulfinyl)benzaldehyde

To a solution of 2-(methylthio)benzaldehyde (500 mg, 3.28 mmol) in 6.6 mL of dichloromethane was added m-chlorobenzoic peracid (0.85 g, 4.9 mmol) at 0° C. After being stirred at room temperature for 1 h, the reaction mixture was diluted with ethyl acetate. The solution was washed with saturated $NaHCO_3$ aqueous solution, brine, and dried over $MgSO_4$. After filtration, the filtrate was concentrated in vacuo, and the residue was purified by silica gel column chromatography (hexane/ethyl acetate=50/50 to 15/85) to obtain the title compound as a white crystal (493 mg, 89%).

(2) Synthesis of (1E,6E)-1-(4-hydroxyphenyl)-7-[2-(methylsulfiny)phenyl]hepta-1,6-diene-3,5-dione (CU485)

The title compound was synthesized using the same procedure employed for Example 1, but with 2-(methylsulfinyl)benzaldehyde (19 mg, 0.11 mmol) instead of 2-chloro-4-hydroxybenzaldehyde (17 mg, 0.11 mmol). The product was obtained as a solid (5.6 mg, 18%) having the following characteristics.

$^1$H NMR (δ, acetone-$d_6$): 2.69 (s, 3H), 6.10 (s, 1H), 6.72 (d, J=16 Hz, 1H), 6.91 (d, J=16 Hz, 1H), 6.91 (d, J=8.7 Hz, 2H), 7.60 (d, J=8.7 Hz, 2H), 7.61 (m, 1H), 7.68 (d, J=16 Hz, 1H), 7.69 (ddd, J=1.0, 7.7, 8 Hz, 1H), 7.83 (d, J=16 Hz, 1H), 7.89 (d, J=7.7 Hz, 1H), 8.01 (dd, J=1.0, 7.7 Hz, 1H).

MS (ESI+) m/z 355.4 (M+1), 377.3 (M+Na).

Example 98

Synthesis of (1E,6E)-1-(2-fluoro-5-hydroxyphenyl)-7-(4-hydroxyphenyl)hepta-1,6-diene-3,5-dione (CU621)

The title compound was synthesized using the same procedure employed for Example 1, but with 2-fluoro-5-hydroxybenzaldehyde (16 mg, 0.11 mmol, prepared according to the procedure described in J. Med. Chem., (1986), 29, 1982-1988) instead of 2-chloro-4-hydroxybenzaldehyde (17 mg, 0.11 mmol). The product was obtained as a solid (9.5 mg, 33%) having the following characteristics.

1H NMR (δ, acetone-$d_6$): 6.08 (s, 1H), 6.71 (d, J=16 Hz, 1H), 6.84 (d, J=16 Hz, 1H), 6.91 (d, J=8.7 Hz, 2H), 6.87~6.93 (m, 1H), 7.05 (dd, J=9, 10.5 Hz, 1H), 7.17 (dd, J=2.9, 6.3 Hz, 1H), 7.59 (d, J=8.7 Hz, 2H), 7.66 (d, J=16 Hz, 1H), 7.68 (d, J=16 Hz, 1H), 8.7 (br s, OH).

Melting Point 205-209° C., MS (ESI+) m/z 327.4 (M+1).

Example 99

Synthesis of (1E,6E)-1-(2-fluorophenyl)-7-(4-hydroxyphenyl)hepta-1,6-diene-3,5-dione (CU622)

The title compound was synthesized using the same procedure employed for Example 1, but with 2-fluorobenzaldehyde (14 mg, 0.11 mmol) instead of 2-chloro-4-hydroxybenzaldehyde (17 mg, 0.11 mmol). The product was obtained as a solid (9.1 mg, 33%) having the following characteristics.

1H NMR (δ, acetone-$d_6$): 6.09 (s, 1H), 6.72 (d, J=16 Hz, 1H), 6.91 (d, J=8.7 Hz, 2H), 6.93 (d, J=16 Hz, 1H), 7.22 (dd, J=8.2, 11 Hz, 1H), 7.27 (t, J=7.7 Hz, 1H), 7.46 (m, 1H), 7.59 (d, J=8.7 Hz, 2H), 7.67 (d, J=16 Hz, 1H), 7.75 (d, J=16 Hz, 1H), 7.80 (dt, J=~2, 7.7 Hz, 1H), 9.1 (br s, OH).

Melting Point 146-150° C., MS (ESI+) m/z 311.5 (M+1).

Example 100

Synthesis of (1E,6E)-1-[2-(1H-1,2,4-triazol-1-yl)phenyl]-7-(4-hydroxyphenyl)hepta-1,6-diene-3,5-dione (CU623)

The title compound was synthesized using the same procedure employed for Example 1, but with 2-(1H-1,2,4-triazol-1-yl)benzaldehyde (19 mg, 0.11 mmol, prepared according to the procedure described in Aust. J. Chem., (1991), 44, 1097-1114) instead of 2-chloro-4-hydroxybenzaldehyde (17 mg, 0.11 mmol). The product was obtained as a solid (6.0 mg, 19%) having the following characteristics.

1H NMR (δ, acetone-$d_6$): 6.02 (s, 1H), 6.69 (d, J=16 Hz, 1H), 6.85 (d, J=16 Hz, 1H), 6.90 (d, J=8.7 Hz, 2H), 7.46 (d, J=16 Hz, 1H), 7.58 (d, J=8.7 Hz, 2H), 7.5-7.63 (m, 3H), 7.64 (d, J=16 Hz, 1H), 8.02 (m, 1H), 8.19 (s, 1H), 8.70 (s, 1H).

Melting Point 186-192° C., MS (ESI+) m/z 360 (M+1).

Example 101

Synthesis of (1E,6E)-1-(2-chlorophenyl)-7-(4-hydroxyphenyl)hepta-1,6-diene-3,5-dione (CU624)

The title compound was synthesized using the same procedure employed for Example 1, but with 2-chlorobenzaldehyde (16 mg, 0.11 mmol) instead of 2-chloro-4-hydroxybenzaldehyde (17 mg, 0.11 mmol). The product was obtained as a solid (5.1 mg, 18%) having the following characteristics.

1H NMR (δ, acetone-$d_6$): 6.10 (s, 1H), 6.73 (d, J=16 Hz, 1H), 6.91 (d, J=16 Hz, 1H), 6.92 (d, J=8.7 Hz, 2H), 7.42 (m, 2H), 7.52 (m, 1H), 7.60 (d, J=8.7 Hz, 2H), 7.68 (d, J=16 Hz, 1H), 7.90 (m, 1H), 8.01 (d, J=16 Hz, 1H), 8.9 (br s, OH).

Melting Point 158-161° C., MS (ESI+) m/z 327.3 (M+1).

Example 102

Synthesis of (1E,6E)-1-[2-(4-ethoxycarbonyl-1H-1,2,3-triazol-1-yl)phenyl]-7-(4-hydroxyphenyl)hepta-1,6-diene-3,5-dione (CU625)

(1) Synthesis of ethyl 1-(2-formylphenyl)-1H-1,2,3-triazol-4-carboxylate and ethyl 1-(2-formylphenyl)-1H-1,2,3-triazol-5-carboxylate To a solution of 2-azidobenzaldehyde (100 mg, 0.68 mmol) in 1.0 mL of dry N,N-dimethylformamide was added ethyl propiolate (0.14 mL, 1.4 mmol) at room temperature. After being stirred at 100° C. for 12 h, ethyl propiolate (0.14 mL, 1.4 mmol) was added again with additional stirring for 12 h. After cooling, the reaction mixture was diluted with a 5:1 solution (12 mL) of ethyl acetate and hexane. The solution was washed with water twice, brine, and dried over $Na_2SO_4$. After filtration, the filtrate was concentrated in vacuo, and the residue was purified with silica gel column chromatography (hexane/ethyl acetate=90/10 to 75/25) to obtain ethyl 1-(2-formylphenyl)-1H-1,2,3-triazol-4-carboxylate as a crystal (111 mg, 66%) and ethyl 1-(2-formylphenyl)-1H-1,2,3-triazol-5-carboxylate as a oil (28 mg, 17%).

(2) Synthesis of (1E,6E)-1-[2-(4-ethoxycarbonyl-1H-1,2,3-triazol-1-yl)phenyl]-7-(4-hydroxyphenyl)hepta-1,6-di ene-3,5-dione (CU625)

The title compound was synthesized using the same procedure employed for Example 1, but with ethyl 1-(2-formylphenyl)-1H-1,2,3-triazol-4-carboxylate (27 mg, 0.11 mmol) instead of 2-chloro-4-hydroxybenzaldehyde (17 mg, 0.11 mmol). The product was obtained as a solid (8.1 mg, 21%) having the following characteristics.

1H NMR (δ, acetone-$d_6$): 1.38 (t, J=6.9 Hz, 3H), 4.41 (q, J=6.9 Hz, 2H), 6.03 (s, 1H), 6.69 (d, J=16 Hz, 1H), 6.90 (d, J=16 Hz, 1H), 6.91 (d, J=8.7 Hz, 2H), 7.30 (d, J=16 Hz, 1H), 7.59 (d, J=8.7 Hz, 2H), 7.6-7.8 (m, 4H), 8.09 (d, J=6.9 Hz, 1H), 8.88 (s, 1H), 8.9 (br s, OH).

Melting Point 231-237° C., MS (ESI+) m/z 432.4 (M+1), 454.4 (M+Na).

Example 103

Synthesis of (1E,6E)-1-[2-(5-ethoxycarbonyl-1H-1,2,3-triazol-1-yl)phenyl]-7-(4-hydroxyphenyl)hepta-1,6-diene-3,5-dione (CU626)

The title compound was synthesized using the same procedure employed for Example 1, but with ethyl 1-(2-formylphenyl)-1H-1,2,3-triazol-5-carboxylate (27 mg, 0.11 mmol, synthesized in Example 102 (1)) instead of 2-chloro-4-hydroxybenzaldehyde (17 mg, 0.11 mmol). The product was obtained as a solid (2.7 mg, 7%) having the following characteristics.

1H NMR (δ, acetone-$d_6$): 1.15 (t, J=6.9 Hz, 3H), 4.20 (q, J=6.9 Hz, 2H), 5.98 (s, 1H), 6.68 (d, J=16 Hz, 1H), 6.79 (d, J=16 Hz, 1H), 6.90 (d, J=8.7 Hz, 2H), 7.58 (d, J=8.7 Hz, 2H), 7.5-7.75 (m, 5H), 8.06 (d, J=7.6 Hz, 1H), 8.41 (s, 1H), 8.9 (br s, OH).

Melting Point 93-96° C., MS (ESI+) m/z 432.4 (M+1), 454.4 (M+Na).

Example 104

Synthesis of (1E,6E)-1-(4-fluorobiphenyl-2-yl)-7-(4-hydroxyphenyl)hepta-1,6-diene-3,5-dione (CU640)

The title compound was synthesized using the same procedure employed for Example 1, but with 4-fluorobiphenyl-2-carboxyaldehyde (22 mg, 0.11 mmol, prepared according to the procedure described in J. Am. Chem. Soc, (2007), 129, 5288-5295) instead of 2-chloro-4-hydroxybenzaldehyde (17 mg, 0.11 mmol). The product was obtained as a solid (14.5 mg, 43%) having the following characteristics.

1H NMR ($\delta$, acetone-$d_6$): 6.00 (s, 1H), 6.69 (d, J=16 Hz, 1H), 6.89 (d, J=16 Hz, 1H), 6.90 (d, J=8.7 Hz, 2H), 7.26 (dt, J=2.4, 8.2 Hz, 1H), 7.35 (d, J=6.8 Hz, 2H), 7.4-7.6 (m, 5H), 7.58 (d, J=8.7 Hz, 2H), 7.63 (d, J=16 Hz, 1H), 7.67 (dd, J=2.4, 10.6 Hz, 1H), 8.9 (br s, OH).

Melting Point 187-191° C., MS (ESI+) m/z 387.5 (M+1), 409.4 (M+Na).

Example 105

Synthesis of (1E,6E)-1-(4-chlorobiphenyl-2-yl)-7-(4-hydroxyphenyl)hepta-1,6-diene-3,5-dione (CU641)

(1) Synthesis of 4-chlorobiphenyl-2-carboxyaldehyde

To a solution of 2-bromo-5-chlorobenzaldehyde (438 mg, 2.00 mmol) in 20 mL of N,N-dimethylformamide was added phenylboronic acid (366 mg, 3.00 mmol), triphenylphosphine (262 mg, 1.00 mmol), 2M sodium carbonate aqueous solution (8.0 mL, 16 mmol), palladium acetate (75 mg, 0.33 mmol) under argon. After being stirred at room temperature overnight, the reaction mixture was filtered. The filtrate was diluted with diethyl ether, and the solution was washed with brine, and dried over $MgSO_4$. After filtration, the filtrate was concentrated in vacuo, and the residue was purified by silica gel column chromatography (hexane/ethyl acetate=99/1 to 90/10) to obtain the title compound (199 mg, 46%).

(2) Synthesis of (1E,6E)-1-(4-chlorobiphenyl-2-yl)-7-(4-hydroxyphenyl)hepta-1,6-diene-3,5-dione (CU641)

The title compound was synthesized using the same procedure employed for Example 1, but with 4-chlorobiphenyl-2-carboxyaldehyde (24 mg, 0.11 mmol) instead of 2-chloro-4-hydroxybenzaldehyde (17 mg, 0.11 mmol). The product was obtained as a solid (14.5 mg, 41%) having the following characteristics.

1H NMR ($\delta$, acetone-$d_6$): 6.02 (s, 1H), 6.69 (d, T=16 Hz, 1H), 6.91 (d, J=8.7 Hz, 2H), 6.92 (d, J=16 Hz, 1H), 7.37 (m, 2H), 7.41 (d, J=8.2 Hz, 1H), 7.43-7.55 (m, 4H), 7.56 (d, J=16 Hz, 1H), 7.58 (d, J=8.7 Hz, 2H), 7.63 (d, J=16 Hz, 1H), 7.92 (d, J=1.9 Hz, 1H), 8.9 (br s, OH).

Melting Point 193-196° C., MS (ESI+) m/z 403.4 (M+1), 425.3 (M+Na).

Example 106

Synthesis of (1E,6E)-1-(4-hydroxy-2'-methylbiphenyl-2-yl)-7-(4-hydroxyphenyl)hepta-1,6-diene-3,5-dione (CU642)

(1) Synthesis of 4-hydroxy-2'-methylbiphenyl-2-carboxyaldehyde

To a solution of 2-bromo-5-hydroxybenzaldehyde (100 mg, 0.500 mmol) in 2.5 mL of N,N-dimethylformamide was added 2-methylphenylboronic acid (102 mg, 0.75 mmol), triphenylphosphine (39 mg, 0.15 mmol), 2M sodium carbonate aqueous solution (2.0 mL, 4.0 mmol), palladium acetate (12 mg, 50 µmol) under argon. After being stirred at 90° C. overnight, the reaction mixture was filtered. The filtrate was diluted with diethyl ether, and the solution was washed with brine, and dried over $MgSO_4$. After filtration, the filtrate was concentrated in vacuo, and the residue was purified by silica gel column chromatography (hexane/ethyl acetate=95/5 to 70/30) to obtain the title compound (87.9 mg, 83%).

(2) Synthesis of (1E,6E)-1-(4-hydroxy-2'-methylbiphenyl-2-yl)-7-(4-hydroxyphenyl)hepta-1,6-diene-3,5-dione (CU642)

The title compound was synthesized using the same procedure employed for Example 1, but with 4-hydroxy-2'-methylbiphenyl-2-carboxyaldehyde (23 mg, 0.11 mmol) instead of 2-chloro-4-hydroxybenzaldehyde (17 mg, 0.11 mmol). The product was obtained as a solid (20.5 mg, 59%) having the following characteristics.

1H NMR ($\delta$, acetone-$d_6$): 2.04 (s, 3H), 5.92 (s, 1H), 6.64 (d, J=16 Hz, 1H), 6.68 (d, J=16 Hz, 1H), 6.90 (d, J=8.7 Hz, 2H), 6.98 (dd, J=2.4, 8.2 Hz, 1H), 7.07 (d, J=8.2 Hz, 1H), 7.10 (br d, J=8 Hz, 1H), 7.23-7.4 (m, 5H), 7.56 (d, J=8.7 Hz, 2H), 7.60 (d, J=16 Hz, 1H), 8.8 (br s, OH).

Melting Point 173-177° C., MS (ESI+) m/z 399.4 (M+1), 421.4 (M+Na).

Example 107

Synthesis of (1E,6E)-1-(2'-ethoxy-4-hydroxybiphenyl-2-yl)-7-(4-hydroxyphenyl)hepta-1,6-diene-3,5-dione (CU643)

(1) Synthesis of 2'-ethoxy-4-hydroxybiphenyl-2-carboxyaldehyde

The title compound was synthesized using the same procedure employed for Example 106 (1), but with 2-ethoxyphenylboronic acid (124 mg, 0.75 mmol) instead of 2-methylphenylboronic acid (102 mg, 0.75 mmol), and the reaction temperature was room temperature. The product was obtained (118 mg, 97%).

(2) Synthesis of (1E,6E)-1-(2'-ethoxy-4-hydroxybiphenyl-2-yl)-7-(4-hydroxyphenyl)hepta-1,6-diene-3,5-dione (CU643)

The title compound was synthesized using the same procedure employed for Example 1, but with 2'-ethoxy-4-hydroxybiphenyl-2-carboxyaldehyde (27 mg, 0.11 mmol) instead of 2-chloro-4-hydroxybenzaldehyde (17 mg, 0.11 mmol). The product was obtained as a solid (6.8 mg, 18%) having the following characteristics.

1H NMR ($\delta$, acetone-$d_6$): 1.17 (t, J=6.8 Hz, 3H), 4.00 (m, 2H), 5.95 (s, 1H), 6.66 (d, J=16 Hz, 1H), 6.68 (d, J=16 Hz, 1H), 6.90 (d, J=8.7 Hz, 2H), 6.95 (dd, J=~2, 8.2 Hz, 1H), 7.02 (br t, J=7.2 Hz, 1H), 7.08 (br d, J=8.2 Hz, 1H), 7.14 (br d, J=8.2 Hz, 2H), 7.31 (br d, J=Hz, 1H), 7.36 (m, 1H), 7.45 (d, J=16 Hz, 1H), 7.57 (d, J=8.7 Hz, 2H), 7.60 (d, J=16 Hz, 1H), 8.7 (br s, OH).

Melting Point 111-115° C., MS (ESI+) m/z 429.4 (M+1), 451.4 (M+Na).

Example 108

Synthesis of (1E,6E)-1-[2-(1-benzyl-1H-1,2,3-triazol-4-yl)phenyl]-7-(4-hydroxyphenyl)hepta-1,6-diene-3,5-dione (CU644)

(1) Synthesis of 2-(1-benzyl-1H-1,2,3-triazol-4-yl)benzaldehyde and 2-(1-benzyl-1H-1,2,3-triazol-5-yl)benzaldehyde A solution of 2-ethynylbenzaldehyde (200 mg, 1.54 mmol) and benzyl azide (0.38 mL, 3.0 mmol) in 2.0 mL of N,N-dimethylformamide was stirred at 80° C. overnight. The reaction mixture was diluted with water, and the solution was extracted with a 5:1 solution (12 mL) of ethyl acetate and hexane. The extract was washed with water, brine, and dried over $MgSO_4$. After filtration, the filtrate was concentrated in vacuo, and the residue was purified with silica gel column chromatography (hexane/ethyl acetate=80/20 to 60/40) to obtain 2-(1-benzyl-1H-1,2,3-triazol-4-yl)benzaldehyde (259 mg, 65%) and 2-(1-benzyl-1H-1,2,3-triazol-5-yl)benzaldehyde (118 mg, 30%).

(2) Synthesis of (1E,6E)-1-[2-(1-benzyl-1H-1,2,3-triazol-4-yl)phenyl]-7-(4-hydroxyphenyl)hepta-1,6-diene-3,5-dione (CU644)

The title compound was synthesized using the same procedure employed for Example 1, but with 2-(1-benzyl-1H-1,2,3-triazol-4-yl)benzaldehyde (29 mg, 0.11 mmol) instead of 2-chloro-4-hydroxybenzaldehyde (17 mg, 0.11 mmol). The product was obtained as a solid (13.8 mg, 35%) having the following characteristics.

1H NMR (δ, acetone-$d_6$): 5.75 (s, 2H), 6.04 (s, 1H), 6.70 (d, J=16 Hz, 1H), 6.79 (d, J=16 Hz, 1H), 6.92 (d, J=8.7 Hz, 2H), 7.31-7.50 (m, 7H), 7.59 (d, J=8.7 Hz, 2H), 7.65 (d, J=16 Hz, 1H), 7.74 (dd, J=~2, 7.2 Hz, 1H), 7.86 (dd, J=~2, 7.7 Hz, 1H), 8.14 (d, J=16 Hz, 1H), 8.23 (s, 1H), 8.9 (br s, OH).

Melting Point 103-109° C., MS (ESI+) m/z 450.5 (M+1), 472.4 (M+Na).

Example 109

Synthesis of (1E,6E)-1-[2-(1-benzyl-1H-1,2,3-triazol-5-yl)phenyl]-7-(4-hydroxyphenyl)hepta-1,6-diene-3,5-dione (CU645)

The title compound was synthesized using the same procedure employed for Example 1, but with 2-(1-benzyl-1H-1,2,3-triazol-5-yl)benzaldehyde (29 mg, 0.11 mmol, synthesized in Example 108 (1)) instead of 2-chloro-4-hydroxybenzaldehyde (17 mg, 0.11 mmol). The product was obtained as a solid (7.4 mg, 19%) having the following characteristics.

1H NMR (δ, acetone-$d_6$): 5.45 (s, 2H), 5.92 (s, 1H), 6.67 (d, J=16 Hz, 1H), 6.68 (d, J=16 Hz, 1H), 6.91 (d, J=8.7 Hz, 2H), 6.95 (m, 2H), 7.15 (d, J=16 Hz, 1H), 7.16-7.22 (m, 3H), 7.29 (dd, J=~2, 7.7 Hz, 1H), 7.48 (dt, J=~2, 7.7 Hz, 1H), 7.57 (m, 1H), 7.58 (d, J=8.7 Hz, 2H), 7.63 (d, J=16 Hz, 1H), 7.75 (s, 1H), 7.91 (br d, J=7.7 Hz, 1H), 8.9 (br s, OH).

Melting Point 205-215° C., MS (ESI+) m/z 450.5 (M+1).

Example 110

Synthesis of (1E,6E)-1-[2-(1-ethoxycarbonylmethyl-1H-1,2,3-triazol-4-yl)phenyl]-7-(4-hydroxyphenyl)hepta-1,6-diene-3,5-dione (CU646)

(1) Synthesis of ethyl[4-(2-formylphenyl)-1H-1,2,3-triazol-1-yl]acetate and ethyl[5-(2-formylphenyl)-1H-1,2,3-triazol-1-yl]acetate The title compounds were synthesized using the same procedure employed for Example 108 (1), but with ethyl azidoacetate (0.35 mL, 3.0 mmol) instead of benzyl azide (0.38 mL, 3.0 mmol). The products were obtained as ethyl[4-(2-formylphenyl)-1H-1,2,3-triazol-1-yl]acetate (226 mg, 56%) and ethyl[5-(2-formylphenyl)-1H-1,2,3-triazol-1-yl]acetate (83 mg, 21%).

(2) Synthesis of (1E,6E)-1-[2-(1-ethoxycarbonylmethyl-1H-1,2,3-triazol-4-yl)phenyl]-7-(4-hydroxyphenyl)hepta-1,6-diene-3,5-dione (CU646)

The title compound was synthesized using the same procedure employed for Example 1, but with ethyl[4-(2-formylphenyl)-1H-1,2,3-triazol-1-yl]acetate (28 mg, 0.11 mmol) instead of 2-chloro-4-hydroxybenzaldehyde (17 mg, 0.11 mmol). The product was obtained as a solid (15.8 mg, 40%) having the following characteristics.

1H NMR (δ, acetone-$d_6$): 1.27 (t, J=7.2 Hz, 3H), 4.26 (q, J=7.2 Hz, 2H), 5.47 (s, 2H), 6.07 (s, 1H), 6.70 (d, J=16 Hz, 1H), 6.81 (d, J=16 Hz, 1H), 6.91 (d, J=8.7 Hz, 2H), 7.42-7.55 (m, 2H), 7.58 (d, J=8.7 Hz, 2H), 7.64 (d, J=16 Hz, 1H), 7.78 (d, J=7.2 Hz, 1H), 7.87 (d, J=7.7 Hz, 1H), 8.13 (d, J=16 Hz, 1H), 8.27 (s, 1H), 8.9 (br s, OH).

Melting Point 99-105° C., MS (ESI+) m/z 446.4 (M+1), 468.4 (M+Na).

Example 111

Synthesis of (1E,6E)-1-[2-(1-ethoxycarbonylmethyl-1H-1,2,3-triazol-5-yl)phenyl]-7-(4-hydroxyphenyl)hepta-1,6-diene-3,5-dione (CU647)

The title compound was synthesized using the same procedure employed for Example 1, but with ethyl[5-(2-formylphenyl)-1H-1,2,3-triazol-1-yl]acetate (28 mg, 0.11 mmol, synthesized in Example 110 (1)) instead of 2-chloro-4-hydroxybenzaldehyde (17 mg, 0.11 mmol). The product was obtained as a solid (9.2 mg, 23%) having the following characteristics.

1H NMR (δ, acetone-$d_6$): 1.11 (t, J=7.2 Hz, 3H), 4.07 (q, J=7.2 Hz, 2H), 5.17 (s, 2H), 6.00 (s, 1H), 6.69 (d, J=16 Hz, 1H), 6.83 (d, J=16 Hz, 1H), 6.91 (d, J=8.7 Hz, 2H), 7.41 (d, J=16 Hz, 1H), 7.46 (dd, J=~2, 8 Hz, 1H), 7.52-7.64 (m, 2H), 7.58 (d, J=8.7 Hz, 2H), 7.64 (d, J=16 Hz, 1H), 7.77 (s, 1H), 7.98 (br d, J=7.7 Hz, 1H), 8.9 (br s, OH).

Melting Point 169-174° C., MS (ESI+) m/z 446.5 (M+1), 468.4 (M+Na).

Example 112

Synthesis of (1E,6E)-1-[2-bromo-5-(methoxymethoxy)phenyl]-7-(4-hydroxyphenyl)hepta-1,6-diene-3,5-dione (CU648)

(1) Synthesis of 2-bromo-5-(methoxymethoxy)benzaldehyde

The title compound was synthesized using the same procedure employed for Example 113 (1), but with 2-bromo-5- hydroxybenzaldehyde (3.62 g, 18.0 mmol) instead of 5-hydroxy-2-nitrobenzaldehyde (3.00 g, 18.0 mmol). The product was obtained (4.65 g, 90%).

(2) Synthesis of (1E,6E)-1-[2-bromo-5-(methoxymethoxy)phenyl]-7-(4-hydroxyphenyl)hepta-1,6-diene-3,5-dione (CU648)

The title compound was synthesized using the same procedure employed for Example 1, but with 2-bromo-5-(methoxymethoxy)benzaldehyde (27 mg 0.11 mmol) instead of 2-chloro-4-hydroxybenzaldehyde (17 mg, 0.11 mmol). The product was obtained as a solid (4.4 mg, 12%) having the following characteristics.

1H NMR (δ, acetone-$d_6$): 3.46 (s, 3H), 5.27 (s, 2H), 6.10 (s, 1H), 6.73 (d, J=16 Hz, 1H), 6.87 (d, J=16 Hz, 1H), 6.91 (d, J=8.7 Hz, 2H), 7.04 (dd, J=2.9, 9.2 Hz, 1H), 7.51 (d, J=2.9 Hz, 1H), 7.61 (d, J=8.7 Hz, 2H), 7.61 (d, J=9 Hz, 1H), 7.68 (d, J=16 Hz, 1H), 7.91 (d, J=16 Hz, 1H), 8.9 (br s, OH).

MS (ESI+) m/z 431 (M+1), 453 (M+Na).

Example 113

Synthesis of (1E,6E)-1-(4-hydroxyphenyl)-7-[5-(methoxymethoxy)-2-nitrophenyl]hepta-1,6-diene-3,5-dione (CU649)

(1) Synthesis of 5-(methoxymethoxy)-2-nitrobenzaldehyde

To a solution of 5-hydroxy-2-nitrobenzaldehyde (3.00 g, 18.0 mmol) in 36 mL of dichloromethane was added N,N-diisopropylethylamine (9.2 mL, 54 mmol), 4-dimethylaminopyridine (0.22 g, 1.8 mmol), and chloromethyl methyl ether (2.7 mL, 36 mmol) at room temperature, successively. After being stirred at room temperature overnight, the reaction mixture was diluted with a 1:1 solution (200 mL) of ethyl acetate and hexane. The solution was washed with 1M HCl four times, saturated $NaHCO_3$ aqueous solution, brine, and dried over $MgSO_4$. After filtration, the filtrate was concentrated in vacuo to obtain the title compound as a white solid (3.71 g, 98%).

(2) Synthesis of (1E,6E)-1-(4-hydroxyphenyl)-7-[5-(methoxymethoxy)-2-nitrophenyl]hepta-1,6-diene-3,5-dione (CU649)

The title compound was synthesized using the same procedure employed for Example 1, but with 5-(methoxymethoxy)-2-nitrobenzaldehyde (23 mg, 0.11 mmol) instead of 2-chloro-4-hydroxybenzaldehyde (17 mg, 0.11 mmol). The product was obtained as a solid (9.4 mg, 27%) having the following characteristics.

1H NMR (δ, acetone-$d_6$): 3.49 (s, 3H), 5.41 (s, 2H), 6.12 (s, 1H), 6.73 (d, J=16 Hz, 1H), 6.82 (d, J=16 Hz, 1H), 6.91 (d, J=8.7 Hz, 2H), 7.25 (br d, J=9.2 Hz, 1H), 7.45 (br s, 1H), 7.60 (d, J=8.7 Hz, 2H), 7.68 (d, J=16 Hz, 1H), 8.08 (d, J=16 Hz, 1H), 8.13 (br d, J=9.2 Hz, 1H), 8.9 (br s, OH).

Melting Point 175-180° C., MS (ESI+) m/z 398 (M+1), 420 (M+Na).

Example 114

Synthesis of (1E,6E)-1-(2-azidophenyl)-7-(4-hydroxyphenyl)hepta-1,6-diene-3,5-dione (CU651)

The title compound was synthesized using the same procedure employed for Example 1, but with 2-azidobenzaldehyde (16 mg, 0.11 mmol, prepared according to the procedure described in J. Org. Chem., (1995), 60, 2254-2256) instead of 2-chloro-4-hydroxybenzaldehyde (17 mg, 0.11 mmol). The product was obtained as a solid (18.4 mg, 63%) having the following characteristics.

1H NMR (δ, acetone-$d_6$): 6.06 (s, 1H), 6.71 (d, J=16 Hz, 1H), 6.89 (d, J=16 Hz, 1H), 6.91 (d, J=8.7 Hz, 2H), 7.24 (t, J=7.6 Hz, 1H), 7.36 (d, J=7.9 Hz, 1H), 7.51 (dt, J=~2, 8 Hz, 1H), 7.59 (d, J=8.7 Hz, 2H), 7.66 (d, J=16 Hz, 1H), 7.81 (br d, J=8 Hz, 1H), 7.86 (d, J=16 Hz, 1H), 9.0 (br s, OH).

Melting Point 153-161° C., MS (ESI+) m/z 356.3 (M+Na).

Example 115

Synthesis of (1E,6E)-1-(2,3-dibromo-4-hydroxy-5-methoxyphenyl)-7-(4-hydroxyphenyl)hepta-1,6-diene-3,5-dione (CU652)

The title compound was synthesized using the same procedure employed for Example 1, but with 2,3-dibromo-4-hydroxy-5-methoxybenzaldehyde (34 mg, 0.11 mmol) instead of 2-chloro-4-hydroxybenzaldehyde (17 mg, 0.11 mmol). The product was obtained as a solid (23.2 mg, 53%) having the following characteristics.

1H NMR (δ, acetone-$d_6$): 3.99 (s, 3H), 6.01 (s, 1H), 6.69 (d, J=16 Hz, 1H), 6.81 (d, J=16 Hz, 1H), 6.91 (d, J=8.7 Hz, 2H), 7.53 (s, 1H), 7.58 (d, J=8.7 Hz, 2H), 7.65 (d, J=16 Hz, 1H), 8.02 (d, J=16 Hz, 1H).

Melting Point 215-218° C., MS (ESI+) m/z 495.4 (M+1).

Example 116

Synthesis of (1E,6E)-1-(2-bromo-3-hydroxyphenyl)-7-(4-hydroxyphenyl)hepta-1,6-diene-3,5-dione (CU655)

The title compound was synthesized using the same procedure employed for Example 1, but with 2-bromo-3-hydroxybenzaldehyde (22 mg, 0.11 mmol, prepared according to the procedure described in Eur. J. Org. Chem., (2007), 5726-5733) instead of 2-chloro-4-hydroxybenzaldehyde (17 mg, 0.11 mmol). The product was obtained as a solid (15.0 mg, 44%) having the following characteristics.

1H NMR (δ, acetone-$d_6$): 6.08 (s, 1H), 6.72 (d, J=16 Hz, 1H), 6.81 (d, J=16 Hz, 1H), 6.91 (d, J=8.7 Hz, 2H), 7.05 (dd, J=1.4, 7.7 Hz, 1H), 7.25 (t, J=7.7 Hz, 1H), 7.36 (dd, J=1.4, 7.7 Hz, 1H), 7.60 (d, J=8.7 Hz, 2H), 7.67 (d, J=16 Hz, 1H), 8.04 (d, J=16 Hz, 1H), 8.9 (br s, OH).

MS (ESI+) m/z 387.2 (M+1), 409.2 (M+Na).

Example 117

Synthesis of (1E,6E)-1-[2-(1H-tetrazol-5-yl)phenyl]-7-(4-hydroxyphenyl)hepta-1,6-diene-3,5-dione (CU656)

(1) Synthesis of 2-(1H-tetrazol-5-yl)benzaldehyde

To a solution of 5-phenyl-1H-tetrazole (500 mg, 3.42 mmol) in 10 mL of dry tetrahydrofuran was added dropwise s-butyllithium (1.04 mol/L, 6.6 mL, 6.9 mmol) under nitrogen at −78° C. After the reaction mixture was stirred at the same temperature for 30 min, N,N-dimethylformamide (2 mL, 30 mmol) was added dropwise. After the reaction mixture was stirred at room temperature for 10 min, 1M HCl (10 mL) was added. The solution was allowed to warm up to room temperature, diluted with ethyl acetate, and extracted. The extract was washed with brine, and dried over MgSO$_4$. After filtration, the filtrate was concentrated in vacuo, and the residue was purified by recrystallization (hexane 2.5 mL, ethyl acetate 2.5 mL) to obtain the title compound (390 mg, 99%).

(2) Synthesis of (1E,6E)-1-[2-(1H-tetrazol-5-yl)phenyl]-7-(4-hydroxyphenyl)hepta-1,6-diene-3,5-dione (CU656)

The title compound was synthesized using the same procedure employed for Example 1, but with 2-(1H-tetrazol-5-yl)benzaldehyde (19 mg, 0.11 mmol) instead of 2-chloro-4-hydroxybenzaldehyde (17 mg, 0.11 mmol). The product was obtained as a solid (3.5 mg, 11%) having the following characteristics.
MS (ESI+) m/z 361.5 (M+1), 383.3 (M+Na).

Example 118

Synthesis of (1E,6E)-1-[2-(1-benzyl-1H-tetrazol-5-yl)phenyl]-7-(4-hydroxyphenyl)hepta-1,6-diene-3,5-dione (CU657)

(1) Synthesis of 2-(1-benzyl-1H-tetrazol-5-yl)benzaldehyde

To a solution of 2-(1H-tetrazol-5-yl)benzaldehyde (100 mg, 0.57 mmol, synthesized in Example 117 (1)) in a 3:1 solution (4 mL) of tetrahydrofuran and N,N-dimethylformamide was added potassium carbonate (0.12 g, 0.86 mmol), benzyl bromide (82 µL, 0.69 mmol) at room temperature, successively. After being stirred at room temperature overnight, the reaction mixture was diluted with a 5:2 solution (7 mL) of ethyl acetate and hexane. The solution was washed with water twice, brine, and dried over MgSO$_4$. After filtration, the filtrate was concentrated in vacuo, and the residue was purified by silica gel column chromatography (hexane/ethyl acetate=100/0 to 80/20) to obtain the title compound (126 mg, 83%).

(2) Synthesis of (1E,6E)-1-[2-(1-benzyl-1H-tetrazol-5-yl)phenyl]-7-(4-hydroxyphenyl)hepta-1,6-diene-3,5-dione (CU657)

The title compound was synthesized using the same procedure employed for Example 1, but with 2-(1-benzyl-1H-tetrazol-5-yl)benzaldehyde (29 mg, 0.11 mmol) instead of 2-chloro-4-hydroxybenzaldehyde (17 mg, 0.11 mmol). The product was obtained as a solid (8.1 mg, 20%) having the following characteristics.
1H NMR (δ, acetone-d$_6$): 6.03 (s, 2H), 6.07 (s, 1H), 6.71 (d, J=16 Hz, 1H), 6.85 (d, J=16 Hz, 1H), 6.92 (d, J=8.7 Hz, 2H), 7.35-7.63 (m, 9H), 7.66 (d, J=16 Hz, 1H), 7.96 (dd, J=~2, 7.2 Hz, 1H), 8.03 (dd, J=~2, 7 Hz, 1H), 8.46 (d, J=16 Hz, 1H), 8.9 (br s, OH).
MS (ESI+) m/z 451.4 (M+1), 473.6 (M+Na).

Example 119

Synthesis of (1E,6E)-1-[2-(1-ethoxycarbonylmethyl-1H-tetrazol-5-yl)phenyl]-7-(4-hydroxyphenyl)hepta-1,6-diene-3,5-dione (CU658)

(1) Synthesis of ethyl[5-(2-formylphenyl)-1H-tetrazol-1-yl]acetate

The title compound was synthesized using the same procedure employed for Example 118 (1), but with ethyl bromoacetate (83 µL, 0.75 mmol) instead of benzyl bromide (82 µL, 0.69 mmol). The product was obtained (95 mg, 64%)

(2) Synthesis of (1E,6E)-1-[2-(1-ethoxycarbonylmethyl-1H-tetrazol-5-yl)phenyl]-7-(4-hydroxyphenyl)hepta-1,6-diene-3,5-dione (CU658)

The title compound was synthesized using the same procedure employed for Example 1, but with ethyl[5-(2-formylphenyl)-1H-tetrazol-1-yl]acetate (29 mg, 0.11 mmol) instead of 2-chloro-4-hydroxybenzaldehyde (17 mg, 0.11 mmol). The product was obtained as a solid (4.5 mg, 11%) having the following characteristics.
1H NMR (δ, acetone-d$_6$): 1.28 (t, J=7.2 Hz, 3H), 4.29 (q, J=7.2 Hz, 2H), 5.81 (s, 2H), 6.10 (s, 1H), 6.71 (d, J=16 Hz, 1H), 6.87 (d, J=16 Hz, 1H), 6.91 (d, J=8.7 Hz, 2H), 7.59 (d, J=8.7 Hz, 2H), 7.6-7.65 (m, 2H), 7.65 (d, J=16 Hz, 1H), 8.00 (br d, J=7.2 Hz, 1H), 8.04 (br d, J=7.7 Hz, 1H), 8.42 (d, J=16 Hz, 1H), 8.9 (br s, OH).
MS (ESI+) m/z 447.4 (M+1), 469.4 (M+Na).

Example 120

Synthesis of (1E,6E)-1-(2-bromo-4-hydroxyphenyl)-7-(4-hydroxyphenyl)hepta-1,6-diene-3,5-dione (CU671)

The title compound was synthesized using the same procedure employed for Example 1, but with 2-bromo-4-hydroxybenzaldehyde (22 mg, 0.11 mmol, prepared according to the procedure described in J. Organomet. Chem., (2003), 668, 101-122) instead of 2-chloro-4-hydroxybenzaldehyde (17 mg, 0.11 mmol). The product was obtained as a solid (7.2 mg, 21%) having the following characteristics.
1H NMR (δ, acetone-d$_6$): 6.00 (s, 1H), 6.67 (d, J=16 Hz, 1H), 6.73 (d, J=16 Hz, 1H), 6.90 (d, J=8.7 Hz, 2H), 7.05 (d, J=8.7 Hz, 1H), 7.52-7.60 (m, 4H), 7.62 (d, J=16 Hz, 1H), 7.88 (br s, 1H).
Melting Point 196-205° C., MS (ESI+) m/z 387.3 (M+1).

Example 121

Synthesis of (1E,6E)-1-(4-hydroxyphenyl)-7-(2-styrylphenyl)hepta-1,6-diene-3,5-dione (CU672)

The title compound was synthesized using the same procedure employed for Example 1, but with (E)-2-styrylbenzaldehyde (24 mg, 0.11 mmol, prepared according to the procedure described in Eur. J. Org. Chem., (2004), 3465-3476) instead of 2-chloro-4-hydroxybenzaldehyde (17 mg, 0.11 mmol). The product was obtained as a solid (7.6 mg, 22%) having the following characteristics.
1H NMR (δ, acetone-d$_6$): 6.09 (s, 1H), 6.71 (d, J=16 Hz, 1H), 6.78 (d, J=16 Hz, 1H), 6.91 (d, J=8.7 Hz, 2H), 7.14 (d, J=16 Hz, 1H), 7.28-7.47 (m, 5H), 7.59 (d, J=8.7 Hz, 2H), 7.65 (d, J=16 Hz, 1H), 7.64-7.69 (m, 3H), 7.74 (t, J=8 Hz, 2H), 8.12 (d, J=16 Hz, 1H), 8.9 (br s, OH).
Melting Point 119-128° C., MS (ESI+) m/z 395.4 (M+1), 417.4 (M+Na).

Example 122

Synthesis of (1E,6E)-1-(4-hydroxy-2'-isobutoxybiphenyl-2-yl)-7-(4-hydroxyphenyl)hepta-1,6-diene-3,5-dione (CU1084)

(1) Synthesis of 4-hydroxy-2'-isobutoxybiphenyl-2-carboxyaldehyde

The title compound was synthesized using the same procedure employed for Example 106 (1), but with 2-isobutoxyphenylboronic acid (146 mg, 0.75 mmol) instead of 2-methylphenylboronic acid (102 mg, 0.75 mmol), and the reaction temperature was 50° C. The product was obtained (136 mg, quant.).

(2) Synthesis of (1E,6E)-1-(4-hydroxy-2'-isobutoxybiphenyl-2-yl)-7-(4-hydroxyphenyl)hepta-1,6-diene-3,5-dione (CU1084)

The title compound was synthesized using the same procedure employed for Example 1, but with 4-hydroxy-2'-isobutoxybiphenyl-2-carboxyaldehyde (30 mg, 0.11 mmol) instead of 2-chloro-4-hydroxybenzaldehyde (17 mg, 0.11 mmol). The product was obtained as a solid (3.6 mg, 9%) having the following characteristics.

1H NMR (δ, acetone-$d_6$): 0.82 (d, J=6.8 Hz, 6H), 1.84 (m, 1H), 3.72 (d, J=6.3 Hz, 2H), 5.93 (s, 1H), 6.66 (d, J=16 Hz, 1H), 6.68 (d, J=16 Hz, 1H), 6.90 (d, J=8.7 Hz, 2H), 6.96 (dd, J=2.5, 8.3 Hz, 1H), 7.02 (br t, J=7.4 Hz, 1H), 7.09 (br d, J=8.3 Hz, 1H), 7.10-7.15 (m, 2H), 7.33 (br d, J=2.5 Hz, 1H), 7.37 (m, 1H), 7.46 (d, J=16 Hz, 1H), 7.57 (d, J=8.7 Hz, 2H), 7.60 (d, J=16 Hz, 1H).

MS (ESI+) m/z 457 (M+1).

Example 123

Synthesis of (1E,6E)-1-[2-bromo-4-(piperidin-1-yl)phenyl]-7-(4-hydroxyphenyl)hepta-1,6-diene-3,5-dione (CU1090)

(1) Synthesis of 2-bromo-4-(piperidin-1-yl)benzaldehyde

To a solution of 2-bromo-4-fluorobenzaldehyde (300 mg, 1.48 mmol) in 3.0 mL of N,N-dimethylformamide was added potassium carbonate (204 mg, 1.48 mmol), piperidine (154 μL, 1.55 mmol) at room temperature. After being stirred at 110° C. overnight, the reaction mixture was diluted with a 2:1 solution of ethyl acetate and hexane. The solution was washed with water, brine, and dried over MgSO$_4$. After filtration, the filtrate was concentrated in vacuo, and the residue was purified by silica gel column chromatography (hexane/ethyl acetate=100/0 to 75/25) to obtain the title compound (355 mg, 90%).

(2) Synthesis of (1E,6E)-1-[2-bromo-4-(piperidin-1-yl)phenyl]-7-(4-hydroxyphenyl)hepta-1,6-diene-3,5-dione (CU1090)

The title compound was synthesized using the same procedure employed for Example 1, but with 2-bromo-4-(piperidin-1-yl)benzaldehyde (30 mg 0.11 mmol) instead of 2-chloro-4-hydroxybenzaldehyde (17 mg, 0.11 mmol). The product was obtained as a solid (17.5 mg, 44%) having the following characteristics.

1H NMR (δ, DMSO-$d_6$): 1.58 (m, 6H), 3.4 (m, 4H), 6.02 (s, 1H), 6.71 (d, J=16 Hz, 1H), 6.73 (d, J=16 Hz, 1H), 6.82 (d, J=8.5 Hz, 2H), 7.00 (dd, J=2, 9.1 Hz, 1H), 7.14 (d, J=2 Hz, 1H), 7.55 (d, J=16 Hz, 1H), 7.57 (d, J=8.5 Hz, 2H), 7.76 (br d, J=9 Hz, 1H), 7.79 (d, J=16 Hz, 1H).

Melting Point 238-248° C., MS (ESI+) m/z 454 (M+1).

Example 124

Synthesis of (1E,6E)-1-[4-(4-benzylpiperidin-1-yl)-2-bromophenyl]-7-(4-hydroxyphenyl)hepta-1,6-diene-3,5-dione (CU1091)

(1) Synthesis of 4-(4-benzylpiperidin-1-yl)-2-bromobenzaldehyde

The title compound was synthesized using the same procedure employed for Example 123 (1), but with 4-benzylpiperidine (275 μL, 1.55 mmol) instead of piperidine (154 μL, 1.55 mmol). The product was obtained (302 mg, 57%).

(2) (1E,6E)-1-[4-(4-benzylpiperidin-1-yl)-2-bromophenyl]-7-(4-hydroxyphenyl)hepta-1,6-diene-3,5-dione (CU1091)

The title compound was synthesized using the same procedure employed for Example 1, but with 4-(4-benzylpiperidin-1-yl)-2-bromobenzaldehyde (39 mg 0.11 mmol) instead of 2-chloro-4-hydroxybenzaldehyde (17 mg, 0.11 mmol). The product was obtained as a solid (18.0 mg, 38%) having the following characteristics.

1H NMR (δ, acetone-$d_6$): 1.33 (m, 2H), 1.74 (br d, J=12.6 Hz, 2H), 1.83 (m, 1H), 2.99 (d, J=7.2 Hz, 2H), 2.87 (m, 2H), 3.93 (br d, J=12.6 Hz, 2H), 5.97 (s, 1H), 6.65 (d, J=16 Hz, 1H), 6.68 (d, J=16 Hz, 1H), 6.90 (d, J=8.7 Hz, 2H), 6.99 (dd, J=2.4, 9.2 Hz, 1H), 7.15 (d, J=2.4 Hz, 1H), 7.14-7.3 (m, 5H), 7.57 (d, J=8.7 Hz, 2H), 7.61 (d, J=16 Hz, 1H), 7.73 (d, J=9.2 Hz, 1H), 7.95 (d, J=16 Hz, 1H), 8.9 (br s, OH).

Melting Point 155-161° C., MS (ESI+) m/z 544 (M+1).

Example 125

Synthesis of (1E,6E)-1-[4-(4-benzyl-1,4-diazepan-1-yl)-2-bromophenyl]-7-(4-hydroxyphenyl)hepta-1,6-diene-3,5-dione (CU1092)

(1) Synthesis of 4-(4-benzyl-1,4-diazepan-1-yl)-2-bromobenzaldehyde

The title compound was synthesized using the same procedure employed for Example 123 (1), but with N-benzylhomopiperazine (305 μL, 1.55 mmol) instead of piperidine (154 μL, 1.55 mmol). The product was obtained (498 mg, 90%).

(2) Synthesis of (1E,6E)-1-[4-(4-benzyl-1,4-diazepan-1-yl)-2-bromophenyl]-7-(4-hydroxyphenyl)hepta-1,6-diene-3,5-dione (CU1092)

The title compound was synthesized using the same procedure employed for Example 1, but with 4-(4-benzyl-1,4-diazepan-1-yl)-2-bromobenzaldehyde (41 mg 0.11 mmol) instead of 2-chloro-4-hydroxybenzaldehyde (17 mg, 0.11 mmol). The product was obtained as a solid (8.8 mg, 18%) having the following characteristics.

1H NMR (3, acetone-$d_6$): 1.96 (m, 2H), 2.63 (t, J=5.5 Hz, 2H), 2.78 (t, J=5.0 Hz, 2H), 3.6-3.7 (m, 6H), 5.96 (s, 1H), 6.62 (d, J=16 Hz, 1H), 6.68 (d, J=16 Hz, 1H), 6.84 (dd, J=2.5, 9.0 Hz, 1H), 6.91 (d, J=8.7 Hz, 2H), 7.00 (d, J=2.5 Hz, 1H), 7.2-7.35 (m, 5H), 7.58 (d, J=8.7 Hz, 2H), 7.61 (d, J=16 Hz, 1H), 7.73 (d, J=9.0 Hz, 1H), 7.98 (d, J=16 Hz, 1H).

MS (ESI+) m/z 559 (M+1).

Example 126

Synthesis of (1E,6E)-1-[2-bromo-4-(4-tert-butoxycarbonylpiperazin-1-yl)phenyl]-7-(4-hydroxyphenyl)hepta-1,6-diene-3,5-dione (CU1093)

(1) Synthesis of 2-bromo-4-(4-tert-butoxycarbonylpiperazin-1-yl)benzaldehyde The title compound was synthesized using the same procedure employed for Example 123 (1), but with N-tert-butoxycarbonylpiperazine (289 mg, 1.55 mmol) instead of piperidine (154 μL, 1.55 mmol). The product was obtained (392 mg, 72%).

(2) Synthesis of (1E,6E)-1-[2-bromo-4-(4-tert-butoxycarbonylpiperazin-1-yl)phenyl]-7-(4-hydroxyphenyl)hepta-1,6-diene-3,5-dione (CU1093)

The title compound was synthesized using the same procedure employed for Example 1, but with 2-bromo-4-(4-tert-butoxycarbonylpiperazin-1-yl)benzaldehyde (41 mg 0.11 mmol) instead of 2-chloro-4-hydroxybenzaldehyde (17 mg, 0.11 mmol) The product was obtained as a solid (16.2 mg, 33%) having the following characteristics.

1H NMR (δ, acetone-$d_6$): 1.47 (s, 9H), 3.36 (m, 4H), 3.56 (m, 4H), 5.99 (s, 1H), 6.69 (d, J=16 Hz, 1H), 6.70 (d, J=16 Hz, 1H), 6.91 (d, J=8.7 Hz, 2H), 7.04 (br d, J=9 Hz, 1H), 7.21 (d, J=2.6 Hz, 1H), 7.58 (d, J=8.7 Hz, 2H), 7.63 (d, J=16 Hz, 1H), 7.78 (d, J=8.9 Hz, 1H), 7.95 (d, J=16 Hz, 1H).

MS (ESI+) m/z 555 (M+1).

Example 127

Synthesis of (1E,6E)-1-[2-bromo-4-(4-tert-butoxycarbonyl-1,4-diazepan-1-yl)phenyl]-7-(4-hydroxyphenyl)hepta-1,6-diene-3,5-dione (CU1094)

(1) Synthesis of 2-bromo-4-(4-tert-butoxycarbonyl-1,4-diazepan-1-yl)benzaldehyde The title compound was synthesized using the same procedure employed for Example 123 (1), but with N-tert-butoxycarbonylhomopiperazine (321 μL, 1.55 mmol) instead of piperidine (154 μL, 1.55 mmol). The product was obtained (246 mg, 43%).

(2) Synthesis of (1E,6E)-1-[2-bromo-4-(4-tert-butoxycarbonyl-1,4-diazepan-1-yl)phenyl]-7-(4-hydroxyphenyl)hepta-1,6-diene-3,5-dione (CU1094)

The title compound was synthesized using the same procedure employed for Example 1, but with 2-bromo-4-(4-tert-butoxycarbonyl-1,4-diazepan-1-yl)benzaldehyde (42 mg 0.11 mmol) instead of 2-chloro-4-hydroxybenzaldehyde (17 mg, 0.11 mmol). The product was obtained as a solid (17.6 mg, 35%) having the following characteristics.

1H NMR (δ, acetone-$d_6$): 1.29 (s, 9H×0.5), 1.38 (s, 9H×0.5), 1.89 (m, 2H×0.5), 1.97 (m, 2H×0.5), 3.32 (m, 2H×0.5), 3.38 (m, 2H×0.5), 3.6-3.8 (m, 6H), 5.958 (s, 1H×0.5), 5.964 (s, 1H×0.5), 6.622 (d, J=16 Hz, 1H×0.5), 6.627 (d, J=16 Hz, 1H×0.5), 6.676 (d, J=16 Hz, 1H×0.5), 6.682 (d, J=16 Hz, 1H×0.5), 6.88 (br d, J=9 Hz, 1H), 6.906 (d, J=8.7 Hz, 2H×0.5), 6.913 (d, J=8.7 Hz, 2H×0.5), 7.05 (br s, 1H), 7.55-7.65 (m, 3H), 7.73 (br d, J=9 Hz, 1H), 7.97 (d, J=16 Hz, 1H), 8.9 (br s, OH).

MS (ESI+) m/z 569 (M+1).

Example 128

Synthesis of (1E,6E)-1-[2-bromo-4-(4-phenylpiperazin-1-yl)phenyl]-7-(4-hydroxyphenyl)hepta-1,6-diene-3,5-dione (CU1095)

(1) Synthesis of 2-bromo-4-(4-phenylpiperazin-1-yl)benzaldehyde

The title compound was synthesized using the same procedure employed for Example 123 (1), but with 4-phenylpiperazine (235 μL, 1.55 mmol) instead of piperidine (154 μL, 1.55 mmol). The product was obtained (393 mg, 77%).

(2) Synthesis of (1E,6E)-1-[2-bromo-4-(4-phenylpiperazin-1-yl)phenyl]-7-(4-hydroxyphenyl)hepta-1,6-diene-3,5-dione (CU1095)

The title compound was synthesized using the same procedure employed for Example 1, but with 2-bromo-4-(4-phenylpiperazin-1-yl)benzaldehyde (38 mg 0.11 mmol) instead of 2-chloro-4-hydroxybenzaldehyde (17 mg, 0.11 mmol). The product was obtained as a solid (11.2 mg, 24%) having the following characteristics.

1H NMR (δ, DMSO-$d_6$): 3.27 (m, 4H), 3.49 (m, 4H), 6.04 (s, 1H), 6.73 (d, J=16 Hz, 1H), 6.75-6.9 (m, 2H), 6.83 (d, J=8.6 Hz, 2H), 7.00 (d, J=8.0 Hz, 2H), 7.10 (br d, J=9 Hz, 1H), 7.22-7.30 (m, 3H), 7.57 (d, J=16 Hz, 1H), 7.59 (d, J=8.6 Hz, 2H), 7.81 (d, J=16 Hz, 1H), 7.83 (d, J=8.8 Hz, 1H).

Melting Point 195-204° C., MS (ESI+) m/z 531 (M+1).

Example 129

Synthesis of (1E,6E)-1-[2-bromo-4-(piperazin-1-yl)phenyl]-7-(4-hydroxyphenyl)hepta-1,6-diene-3,5-dione dihydrochloride (CU1097)

To a solution of (1E,6E)-1-[2-bromo-4-(4-tert-butoxycarbonylpiperazin-1-yl)phenyl]-7-(4-hydroxyphenyl)hepta-1,6-diene-3,5-dione (35 mg, 0.063 mmol, synthesized in Example 126) in 1.0 mL of ethyl acetate was added 3M HCl (1.0 mL) at room temperature. After being stirred at room temperature overnight, the reaction mixture was concentrated in vacuo. The residue was treated with diethyl ether, and the resulting solid was collected by filtration. The solid was rinsed with ether, and dried under reduced pressure to obtain the title compound as a solid (28.0 mg, 84%).

1H NMR (δ, DMSO-$d_6$): 3.19 (m, 4H), 3.55 (m, 4H), 6.05 (s, 1H), 6.74 (d, J=16 Hz, 1H), 6.83 (d, J=16 Hz, 1H), 6.84 (d, J=8.5 Hz, 2H), 7.09 (br d, J=9.0 Hz, 1H), 7.27 (d, J=2.4 Hz, 1H), 7.58 (d, J=16 Hz, 1H), 7.59 (d, J=8.5 Hz, 2H), 7.79 (d, J=16 Hz, 1H), 7.85 (d, J=9.0 Hz, 1H), 9.2 (br s, 2H).

MS (ESI+) m/z 455 (M+1).

Comparative Example 1

Synthesis of (1E,6E)-1-(2-amino-5-hydroxyphenyl)-7-(4-hydroxyphenyl)hepta-1,6-diene-3,5-dione (CU488)

To a solution of (1E,6E)-1-(5-hydroxy-2-nitrophenyl)-7-(4-hydroxyphenyl)hepta-1,6-diene-3,5-dione (26 mg, 73 μmol, synthesized in Example 4) in 3.0 mL of ethyl acetate was added anhydrous tin(II) chloride (57 mg, 0.30 mmol) at room temperature. After being stirred at 60° C. for 1.5 h, the reaction mixture was cooled to room temperature, and was diluted with 10% methanol/chloroform and saturated NaHCO$_3$ aqueous solution, successively. The mixture was shaken before filtration to remove inorganic salts. The organic layer after separation was washed with brine, and dried over MgSO$_4$. After filtration, the filtrate was concentrated in vacuo, and the residue was purified by silica gel column chromatography (hexane/ethyl acetate=60/40 to 30/70) to obtain the title compound as a solid (6.8 mg, 37%) having the following characteristics.

$^1$H NMR (δ, acetone-d$_6$) 4.7 (br s 2H NH) 6.01 (s, 1H) 6.58 (d, J=16 Hz, 1H), 6.67 (d, J=16 Hz, 1H), 6.70 (d, J=8.7 Hz, 1H), 6.72 (dd, J=2.4, 8.7 Hz, 1H), 6.90 (d, J=8.7 Hz, 2H), 6.97 (d, J=2.4 Hz, 1H), 7.57 (d, J=8.7 Hz, 2H), 7.61 (d, J=16 Hz, 1H), 7.85 (d, J=16 Hz, 1H).

Melting Point 186-192° C., MS (ESI+) m/z 346.3 (M+Na).

Comparative Example 2

Synthesis of (1E,6E)-1-(2-amino-5-benzyloxyphenyl)-7-(4-hydroxyphenyl)hepta-1,6-diene-3,5-dione (CU489)

The title compound was synthesized using the same procedure employed for Comparative Example 1, but with (1E,6E)-1-(5-benzyloxy-2-nitrophenyl)-7-(4-hydroxyphenyl)hepta-1,6-diene-3,5-dione (10 mg, synthesized in Example 30) instead of (1E,6E)-1-(5-hydroxy-2-nitrophenyl)-7-(4-hydroxyphenyl)hepta-1,6-diene-3,5-dione (silica gel column chromatography: hexane/ethyl acetate=75/25 to 60/40). The product was obtained as a solid (3.3 mg, 35%) having the following characteristics.

$^1$H NMR (δ, acetone-d$_6$): 4.8 (br s, 2H, NH), 5.07 (s, 2H), 6.01 (s, 1H), 6.67 (d, J=16 Hz, 1H), 6.69 (d, J=16 Hz, 1H), 6.78 (d, J=8.7 Hz, 1H), 6.89 (dd, J=2.9, 8.7 Hz, 1H), 6.90 (d, J=8.7 Hz, 2H), 7.19 (d, J=2.9 Hz, 1H), 7.32 (t, J=7.2 Hz, 1H), 7.39 (t, J=7.2 Hz, 2H), 7.48 (d, J=7.2 Hz, 2H), 7.56 (d, J=8.7 Hz, 2H), 7.61 (d, J=16 Hz, 1H), 7.86 (d, J=16 Hz, 1H).

Melting Point 175-179° C., MS (ESI+) m/z 436.7 (M+Na).

Comparative Example 3

Synthesis of (1E,6E)-1-(4-hydroxyphenyl)-7-(3-methoxy-4-nitrophenyl)hepta-1,6-diene-3,5-dione (CU050)

The title compound was synthesized using the same procedure employed for Example 1, but with 3-methoxy-4-nitrobenzaldehyde (20 mg, 0.11 mmol) instead of 2-chloro-4-hydroxybenzaldehyde (17 mg, 0.11 mmol) The product was obtained as a solid (4.2 mg, 13%) having the following characteristics.

$^1$H NMR (δ, acetone-d$_6$): 4.05 (s, 3H), 6.10 (s, 1H), 6.72 (d, J=16 Hz, 1H), 6.91 (d, J=8.7 Hz, 2H), 7.05 (d, J=16 Hz, 1H), 7.45 (dd, J=8.2 Hz, 1H), 7.60 (d, J=8.7 Hz, 2H), 7.66 (d, J=16 Hz, 1H), 7.66 (d, J=~2 Hz, 1H), 7.68 (d, J=16 Hz, 1H), 7.89 (d, J=8.2 Hz, 1H), 8.9 (br s, OH).

Melting Point 190-192° C., MS (ESI+) m/z 368 (M+1).

Test Example 1

Measurement of 50% Inhibition Concentration (IC$_{50}$) of β-Secretase (BACE-1) Enzyme Compounds were dissolved in 0.1 M sodium acetate buffer (with 150 mM sodium chloride, pH 4.5) and 10% dimethylsulfoxide (DMSO). The solution with no compound was used as a negative control. Then, 15 μL of these solutions (final compound concentration: 0.3, 0.9, 3.0, 9.0, and 30.0 μM), 1 unit/mL of recombinant human β-secretase (rhBACE-1, Invitrogen), and 15 μL of the fluorescent substrate peptide were mixed in a black 384-well microtiter plate (Coaster). After mixtures were incubated in the dark at 37° C. for 2.5 hr, the fluorescence intensities of the mixtures were measured by fluorescence microplate reader (Wallac) at 545 nm for excitation and at 590 nm for emission. The inhibition ratio of each compound was calculated using the intensity of the solution without any compound as a negative control. The sequence of the peptide was Ser-Glu-Val-Asn-Leu-Asp-Ala-Glu-Lys-Arg, and labeled with fluorescent donor (Cy3) at Ser-1 and with quencher (Cy5Q) at Lys-9, respectively (Invitrogen) Inhibitory activities of each compound are shown in FIG. 1.

As shown in FIG. 1, the compounds with halogen, nitro, trifluoromethyl, methoxycarbonyl, phenyl, or naphthyl residues at R$^1$, inhibited BACE-1 enzyme activity at low concentrate.

Test Example 2

Measurement of the Inhibitory Effect of CU532 on Aβ-40 and Aβ-42 Production in Rat Primary Cultured Cell Cerebral cortex was obtained from 19-20 day-old embryonic Wistar rat. The tissue was minced, dissociated using scalpel blades and Pasteur pipette in Hunks buffered solution, and centrifuged at 100 rpm. Precipitated cells were filtered using 100 μM cell strainer, and single cells were prepared. These cells were suspended in Eagle's Minimum Essential Medium (EMEM) containing 10% Fetal bovine serum, and plated into 48-well tissue culture plates (Becton Dickinson) at 200 μL/well and 1.7×10$^5$ cells/cm$^2$. Cultures were incubated at 37° C. in a humidified atmosphere of 5% CO$_2$. After 3, 5, and 7 days in culture, the medium was replaced, and after 9 days, CU532 was dissolved in DMSO and diluted in culture media so that the final concentration of DMSO in culture media was 0.1%, and each solution was added to each well at 200 mL/well for 72 hr. The control solution contained 0.1% DMSO.

After 72 hr, Aβ-40 and Aβ-42 in culture media were measured using by Aβ ELISA kit (Wako). 100 μL of the culture medium and standard diluents were added to the antibody-coated plate, and incubated at 4° C. over night. Then the plate was washed by wash buffer 5 times and 100 μL of HRP-labeled detection antibody solution was added to the plate. After 1 hour, the plate was washed 5 times, and TMB chromogenic reagent was added to the plate. After 30 minute, stop solution was added and absorbance at 450 nm of the solution was measured by microplate reader (BIORAD). The concentration of Aβ in culture medium was calculated from the standard curve.

As shown in FIG. 2, CU532 significantly decreased the amount of Aβ-40 or Aβ-42 in culture medium at 1 μM or 0.3 μM, respectively. But curcumin (cur) had no inhibitory effect on Aβ production.

Comparative Test Example 1

The IC50 of the compound (CU488) synthesized in Comparative Example 1 was determined in the same manner as in Test Example 1. CU488 is a compound obtained by converting the R$^1$ group in the general formula (I) in the compound (CU131) synthesized in Example 4 from an electron-withdrawing nitro group to an electron-donating amino group.

While the IC50 of CU131 was 0.91 μM, the IC50 of CU488 was 7.3 μM. This result shows that the β-secretase inhibiting activity is markedly reduced by converting the R$^1$ group from an electron-withdrawing group to an electron-donating group.

Comparative Test Example 2

The IC50 of the compound synthesized in Comparative Example 2 (CU489) was determined in the same manner as in Test Example 1. CU489 is a compound obtained by converting the $R^1$ group in the general formula (I) in the compound (CU475) synthesized in Example 30 from an electron-withdrawing nitro group to an electron-donating amino group.

While the IC50 of CU475 was 0.74 μM, the IC50 of CU489 was 5.6 μM. This result shows that the β-secretase inhibiting activity is markedly reduced by converting the $R^1$ group from an electron-withdrawing group to an electron-donating group.

Comparative Test Example 3

The IC50 of the compound (CU050) synthesized in Comparative Example 3 was determined in the same manner as in Test Example 1. CU050 is a compound obtained by transferring the nitro group in the compound (CU481) synthesized in Example 33 from $R^1$ to $R^3$ in the general formula (I).

While the $IC_{50}$ of CU481 was 1.2 μM, the IC50 of CU050 was 16 μM. This result shows that the β-secretase inhibiting activity is markedly reduced by transferring an electron-withdrawing group to a position other than $R^1$.

The present specification encompasses the contents of the specification and/or drawings in a Japanese patent application (Japanese Patent Application No. 2008-141996), based on which the present application claims priority. Furthermore, all publications, patents, and patent applications which are cited in the specification are hereby incorporated in their entirety by reference into the present specification.

The invention claimed is:

1. A compound represented by the following general formula (I) or a salt thereof:

[Formula 1]

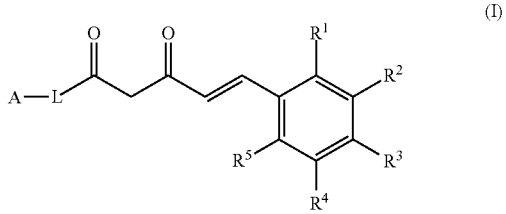

(I)

wherein A represents an aryl group that is optionally substituted or a heteroaryl group that is optionally substituted, L represents $CH_2$—$CH_2$ or CH=CH, $R^1$ is a chlorine atom, a bromine atom, or a nitro group, one $R^3$ and $R^4$ is a hydroxyl group and the other is a hydrogen atom, and $R^2$ and $R^5$ are each a hydrogen atom.

2. The compound according to claim 1 or a salt thereof, wherein in the general formula (I), $R^1$ is a nitro group, $R^2$, $R^3$, and $R^5$ are each a hydrogen atom, and $R^4$ is a hydroxyl group.

3. A β-secretase inhibitor, comprising a compound according to claim 1 or a salt thereof as an active ingredient.

4. A prophylactic or therapeutic agent for a disease associated with β-secretase, comprising a compound according claim 1, or a salt thereof as an active ingredient.

5. The compound according to claim 1 or a salt thereof, wherein in the general formula (I), A is an aryl group that is optionally substituted or a heteroaryl group that is optionally substituted, $R^1$ is an electron-withdrawing group, one of $R^3$ and $R^4$ is a hydroxyl group and the other is a hydrogen atom, $R^2$ and $R^5$ are the same or different and are each a hydrogen atom or a group with which a benzene ring can be substituted, and L is $CH_2$—$CH_2$ or CH=CH.

6. A compound represented by the following general formula (I) or a salt thereof:

[Formula 1]

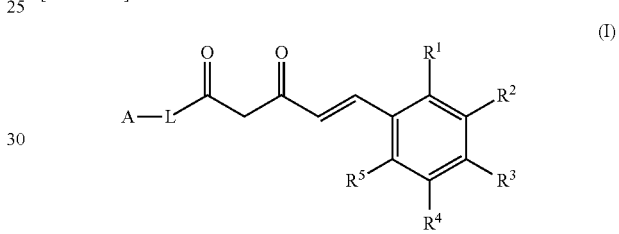

(I)

A is an aryl group that is optionally substituted or a heteroaryl group that is optionally substituted, $R^1$ is an electron-withdrawing group, one of $R^3$ and $R^4$ is a hydroxyl group and the other is a hydrogen atom or a group with which a benzene ring can be substituted, $R^2$ and $R^5$ are the same or different and are each a hydrogen atom or a group with which a benzene ring can be substituted, and L is $CH_2$—$CH_2$ or CH=CH.

* * * * *